US012799628B2

(12) United States Patent
Glanville et al.

(10) Patent No.: US 12,799,628 B2
(45) Date of Patent: Nov. 17, 2026

(54) ANTIGEN BINDING MOLECULES AND METHODS OF SCREENING THEREOF

(71) Applicant: ALEGRE USA LLC, London (GB)

(72) Inventors: Jacob Glanville, San Francisco, CA (US); Sawsan Youssef, Menlo Park, CA (US)

(73) Assignee: Charles River Laboratories, Inc., Wilmington, MA (US)

(*) Notice: Subject to any disclaimer, the term of this patent is extended or adjusted under 35 U.S.C. 154(b) by 960 days.

(21) Appl. No.: 17/591,115

(22) Filed: Feb. 2, 2022

(65) Prior Publication Data

US 2022/0154171 A1 May 19, 2022

Related U.S. Application Data

(63) Continuation of application No. PCT/US2020/045056, filed on Aug. 5, 2020.

(60) Provisional application No. 62/882,971, filed on Aug. 5, 2019.

(51) Int. Cl.

*C40B 30/04* (2006.01)
*C12N 15/10* (2006.01)

(52) U.S. Cl.

CPC .......... *C40B 30/04* (2013.01); *C12N 15/1065* (2013.01); *C12N 15/1086* (2013.01)

(58) Field of Classification Search

None

See application file for complete search history.

(56) References Cited

U.S. PATENT DOCUMENTS

2016/0355803 A1 12/2016 Poma et al.
2017/0051036 A1 2/2017 Jakobsen et al.
2018/0085457 A1 3/2018 Lu et al.

FOREIGN PATENT DOCUMENTS

CN 109306012 A 2/2019
WO 2016/014535 A1 1/2016
WO 2016/138034 A1 9/2016
WO 2019/089982 A1 5/2019

*Primary Examiner* — Christian C Boesen

(74) *Attorney, Agent, or Firm* — Ipsilon USA—NLO

(57) ABSTRACT

Described herein are methods of generating a library of cells expressing a plurality of polypeptides or recombinant polypeptides activated by an antigen and methods of panning said library of cells against a target antigen. The methods can be utilized for screening a library of chimeric antigen receptors reactive to a target antigen.

20 Claims, 43 Drawing Sheets

Specification includes a Sequence Listing.

DB-CART1.0-xCD19-mCherry-Origene plenti-C-HA-IRES-BSD Tagged Cloning Vector CAT#- PS100104
9446 bp 6 Hours Expression

Fig. 9B

Parental Jurkat NFkB GFP

Raji 6H

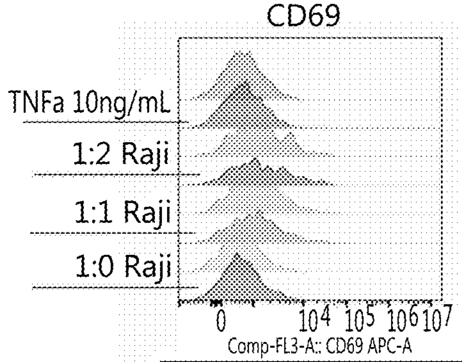

| | Sample name | Geometric Mean : Comp-FL3-A |
|---|---|---|
| | 02-20190604 CART GFP Raji Well-B9.fcs | 619 |
| | 02-20190604 CART GFP Raji Well-B8.fcs | 649 |
| | 02-20190604 CART GFP Raji Well-B7.fcs | 1283 |
| | 02-20190604 CART GFP Raji Well-B6.fcs | 1314 |
| | 02-20190604 CART GFP Raji Well-B5.fcs | 1152 |
| | 02-20190604 CART GFP Raji Well-B4.fcs | 1067 |
| | 02-20190604 CART GFP Raji Well-B3.fcs | 558 |
| | 02-Well-B2.fcs | 583 |

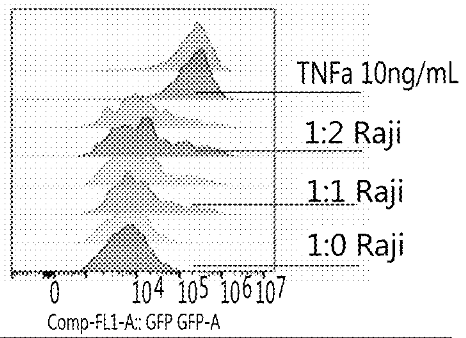

| | Sample name | Geometric Mean : Comp-FL1-A |
|---|---|---|
| | 02-20190604 CART GFP Raji Well-B9.fcs | 167247 |
| | 02-20190604 CART GFP Raji Well-B8.fcs | 168695 |
| | 02-20190604 CART GFP Raji Well-B7.fcs | 15960 |
| | 02-20190604 CART GFP Raji Well-B6.fcs | 17625 |
| | 02-20190604 CART GFP Raji Well-B5.fcs | 12420 |
| | 02-20190604 CART GFP Raji Well-B4.fcs | 13270 |
| | 02-20190604 CART GFP Raji Well-B3.fcs | 6510 |
| | 02-Well-B2.fcs | 6269 |

CD19-mCherry NFkB GFP

Raji 6H

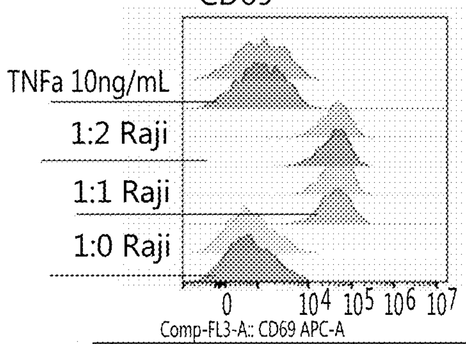

| | Sample name | Geometric Mean : Comp-FL3-A |
|---|---|---|
| | 02-20190604 CART GFP Raji Well-B9.fcs | 1096 |
| | 02-20190604 CART GFP Raji Well-B8.fcs | 1099 |
| | 02-20190604 CART GFP Raji Well-B7.fcs | 38250 |
| | 02-20190604 CART GFP Raji Well-B6.fcs | 36175 |
| | 02-20190604 CART GFP Raji Well-B5.fcs | 40422 |
| | 02-20190604 CART GFP Raji Well-B4.fcs | 37147 |
| | 02-20190604 CART GFP Raji Well-B3.fcs | 721 |
| | 02-Well-B2.fcs | 721 |

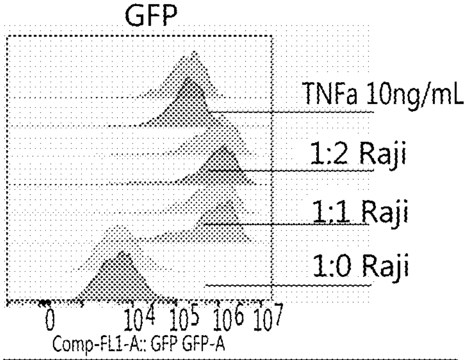

| | Sample name | Geometric Mean : Comp-FL1-A |
|---|---|---|
| | 02-20190604 CART GFP Raji Well-B9.fcs | 151059 |
| | 02-20190604 CART GFP Raji Well-B8.fcs | 149231 |
| | 02-20190604 CART GFP Raji Well-B7.fcs | 6.26E5 |
| | 02-20190604 CART GFP Raji Well-B6.fcs | 5.92E5 |
| | 02-20190604 CART GFP Raji Well-B5.fcs | 5.53E5 |
| | 02-20190604 CART GFP Raji Well-B4.fcs | 4.71E5 |
| | 02-20190604 CART GFP Raji Well-B3.fcs | 5393 |
| | 02-Well-B2.fcs | 5229 |

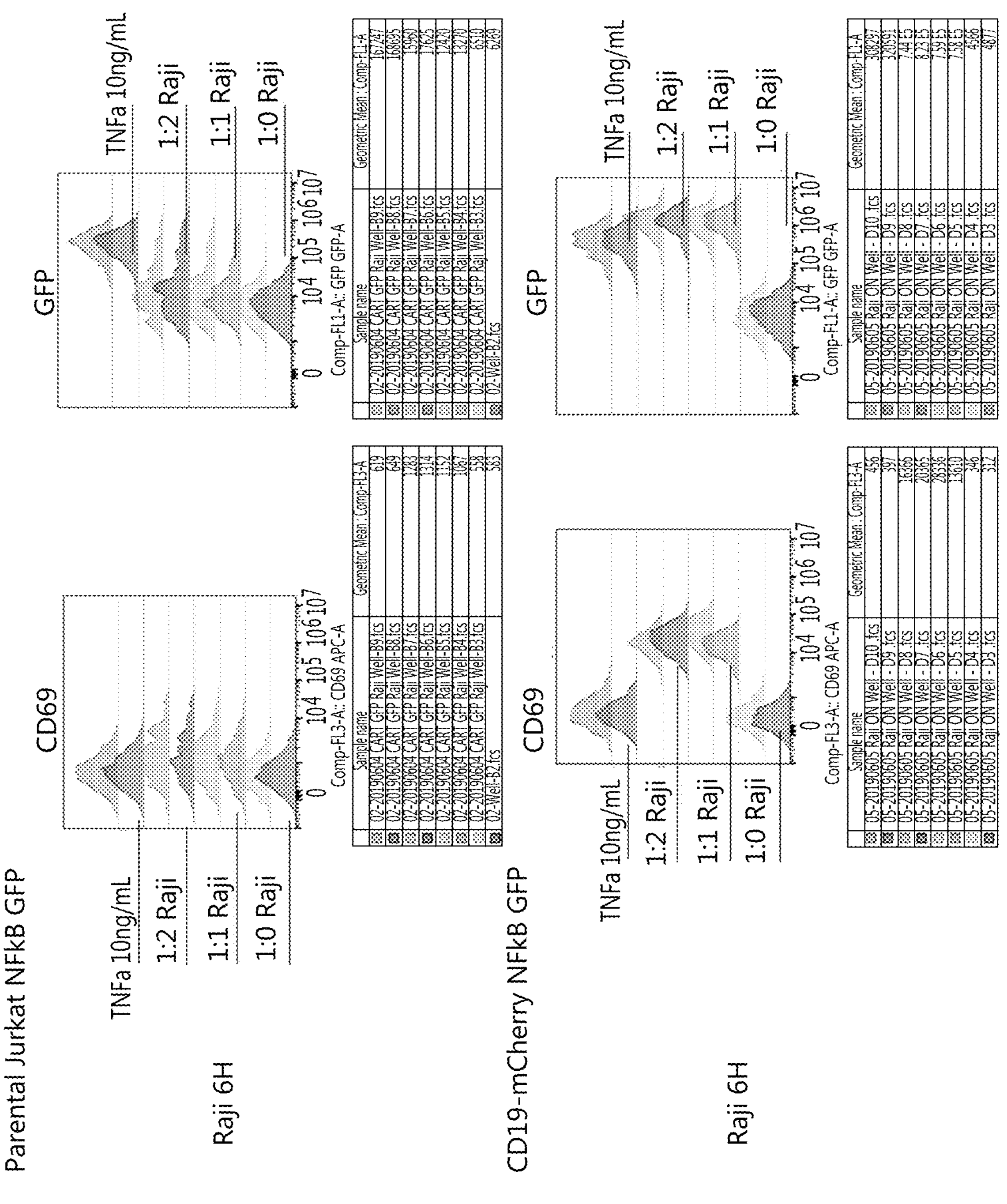

Fig. 9D

Parental Jurkat NFkB GFP – CD69

| Sample name | Geometric Mean : Comp-FL3-A |
|---|---|
| 02-20190604 CART GFP Raji Well-B9.fcs | 619 |
| 02-20190604 CART GFP Raji Well-B8.fcs | 649 |
| 02-20190604 CART GFP Raji Well-B7.fcs | 1283 |
| 02-20190604 CART GFP Raji Well-B6.fcs | 1314 |
| 02-20190604 CART GFP Raji Well-B5.fcs | 1152 |
| 02-20190604 CART GFP Raji Well-B4.fcs | 1067 |
| 02-20190604 CART GFP Raji Well-B3.fcs | 558 |
| 02-Well-B2.fcs | 583 |

Parental Jurkat NFkB GFP – GFP

| Sample name | Geometric Mean : Comp-FL1-A |
|---|---|
| 02-20190604 CART GFP Raji Well-B9.fcs | 167247 |
| 02-20190604 CART GFP Raji Well-B8.fcs | 168695 |
| 02-20190604 CART GFP Raji Well-B7.fcs | 15960 |
| 02-20190604 CART GFP Raji Well-B6.fcs | 17625 |
| 02-20190604 CART GFP Raji Well-B5.fcs | 12420 |
| 02-20190604 CART GFP Raji Well-B4.fcs | 13270 |
| 02-20190604 CART GFP Raji Well-B3.fcs | 6510 |
| 02-Well-B2.fcs | 6269 |

CD19-mCherry NFkB GFP – CD69

| Sample name | Geometric Mean : Comp-FL3-A |
|---|---|
| 05-20190605 Raji ON Well - D10 .fcs | 456 |
| 05-20190605 Raji ON Well - D9 .fcs | 397 |
| 05-20190605 Raji ON Well - D8 .fcs | 16366 |
| 05-20190605 Raji ON Well - D7 .fcs | 20365 |
| 05-20190605 Raji ON Well - D6 .fcs | 28336 |
| 05-20190605 Raji ON Well - D5 .fcs | 13610 |
| 05-20190605 Raji ON Well - D4 .fcs | 346 |
| 05-20190605 Raji ON Well - D3 .fcs | 312 |

CD19-mCherry NFkB GFP – GFP

| Sample name | Geometric Mean : Comp-FL1-A |
|---|---|
| 05-20190605 Raji ON Well - D10 .fcs | 308297 |
| 05-20190605 Raji ON Well - D9 .fcs | 320591 |
| 05-20190605 Raji ON Well - D8 .fcs | 7.44 E5 |
| 05-20190605 Raji ON Well - D7 .fcs | 8.23 E5 |
| 05-20190605 Raji ON Well - D6 .fcs | 7.59 E5 |
| 05-20190605 Raji ON Well - D5 .fcs | 7.58 E5 |
| 05-20190605 Raji ON Well - D4 .fcs | 4586 |
| 05-20190605 Raji ON Well - D3 .fcs | 4877 |

Fig. 10B

Daudi 6h

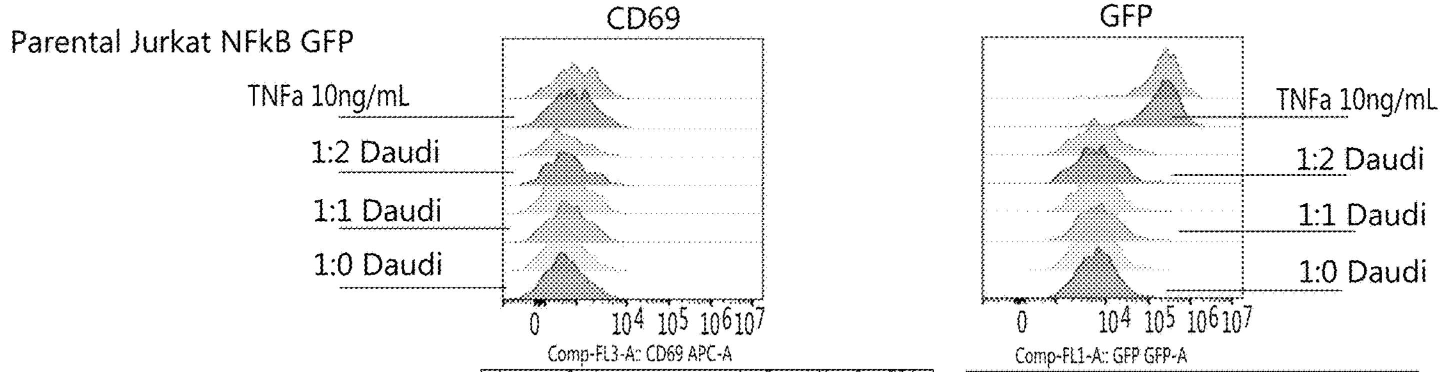

| | Sample name | Geometric Mean : Comp-FL3-A |
|---|---|---|
| | 03-20190604 GFP Daudi 6H Well-B9.fcs | 922 |
| | 03-20190604 GFP Daudi 6H Well-B8.fcs | 828 |
| | 03-20190604 GFP Daudi 6H Well-B7.fcs | 616 |
| | 03-20190604 GFP Daudi 6H Well-B6.fcs | 669 |
| | 03-20190604 GFP Daudi 6H Well-B5.fcs | 678 |
| | 03-20190604 GFP Daudi 6H Well-B4.fcs | 698 |
| | 03-20190604 GFP Daudi 6H Well-B3.fcs | 594 |
| | 03-Well-B2.fcs | 600 |

| | Sample name | Geometric Mean : Comp-FL1-A |
|---|---|---|
| | 03-20190604 GFP Daudi 6H Well-B9.fcs | 187998 |
| | 03-20190604 GFP Daudi 6H Well-B8.fcs | 175036 |
| | 03-20190604 GFP Daudi 6H Well-B7.fcs | 6751 |
| | 03-20190604 GFP Daudi 6H Well-B6.fcs | 6902 |
| | 03-20190604 GFP Daudi 6H Well-B5.fcs | 6869 |
| | 03-20190604 GFP Daudi 6H Well-B4.fcs | 7470 |
| | 03-20190604 GFP Daudi 6H Well-B3.fcs | 6188 |
| | 03-Well-B2.fcs | 6348 |

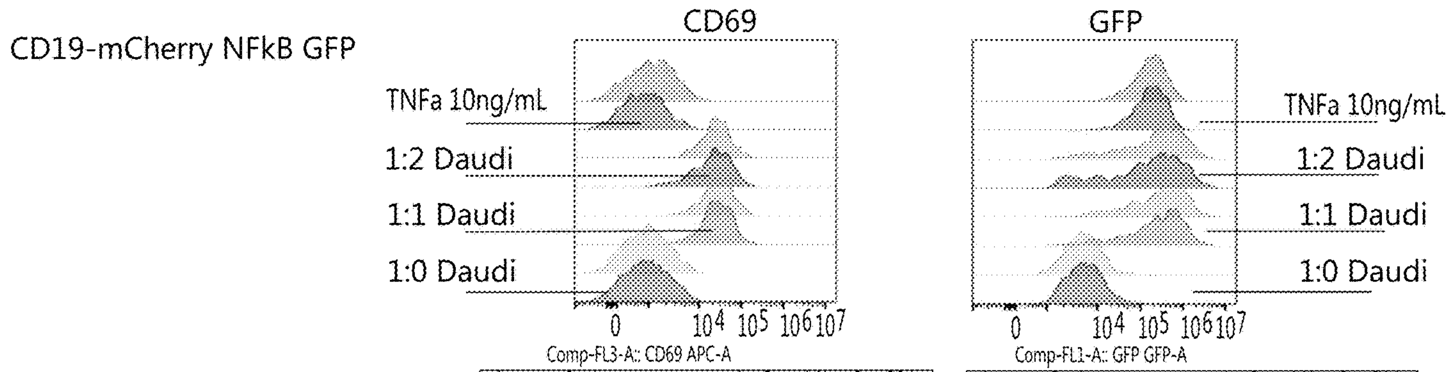

| | Sample name | Geometric Mean : Comp-FL3-A |
|---|---|---|
| | 03-20190604 GFP Daudi 6H Well-D9.fcs | 1084 |
| | 03-20190604 GFP Daudi 6H Well-D8.fcs | 774 |
| | 03-20190604 GFP Daudi 6H Well-D7.fcs | 22135 |
| | 03-20190604 GFP Daudi 6H Well-D6.fcs | 18643 |
| | 03-20190604 GFP Daudi 6H Well-D5.fcs | 25625 |
| | 03-20190604 GFP Daudi 6H Well-D4.fcs | 24636 |
| | 03-20190604 GFP Daudi 6H Well-D3.fcs | 884 |
| | 03-Well-D2.fcs | 891 |

| | Sample name | Geometric Mean : Comp-FL1-A |
|---|---|---|
| | 03-20190604 GFP Daudi 6H Well-D9.fcs | 153612 |
| | 03-20190604 GFP Daudi 6H Well-D8.fcs | 147134 |
| | 03-20190604 GFP Daudi 6H Well-D7.fcs | 170525 |
| | 03-20190604 GFP Daudi 6H Well-D6.fcs | 105921 |
| | 03-20190604 GFP Daudi 6H Well-D5.fcs | 229651 |
| | 03-20190604 GFP Daudi 6H Well-D4.fcs | 190836 |
| | 03-20190604 GFP Daudi 6H Well-D3.fcs | 5075 |
| | 03-Well-D2.fcs | 5409 |

Fig. 10D

Daudi Overnight

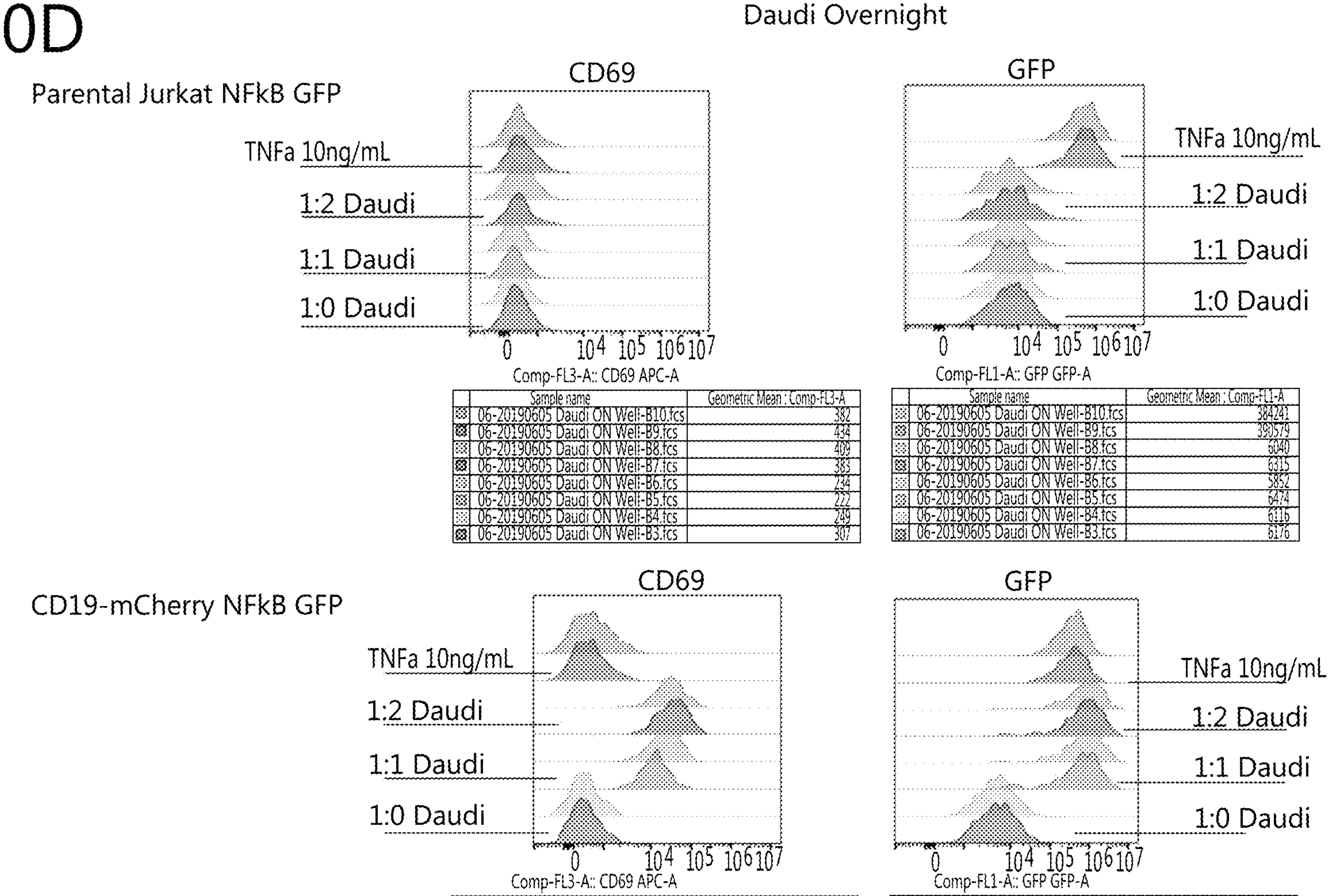

Parental Jurkat NFkB GFP — CD69 (Comp-FL3-A:: CD69 APC-A)

| | Sample name | Geometric Mean : Comp-FL3-A |
|---|---|---|
| | 06-20190605 Daudi ON Well-B10.fcs | 382 |
| | 06-20190605 Daudi ON Well-B9.fcs | 434 |
| | 06-20190605 Daudi ON Well-B8.fcs | 409 |
| | 06-20190605 Daudi ON Well-B7.fcs | 383 |
| | 06-20190605 Daudi ON Well-B6.fcs | 234 |
| | 06-20190605 Daudi ON Well-B5.fcs | 222 |
| | 06-20190605 Daudi ON Well-B4.fcs | 249 |
| | 06-20190605 Daudi ON Well-B3.fcs | 307 |

Parental Jurkat NFkB GFP — GFP (Comp-FL1-A:: GFP GFP-A)

| | Sample name | Geometric Mean : Comp-FL1-A |
|---|---|---|
| | 06-20190605 Daudi ON Well-B10.fcs | 384241 |
| | 06-20190605 Daudi ON Well-B9.fcs | 390579 |
| | 06-20190605 Daudi ON Well-B8.fcs | 6040 |
| | 06-20190605 Daudi ON Well-B7.fcs | 6315 |
| | 06-20190605 Daudi ON Well-B6.fcs | 5852 |
| | 06-20190605 Daudi ON Well-B5.fcs | 6474 |
| | 06-20190605 Daudi ON Well-B4.fcs | 6116 |
| | 06-20190605 Daudi ON Well-B3.fcs | 6176 |

CD19-mCherry NFkB GFP — CD69 (Comp-FL3-A:: CD69 APC-A)

| | Sample name | Geometric Mean : Comp-FL3-A |
|---|---|---|
| | 06-20190605 Daudi ON Well-B10.fcs | 571 |
| | 06-20190605 Daudi ON Well-B9.fcs | 490 |
| | 06-20190605 Daudi ON Well-B8.fcs | 26383 |
| | 06-20190605 Daudi ON Well-B7.fcs | 31869 |
| | 06-20190605 Daudi ON Well-B6.fcs | 21346 |
| | 06-20190605 Daudi ON Well-B5.fcs | 11780 |
| | 06-20190605 Daudi ON Well-B4.fcs | 368 |
| | 06-20190605 Daudi ON Well-B3.fcs | 371 |

CD19-mCherry NFkB GFP — GFP (Comp-FL1-A:: GFP GFP-A)

| | Sample name | Geometric Mean : Comp-FL1-A |
|---|---|---|
| | 06-20190605 Daudi ON Well-B10.fcs | 317193 |
| | 06-20190605 Daudi ON Well-B9.fcs | 307977 |
| | 06-20190605 Daudi ON Well-B8.fcs | 6.10E5 |
| | 06-20190605 Daudi ON Well-B7.fcs | 5.68E5 |
| | 06-20190605 Daudi ON Well-B6.fcs | 5.76E5 |
| | 06-20190605 Daudi ON Well-B5.fcs | 4.36E5 |
| | 06-20190605 Daudi ON Well-B4.fcs | 4734 |
| | 06-20190605 Daudi ON Well-B3.fcs | 4975 |

Fig. 11B

K562 6H

Parental Jurkat NFkB GFP

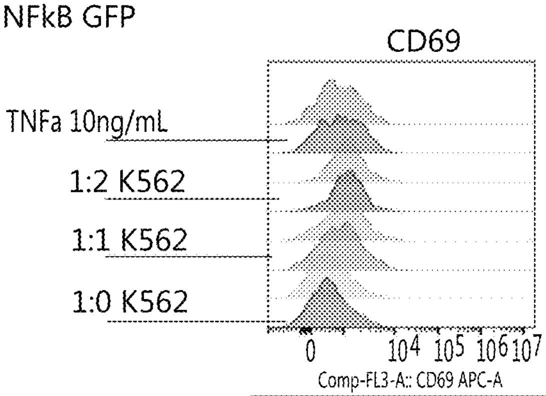

| | Sample name | Geometric Mean : Comp-FL3-A |
|---|---|---|
| | 04-20190604 GFP K562 6H Well-B9.fcs | 803 |
| | 04-20190604 GFP K562 6H Well-B8.fcs | 859 |
| | 04-20190604 GFP K562 6H Well-B7.fcs | 1167 |
| | 04-20190604 GFP K562 6H Well-B6.fcs | 1126 |
| | 04-20190604 GFP K562 6H Well-B5.fcs | 1038 |
| | 04-20190604 GFP K562 6H Well-B4.fcs | 870 |
| | 04-20190604 GFP K562 6H Well-B3.fcs | 537 |
| | 04-Well-B2.fcs | 539 |

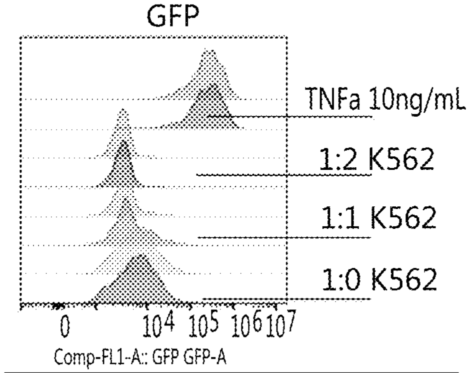

| | Sample name | Geometric Mean : Comp-FL1-A |
|---|---|---|
| | 04-20190604 GFP K562 6H Well-B9.fcs | 201617 |
| | 04-20190604 GFP K562 6H Well-B8.fcs | 192000 |
| | 04-20190604 GFP K562 6H Well-B7.fcs | 2996 |
| | 04-20190604 GFP K562 6H Well-B6.fcs | 3134 |
| | 04-20190604 GFP K562 6H Well-B5.fcs | 3701 |
| | 04-20190604 GFP K562 6H Well-B4.fcs | 4753 |
| | 04-20190604 GFP K562 6H Well-B3.fcs | 6147 |
| | 04-Well-B2.fcs | 6058 |

CD19-mCherry NFkB GFP

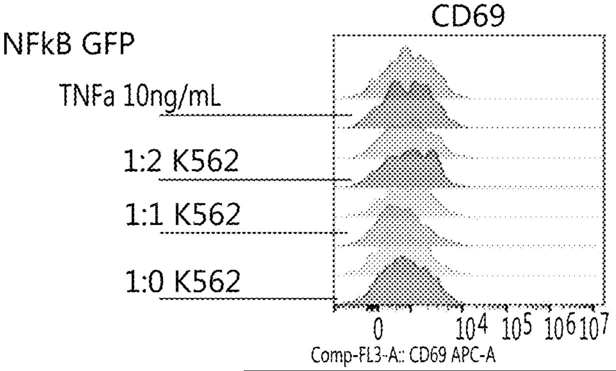

| | Sample name | Geometric Mean : Comp-FL3-A |
|---|---|---|
| | 04-20190604 GFP K562 6H Well-B9.fcs | 917 |
| | 04-20190604 GFP K562 6H Well-B8.fcs | 889 |
| | 04-20190604 GFP K562 6H Well-B7.fcs | 908 |
| | 04-20190604 GFP K562 6H Well-B6.fcs | 922 |
| | 04-20190604 GFP K562 6H Well-B5.fcs | 869 |
| | 04-20190604 GFP K562 6H Well-B4.fcs | 670 |
| | 04-20190604 GFP K562 6H Well-B3.fcs | 701 |
| | 04-Well-B2.fcs | 794 |

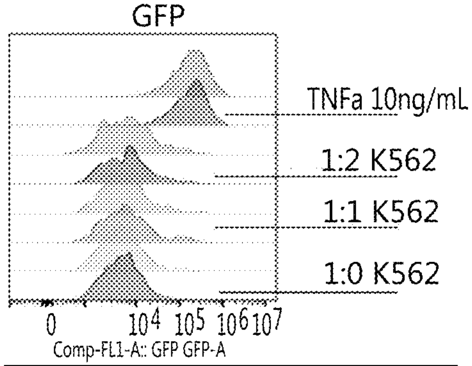

| | Sample name | Geometric Mean : Comp-FL1-A |
|---|---|---|
| | 04-20190604 GFP K562 6H Well-B9.fcs | 150777 |
| | 04-20190604 GFP K562 6H Well-B8.fcs | 143798 |
| | 04-20190604 GFP K562 6H Well-B7.fcs | 7055 |
| | 04-20190604 GFP K562 6H Well-B6.fcs | 6803 |
| | 04-20190604 GFP K562 6H Well-B5.fcs | 6157 |
| | 04-20190604 GFP K562 6H Well-B4.fcs | 6677 |
| | 04-20190604 GFP K562 6H Well-B3.fcs | 5063 |
| | 04-Well-B2.fcs | 5138 |

CD19-mCherry-NFkB-GFP #14a

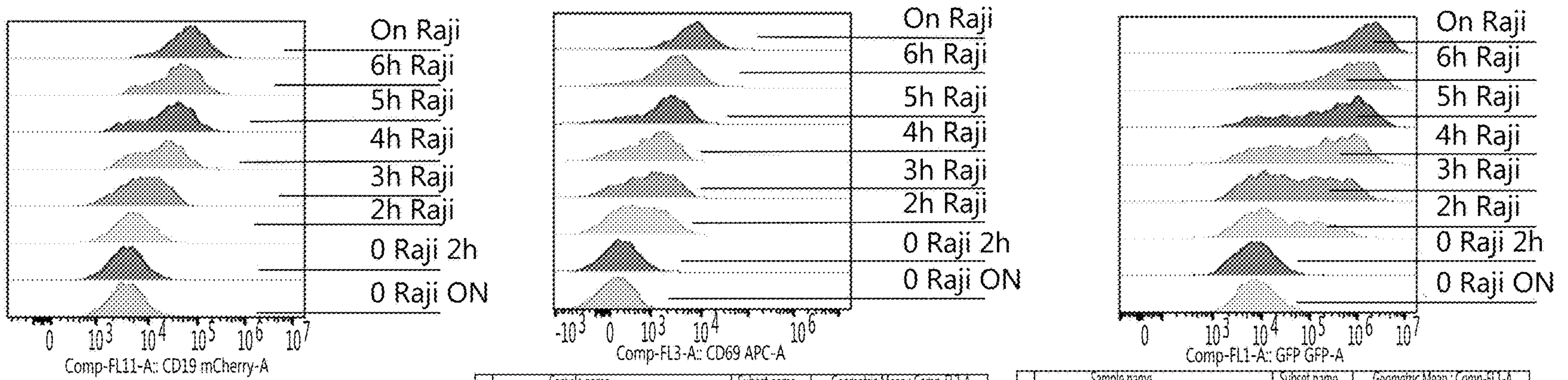

| Sample name | Subset name | Geometric Mean : Comp-FL11-A |
|---|---|---|
| 01-Overnight Well-A7.fcs | Mcherry+ | 1084 |
| 01-6hr Well-A6.fcs | Mcherry+ | 774 |
| 01-6hr Well-A5.fcs | Mcherry+ | 22135 |
| 01-6hr Well-A4.fcs | Mcherry+ | 18643 |
| 01-6hr Well-A3.fcs | Mcherry+ | 25625 |
| 01-2019 Raji violet w Jurkat 14A 2hr-A1.fcs | Mcherry+ | 24636 |
| 01-Jurkat only Well-A2.fcs | Mcherry+ | 884 |
| 01-Jurkat alone ON well-A9.fcs | Mcherry+ | 891 |

| Sample name | Subset name | Geometric Mean : Comp-FL3-A |
|---|---|---|
| 01-Overnight Well-A7.fcs | Mcherry+ | 1084 |
| 01-6hr Well-A6.fcs | Mcherry+ | 774 |
| 01-6hr Well-A5.fcs | Mcherry+ | 22135 |
| 01-6hr Well-A4.fcs | Mcherry+ | 18643 |
| 01-6hr Well-A3.fcs | Mcherry+ | 25625 |
| 01-2019 Raji violet w Jurkat 14A 2hr-A1.fcs | Mcherry+ | 24636 |
| 01-Jurkat only Well-A2.fcs | Mcherry+ | 884 |
| 01-Jurkat alone ON well-A9.fcs | Mcherry+ | 891 |

| Sample name | Subset name | Geometric Mean : Comp-FL1-A |
|---|---|---|
| 01-Overnight Well-A7.fcs | Mcherry+ | 1084 |
| 01-6hr Well-A6.fcs | Mcherry+ | 774 |
| 01-6hr Well-A5.fcs | Mcherry+ | 22135 |
| 01-6hr Well-A4.fcs | Mcherry+ | 18643 |
| 01-6hr Well-A3.fcs | Mcherry+ | 25625 |
| 01-2019 Raji violet w Jurkat 14A 2hr-A1.fcs | Mcherry+ | 24636 |
| 01-Jurkat only Well-A2.fcs | Mcherry+ | 884 |
| 01-Jurkat alone ON well-A9.fcs | Mcherry+ | 891 |

Fig. 12C

Fig. 14.1
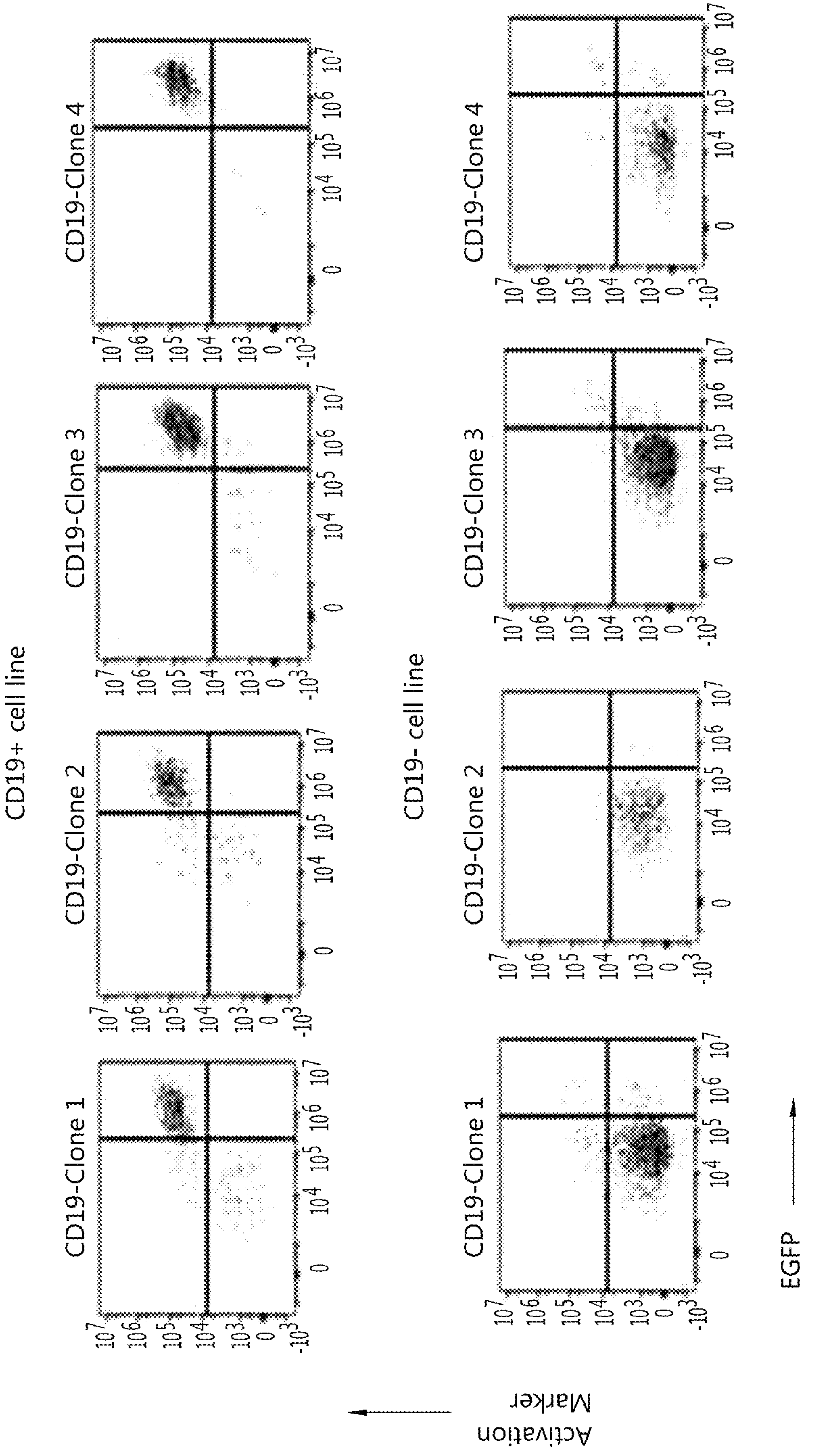

Fig. 14.2
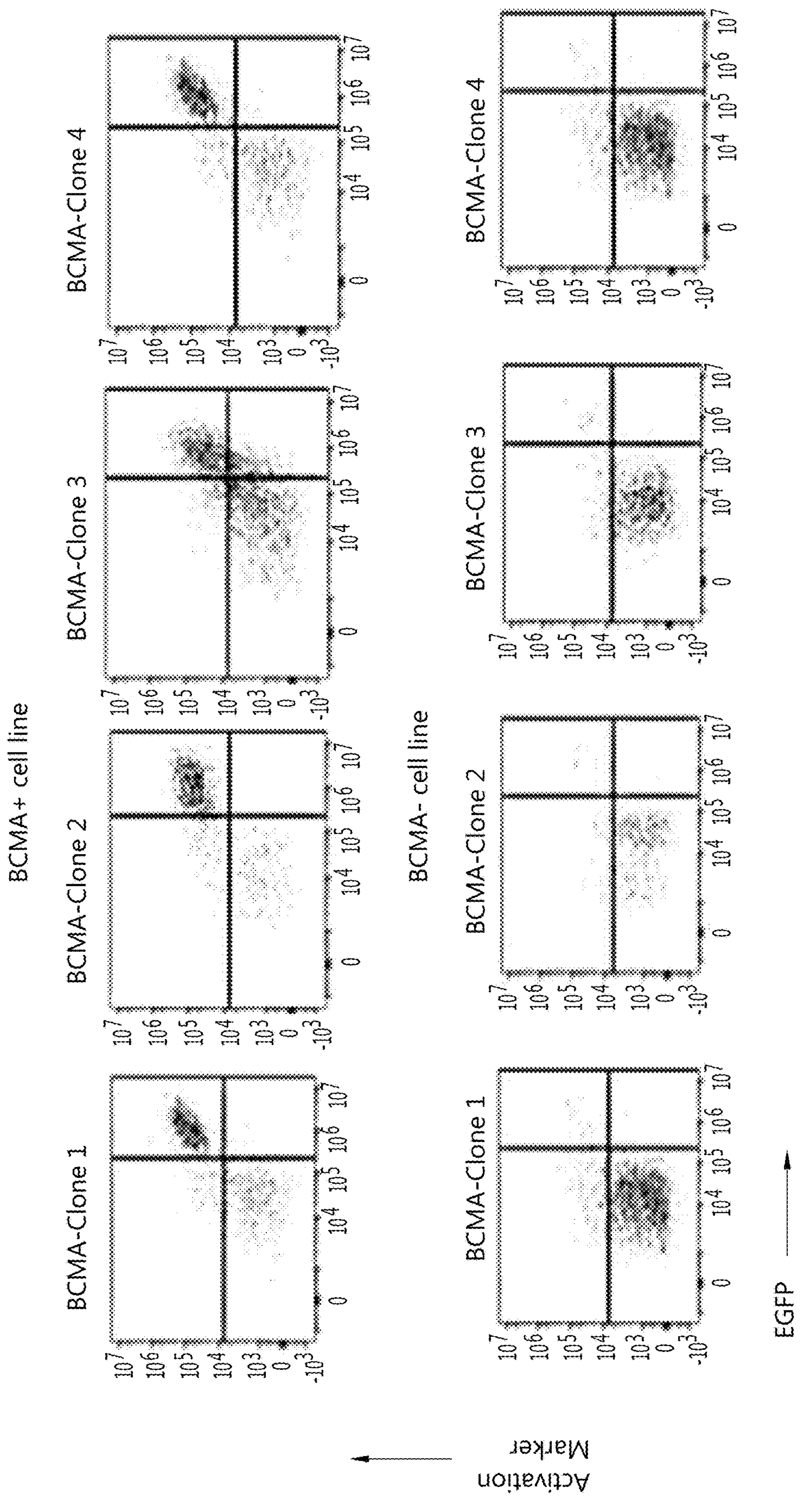

SEQUENCE LISTING

```
<160> NUMBER OF SEQ ID NOS: 1

<210> SEQ ID NO 1
<211> LENGTH: 2214
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atggccctgc ctgtgacagc cctgctgctg cctctggctc tgctgctgca tgccgctaga     60

cccggatccg aaattgtgat gacccagtca cccgccactc ttagcctttc acccggtgag    120

cgcgcaaccc tgtcttgcag agcctcccaa gacatctcaa aataccttaa ttggtatcaa    180

cagaagcccg gacaggctcc tcgccttctg atctaccaca ccagccggct ccattctgga    240

atccctgcca ggttcagcgg tagcggatct gggaccgact acaccctcac tatcagctca    300

ctgcagccag aggacttcgc tgtctatttc tgtcagcaag ggaacaccct gccctacacc    360

tttggacagg gcaccaagct cgagattaaa catgcatccg gtggaggcgg ttcaggcgga    420

ggtggctctg gcggtggcgg atcgaccggt caggtccaac tccaagaaag cggaccgggt    480

cttgtgaagc catcagaaac tctttcactg acttgtactg tgagcggagt gtctctcccc    540

gattacgggg tgtcttggat cagacagcca ccggggaagg gtctggaatg gattggagtg    600

atttggggct ctgagactac ttactactct tcatccctca agtcacgcgt caccatctca    660

aaggacaact ctaagaatca ggtgtcactg aaactgtcat ctgtgaccgc agccgacacc    720

gccgtgtact attgcgctaa gcattactat tacggcggga gctacgcaat ggattactgg    780

ggacagggta ctctggtcac cgtgtccagc cccgggacca caactccagc accacgacca    840

ccaacaccag cacctacaat cgcttctcag cctctgtccc tgcgcccaga ggcgtgccga    900

ccagctgcag gaggagcagt gcacacgagg ggactggact tcgcttgtga tatctacatc    960

tgggcgccct tggccgggac ttgtggggtc cttctcctgt cactggttat caccctttac   1020

tgcaaacggg gcagaaagaa actcctgtat atattcaaac aaccatttat gagaccagta   1080

caaactactc aagaggaaga tggctgtagc tgccgatttc cagaagaaga agaaggagga   1140

tgtgaactga gagtgaagtt cagcaggagc gcagacgccc ccgcgtacaa gcagggccag   1200

aaccagctct ataacgagct caatctagga cgaagagagg agtacgatgt tttggacaag   1260

agacgtggcc gggaccctga gatgggggga aagccgagaa ggaagaaccc tcaggaaggc   1320
```

-continued

```
ctgtacaatg aactgcagaa agataagatg gcggaggcct acagtgagat tgggatgaaa   1380

ggcgagcgcc ggaggggcaa ggggcacgac ggcctttacc agggtctcag tacagccacc   1440

aaggacacct acgacgccct tcacatgcag gccctgcccc ctcgcggtgg cggatctgga   1500

ggtggatcag tgagcaaggg tgaagaggat aacatggcta tcatcaagga gttcatgcgc   1560

ttcaaggtgc acatggaagg ctccgtgaac ggccacgagt tcgagatcga aggtgaagga   1620

gagggtcgcc catacgaggg cacccagacc gccaagctga aggtgaccaa gggtggcccc   1680

ctgcccttcg cctgggatat cctgtcccct cagttcatgt acggctccaa ggcctacgtg   1740

aagcaccccg ccgacatccc cgactacttg aagctgtcct tccccgaggg cttcaagtgg   1800

gagcgcgtga tgaacttcga ggacggcggc gtggtgaccg tgacccagga ctcctccctc   1860

caggacggcg agttcatcta caaggtgaag ctgcgcggca ccaacttccc ctccgacggc   1920

cccgtaatgc agaagaagac catgggctgg gaggcctcct ccgagcggat gtaccccgag   1980

gacggcgccc tgaagggcga gatcaagcag aggctgaagc tgaaggacgg cggccactac   2040

gacgctgagg tcaagaccac ctacaaggcc aagaagcccg tgcagctgcc cggcgcctac   2100

aacgtcaaca tcaagttgga catcacctcc cacaacgagg actacaccat cgtggaacag   2160

tacgaacgcg ccgagggccg ccactccacc ggcggcatgg acgagctgta caag         2214
```

ANTIGEN BINDING MOLECULES AND METHODS OF SCREENING THEREOF

CROSS-REFERENCE

This application is a continuation application of International Patent Application No. PCT/US2020/045056, filed on Aug. 5, 2020, which application claims the benefit of U.S. Patent Application No. 62/882,971 filed on Aug. 5, 2019, each of which is entirely incorporated herein by reference.

SEQUENCE LISTING

The instant application contains a Sequence Listing which has been submitted electronically in ASCII format and is hereby incorporated by reference in its entirety. Said ASCII copy, created on Feb. 11, 2022, is named 60864-704_301_SL.txt and is 3,356 bytes in size.

BACKGROUND

Chimeric antigen receptors (CAR) are synthetic constructs comprising antigen recognition or antigen binding domain fused to additional components such as hinge domains, transmembrane domains, co-stimulatory domains, and stimulatory domains. Primarily expressed by T cells for therapeutic uses, the binding of a target antigen to the CAR results in activation of a signaling cascade through the co-stimulatory domains and stimulatory domains that can be detected by an appropriate reporter or the expression of native T cell activation markers.

SUMMARY

Current methods for screening CARs reactive to a target antigen can produce false positive signals due to high levels of non-specific binding. In some instances, the background signal can mask the signal generated from the target antigen binding to the CAR. Accordingly, there remains a need for methods of screening CARs specific for a given target antigen. Such methods include steps that remove or negatively select for CARs that are reactive to a self-antigen that is not the target antigen or that, in general, have high levels of background activity. Additional advantages of screening for CARs by including a negative selection step is removing CARs that may react too strongly with self-antigen and, thus pose a safety risk; or allowing the discovery of CARs with lower reactivity to a target antigen that also potentially have therapeutic usefulness. In certain embodiments, the methods described herein are useful for screening for scFv molecules or light chain/heavy chain variable region pairs that are reactive to a target antigen and have low background reactivity.

Described herein is a method of screening a library of cells comprising: (a) contacting a plurality of cells with a target antigen; the plurality of cells comprising a recombinant polypeptide comprising an antigen binding domain, a transmembrane domain, an activation domain or an inhibition domain, wherein the antigen binding domain differs among the plurality of cells; (b) selecting cells that display specificity for the target antigen, thereby producing a first subset of antigen binding cells; (c) contacting the first subset of cells with a plurality of cells not expressing the target antigen; and (d) selecting cells of the first subset of antigen binding cells that do not display expression of a first activation marker, thereby producing a subset of low-background binding cells. In certain embodiments, the method further comprises contacting the subset of low-background binding cells to the target antigen and selecting cells from the low-background binding cells to the first activation marker, a second activation marker, or a third activation marker, thereby producing a subset of high antigen binding, low-background binding cells. In certain embodiments, the target antigen is expressed by a mammalian cell. In certain embodiments, the mammalian cell is a human cell. In certain embodiments, the target antigen is immobilized to a solid support. In certain embodiments, the solid support is a bead. In certain embodiments, the solid support is a column. In certain embodiments, the target antigen is a soluble antigen. In certain embodiments, the target antigen is conjugated to a detectable moiety. In certain embodiments, the detectable moiety is fluorescent. In certain embodiments, the recombinant polypeptide comprises a detectable tag. In certain embodiments, the detectable tag comprises a fluorescent moiety. In certain embodiments, the first activation marker, the second activation marker, and the third activation marker are the same. In certain embodiments, the plurality of cells further comprises a nucleic acid encoding a reporter nucleic acid. In certain embodiments, the reporter nucleic acid comprises a reporter gene under the control of an immune cell promoter. In certain embodiments, the reporter gene encodes a fluorescent protein or a luciferase protein. In certain embodiments, immune cell promoter comprises nuclear factor κB (NFκB) or NFAT or Nuclear factor of activated T-cells (NFAT). In certain embodiments, the first activation marker comprises the reporter nucleic acid. In certain embodiments, the second activation marker comprises the reporter nucleic acid. In certain embodiments, the third activation marker comprises the reporter nucleic acid. In certain embodiments, the first activation marker comprises an endogenous T cell activation marker. In certain embodiments, the second activation marker comprises an endogenous T cell activation marker. In certain embodiments, the third activation marker comprises an endogenous T cell activation marker. In certain embodiments, the endogenous T cell activation marker is selected from CD69, CD25, and a combination thereof. In certain embodiments, the antigen binding domain comprises a single-chain variable fragment (scFv). In certain embodiments, the recombinant polypeptide comprises two or more different antigen binding domains. In certain embodiments, one or more of the two or more different antigen binding domains binds to CD3. In certain embodiments, the antigen binding domain comprises a chimeric antigen receptor. In another aspect described herein is a method of screening a library of cells comprising: (a) contacting a plurality of cells with a target antigen; the plurality of cells comprising: a recombinant polypeptide comprising an antigen binding domain, a transmembrane domain, an activation domain or an inhibition domain, and a first detectable marker, wherein the antigen binding domain differs among the plurality of cells; and a reporter nucleic acid, the reporter nucleic acid configured to be activated upon binding of the target antigen to the antigen binding domain; (b) selecting cells that display expression of the reporter nucleic acid, thereby producing a first subset of activated cells; (c) contacting the first subset of activated cells with a plurality of cells not expressing the target antigen; and (d) selecting cells of the first subset of activated cells that do not display expression of the reporter nucleic acid, thereby producing a subset of low-background binding, activated cells. In certain embodiments, the method further comprising contacting the subset of low-background binding, activated cells to the target antigen and selecting cells from the low-background binding, activated cells that display activation of the reporter nucleic acid, a second activation marker, or a third activation marker, thereby producing a subset of high antigen binding, low-background binding activated cells. In certain embodiments, the target antigen is expressed by a mammalian cell. In certain embodiments, the mammalian cell is a human cell. In certain embodiments, the target antigen is immobilized to a solid support. In certain embodiments, the solid support is a bead. In certain embodiments, the solid support is a column. In certain embodiments, the target antigen is a soluble antigen. In certain embodiments, the target antigen is conjugated to a detectable moiety. In certain embodiments, the detectable moiety is fluorescent. In certain embodiments, the recombinant polypeptide comprises a detectable tag. In certain embodiments, the detectable tag comprises a fluorescent moiety. In certain embodiments, the reporter nucleic acid comprises a reporter gene under the control of an immune cell promoter. In certain embodiments, the reporter gene encodes a fluorescent protein or a luciferase protein. In certain embodiments, the immune cell promoter comprises nuclear factor κB (NFκB) or NFAT or Nuclear factor of activated T-cells (NFAT). In certain embodiments, the second activation marker comprises the reporter nucleic acid. In certain embodiments, the third activation marker comprises the reporter nucleic acid. In certain embodiments, the second activation marker comprises an endogenous T cell activation marker. In certain embodiments, the third activation marker comprises an endogenous T cell activation marker. In certain embodiments, the endogenous T cell activation marker is selected from CD69, CD25, and a combination thereof. In certain embodiments, the antigen binding domain comprises a single-chain variable fragment (scFv). In certain embodiments, the recombinant polypeptide comprises two or more different antigen binding domains. In certain embodiments, one or more of the two or more different antigen binding domains binds to CD3. In certain embodiments, the recombinant polypeptide comprises a chimeric antigen receptor.

In another aspect described herein is a method of screening a library of cells comprising: (a) contacting a plurality of cells with a target antigen; the plurality of cells comprising a recombinant polypeptide comprising an antigen binding domain, a transmembrane domain, an activation domain or an inhibition domain, and a first detectable marker, wherein the antigen binding domain differs among the plurality of cells; (b) selecting cells that display expression of an endogenous T cell activation marker, thereby producing a first subset of activated cells; (c) contacting the subset of activated cells with a plurality of cells not expressing the target antigen; and (d) selecting cells of the subset of activated cells that do not display expression of an endogenous T cell activation marker, thereby producing a subset of low-background binding, activated cells. In certain embodiments, the method further comprises contacting the subset of low-background, activated cells to the target antigen and selecting cells from the low-background, activated cells that display activation of the endogenous T cell activation marker, a second activation marker, or a third activation marker, thereby producing a subset of high antigen binding, low background binding activated cells. In certain embodiments, the target antigen is expressed by a mammalian cell. In certain embodiments, the mammalian cell is a human cell. In certain embodiments, the target antigen is immobilized to a solid support. In certain embodiments, the solid support is a bead. In certain embodiments, the solid support is a column. In certain embodiments, the target antigen is a soluble antigen. In certain embodiments, the target antigen is conjugated to a detectable moiety. In certain embodiments, the detectable moiety is fluorescent. In certain embodiments, the recombinant polypeptide comprises a detectable tag. In certain embodiments, the detectable tag comprises a fluorescent moiety. In certain embodiments, the endogenous T cell activation marker, the second activation marker, and the third activation marker are the same. In certain embodiments, the plurality of cells further comprises a nucleic acid encoding a reporter gene. In certain embodiments, the reporter nucleic acid comprises a reporter gene under the control of an immune cell promoter. In certain embodiments, the reporter gene encodes a fluorescent protein or a luciferase protein. In certain embodiments, the immune cell promoter comprises nuclear factor κB (NFκB) or NFAT or Nuclear factor of activated T-cells (NFAT). In certain embodiments, the second activation marker comprises a reporter nucleic acid. In certain embodiments, the third activation marker comprises a reporter nucleic acid. In certain embodiments, the second activation marker comprises an endogenous marker of T cell activation. In certain embodiments, the third activation marker comprises an endogenous T cell activation marker. In certain embodiments, the endogenous T cell activation marker is selected from CD69, CD25, and a combination thereof. In certain embodiments, the antigen binding domain comprises a single-chain variable fragment (scFv). In certain embodiments, the recombinant polypeptide comprises two or more different antigen binding domains. In certain embodiments, one or more of the two or more different antigen binding domains binds to CD3. In certain embodiments, the recombinant polypeptide comprises a chimeric antigen receptor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates a construct containing a VK domain and VH domain from an anti-CD19 single chain variable fragment (scFv) joined by a GS linker. FIG. 1B illustrates a construct used for creation of a CAR library of constructs containing scFvs from a CD19 antibody library. FIG. 1C illustrates a construct used for creation of a CAR library of constructs containing scFvs from a BCMA antibody library. FIG. 1D illustrates a schematic of a CAR construct as expressed on a cell membrane. FIG. 1D illustrates a schematic of a CAR construct as expressed on a cell membrane. FIG. 1E illustrates the original lentiviral vector pLenti-C-HA-IRES-BSD [OriGene CAT #: PS100104]. FIG. 1F illustrates the pLenti vector modified with a CAR construct, where the HA tag in the original lentiviral vector was replaced by the CAR construct that was incorporated into the multicloning site using EcoRI-NotI enzymes. FIG. 1G illustrates a general construct and expression of the general construct in a cell membrane.

FIG. 2A illustrates a CAR construct containing a VK domain and VH domain from an anti-CD19 single chain variable fragment (scFv) joined by a GS linker. FIG. 2B illustrates a schematic of the CAR construct as expressed on a cell membrane. FIG. 2C illustrates the pLenti vector of FIG. 1E modified with the CAR construct of FIG. 2A, where the HA tag was replaced by the CART construct that was incorporated into the multicloning site using EcoRI-NotI enzymes.

FIG. 3A illustrates CD19-CART-mCherry surface expression on a Jurkat NFκB-Luc reporter cell line. FIG. 3B illustrates CD19-CART-mCherry surface expression on a Jurkat NFκB-GFP reporter cell line. FIG. 3C illustrates fluorescent microscopy of Jurkat cells from FIG. 3A showing mCherry fluorescence on the surface of the cell membrane indicating translocation of the construct to the cell surface. White arrows indicate the surface fluorescence on the surface of the cells.

FIG. 4A illustrates a schematic of a CAR-T activation assay in a cell expressing GFP under control of the NFκB promoter. FIG. 4B illustrates a schematic of a CAR-T activation in a cell expressing firefly luciferase under control of the NFκB promoter. FIG. 4C illustrates a schematic of a CAR-T activation assay in a cell line expressing GFP under control of a target promoter. FIG. 4D illustrates a schematic of a CAR-T activation in a cell expressing firefly luciferase under control of a target promoter. A chimeric antigen receptor (CAR) comprising an antigen binding domain which binds a target antigen can be activated in the presence of the target antigen. The target antigen can be expressed by cells, such as tumor cells or cells transduced with the target antigen. The target antigen can be soluble or bound to a solid support, such as a plate or bead.

FIG. 5A illustrates a method of generating a CART library beginning with generation of CART constructs. FIG. 5B illustrates a method of generating a CART library beginning with an initial antigen panning step prior to viral packaging.

FIG. 7A illustrates Jurkat luciferase NFκB reporter cell lines generated with high CART-19 expression and medium CART-19 expression relative to the parental Jurkat luciferase NFκB reporter cell line. FIG. 7N illustrates CD69 expression in Jurkat NFκB-Luc CART19 high cells incubated with Raji overnight.

FIGS. 9A-9E illustrates expression and co-expression of GFP and CD69 by Jurkat NFκB-GFP CART19 after 6-hour or overnight incubation with Raji cells. FIG. 9A illustrates co-expression of GFP and CD69 by Jurkat NFκB-GFP CART19 after 6-hour incubation with Raji cells. FIG. 9B illustrates expression of GFP and expression of CD69 by Jurkat NFκB-GFP CART19 after 6-hour incubation with Raji cells. FIG. 9C illustrates co-expression of GFP and CD69 by Jurkat NFκB-GFP CART19 after overnight hour incubation with Raji cells. FIG. 9D illustrates expression of GFP and expression of CD69 by Jurkat NFκB-GFP CART19 after overnight hour incubation with Raji cells. FIG. 9E illustrates co-localization of the activated CART19 mCherry and GFP when activated in the presence of Raji cells.

FIGS. 10A-10D illustrates expression and co-expression of GFP and CD69 by Jurkat NFκB-GFP CART19 after 6-hour or overnight incubation with Daudi cells. FIG. 10A illustrates co-expression of GFP and CD69 by Jurkat NFκB-GFP CART19 after 6-hour incubation with Daudi cells. FIG. 10B illustrates expression of GFP and expression of CD69 by Jurkat NFκB-GFP CART19 after 6-hour incubation with Daudi cells. FIG. 10C illustrates co-expression of GFP and CD69 by Jurkat NFκB-GFP CART19 after overnight incubation with Daudi cells. FIG. 10D illustrates expression of GFP and expression of CD69 by Jurkat NFκB-GFP CART19 after overnight incubation with Daudi cells.

FIGS. 11A-11D illustrates expression and co-expression of GFP and CD69 by Jurkat NFκB-GFP CART19 after 6-hour or overnight incubation with K562 cells. FIG. 11A illustrates co-expression of GFP and CD69 by Jurkat NFκB-GFP CART19 after 6-hour incubation with K562cells. FIG. 11B illustrates expression of GFP and expression of CD69 by Jurkat NFκB-GFP CART19 after 6-hour incubation with K562cells. FIG. 11C illustrates co-expression of GFP and CD69 by Jurkat NFκB-GFP CART19 after overnight hour incubation with K562cells. FIG. 11D illustrates expression of GFP and expression of CD69 by Jurkat NFκB-GFP CART19 after overnight hour incubation with K562cells.

FIGS. 12A-12D illustrate a time course of CART19 activation and GFP and CD69 expression. FIG. 12A illustrates Jurkat NFκB-GFP CART19 cells gated after incubation with Raji (violet trace). FIG. 12B illustrates the co-staining of GFP and CD69 of the activated Jurkat NFκB-GFP CART19 cells. The peak of activation is between 6 hours to overnight. FIG. 12C illustrates overlaid histograms of each fluorophore alone: left panel is the increase of mCherry signal over time, middle panel is the increase of CD69 over time, and the right panel is the increase of GFP over time. Data are presented as mean fluorescent intensity (MFI) in the corresponding tables below. FIG. 12D shows microscopy images indicating increase of mCherry signal as punctate clusters on the Jurkat NFκB-GFP CART19 post activation with Raji CD19 cells.

FIG. 14 shows four ScFv clones from each DB-CART-CD19 and DB-CART-BCMA presented as an example for specific activation when either CD19 or BCMA expressing cell lines are cultured with these clones. Data are shown as GFP vs. activation Marker 3 co-expression. When CD19 or BCMA present on tumor cell lines both markers co express indicating activation (upper row). When the same CART clones encounter cell lines that lack the target neither of the markers are expressed (lower row), indicating specific activation of scFv clones generated from our CART libraries.

DETAILED DESCRIPTION

Figures 1A, 1B, 1C:
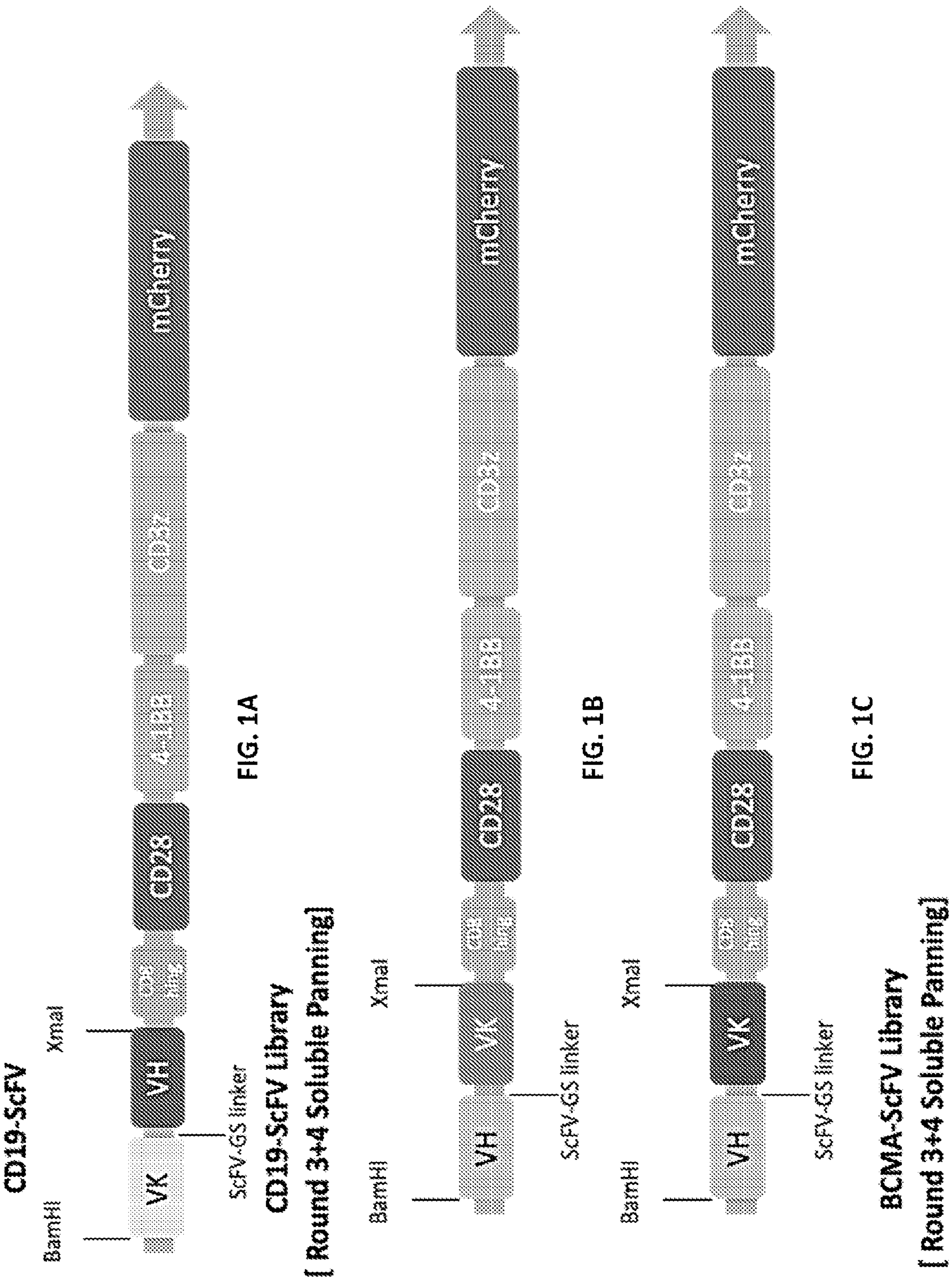
FIGS. 1A-1G illustrate examples of chimeric antigen receptor (CAR) constructs.
Figure 1D:
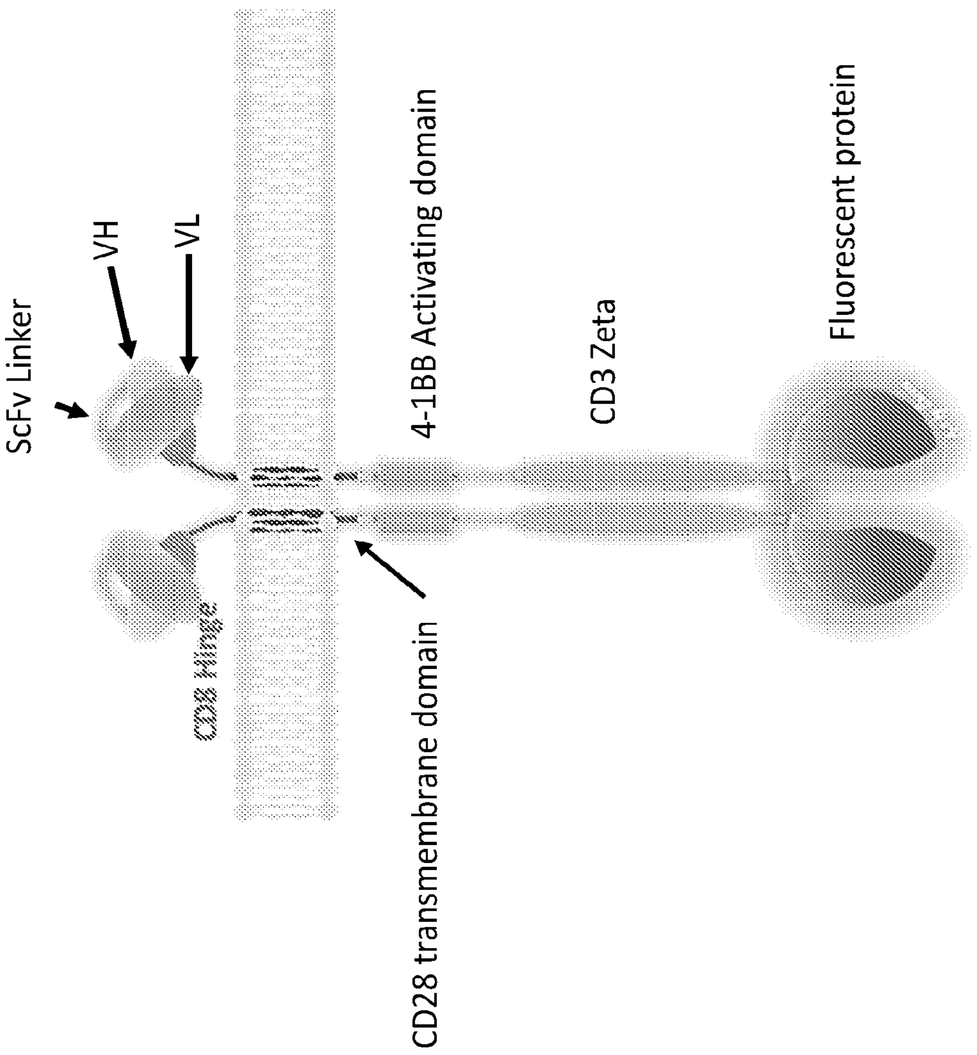
Figure 1E:
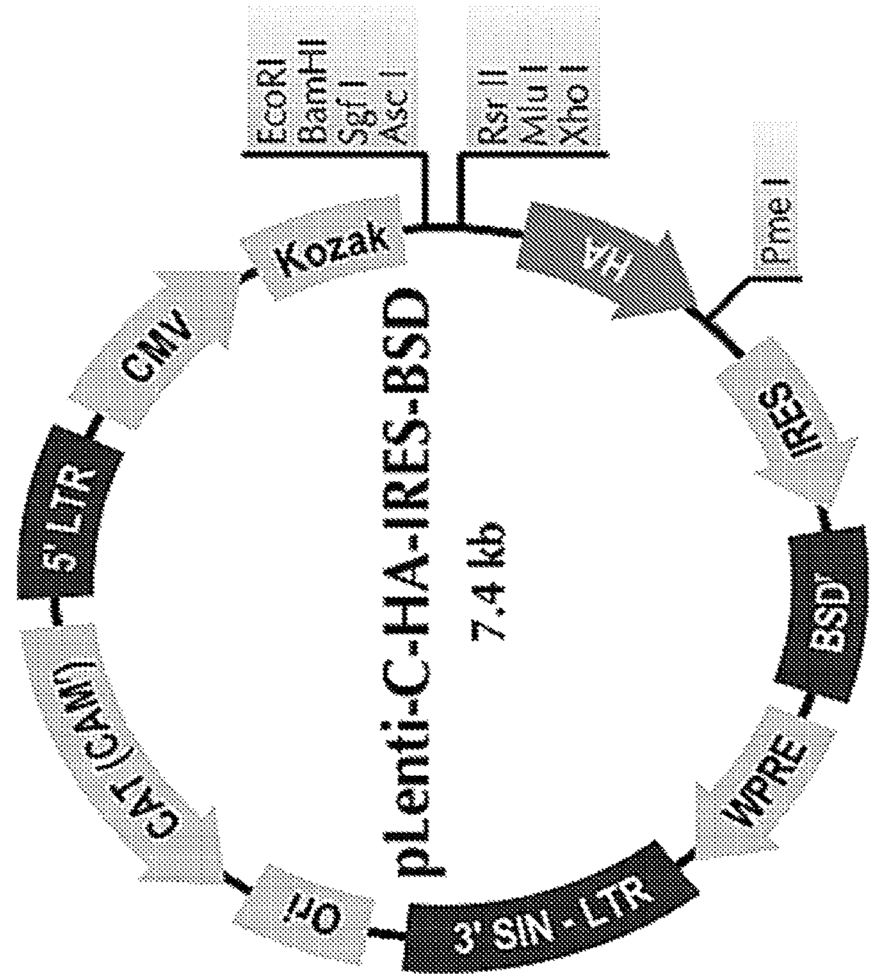
Figure 1F:
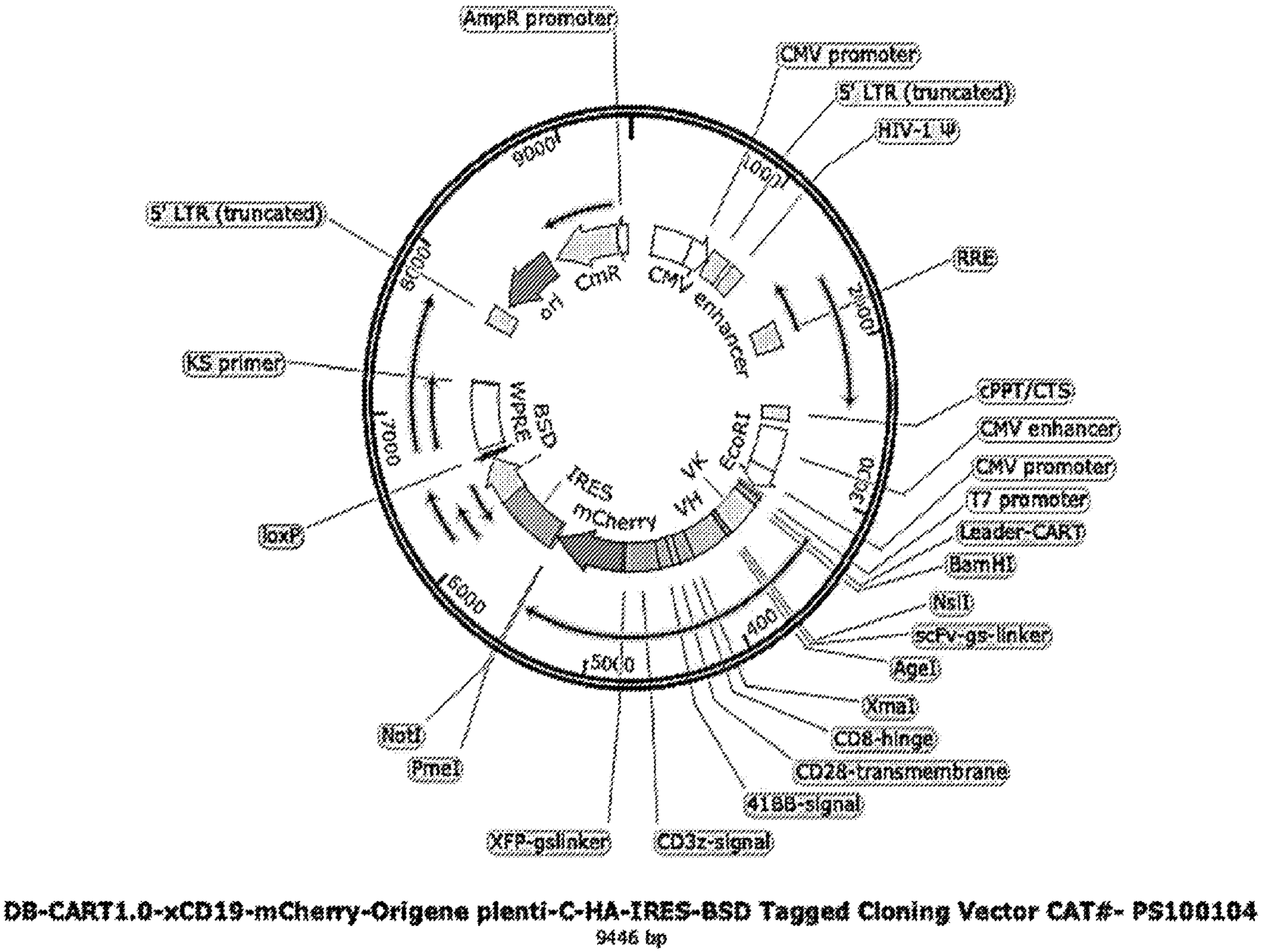
Figure 1G:
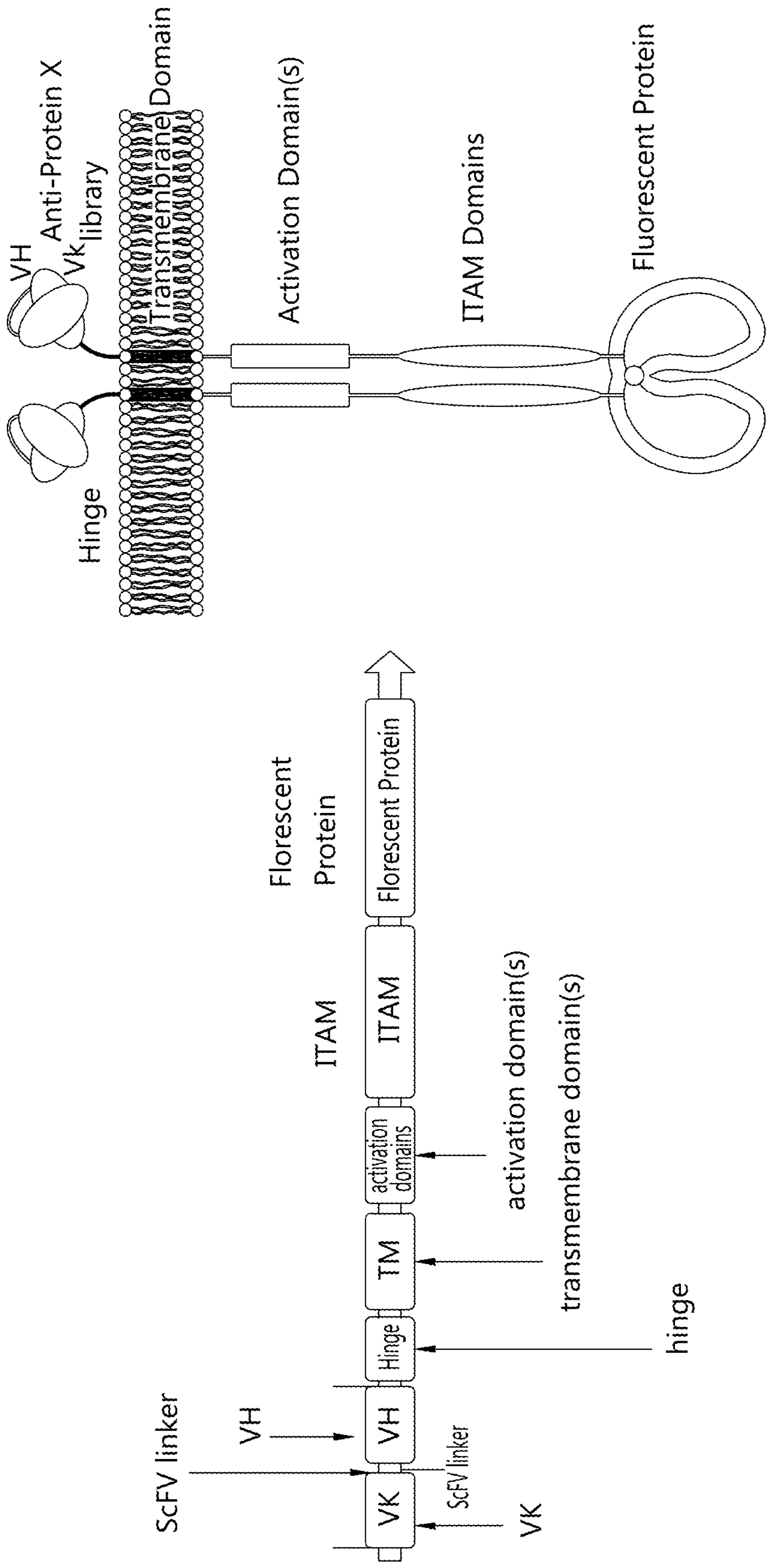
Figure 2A:
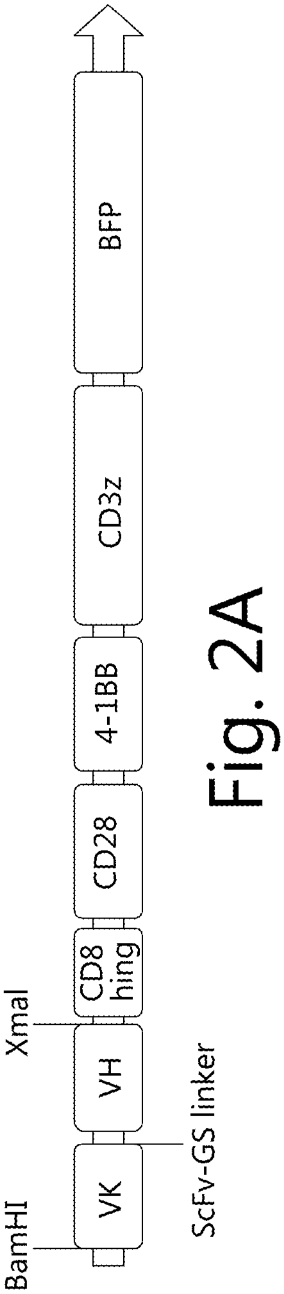
FIGS. 2A-2C illustrate examples of chimeric antigen receptor (CAR) constructs containing a blue fluorescent protein (BFP).
Figure 2B:
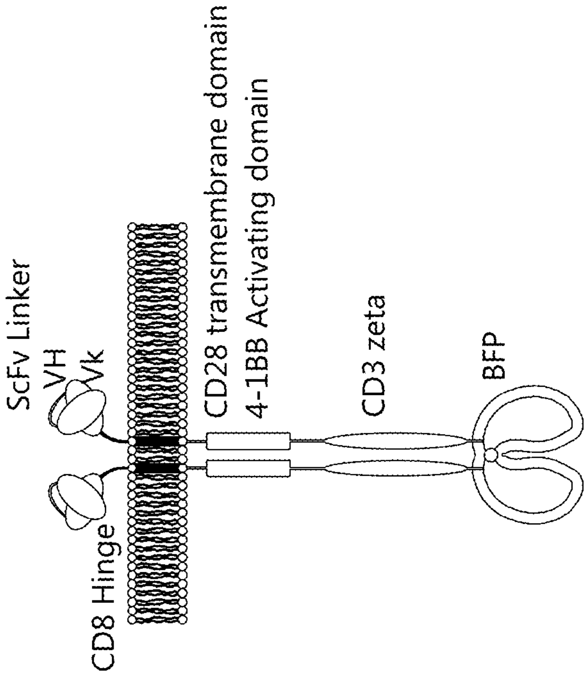
Figure 2C:
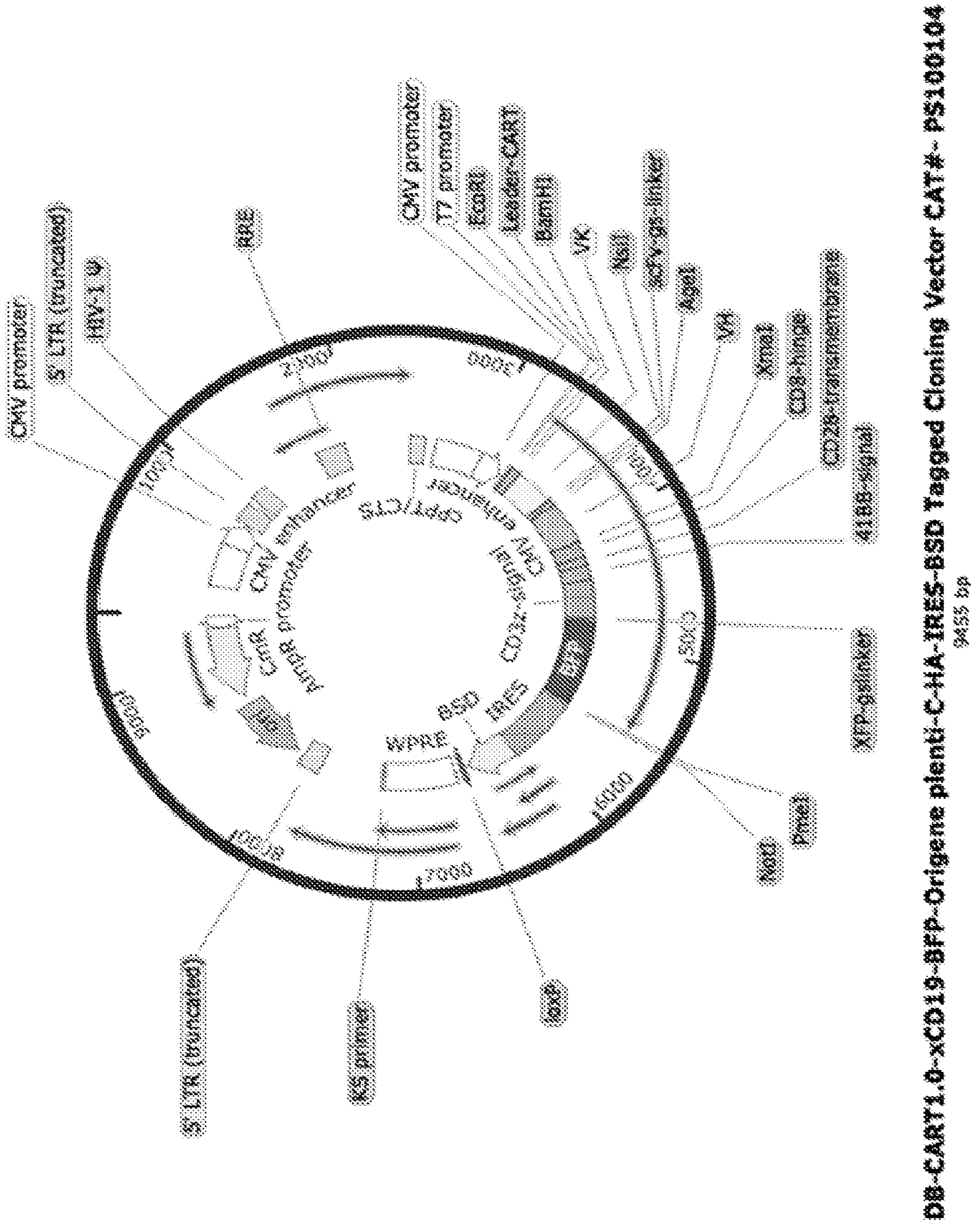

While preferred aspects of the present disclosure have been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the disclosure described herein may be employed in practicing the disclosure. It is intended that the following claims define the scope of the disclosure and that methods and structures within the scope of these claims and their equivalents be covered thereby.

Use of absolute or sequential terms, for example, "will," "will not," "shall," "shall not," "must," "must not," "first," "initially," "next," "subsequently," "before," "after," "lastly," and "finally," are not meant to limit scope of the present aspects disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Any systems, methods, software, and platforms described herein are modular and not limited to sequential steps. Accordingly, terms such as "first" and "second" do not necessarily imply priority, order of importance, or order of acts.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

As used herein, a "cell" generally refers to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens, C. Agardh*, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g., a cell can be a synthetically made, sometimes termed an artificial cell).

The term "library" in conjunction with screening or selecting for cells, nucleic acids, antibodies, chimeric antigen receptors, etc. refers to a plurality of the indicated cells, nucleic acids, antibodies, chimeric antigen receptors, etc., wherein the plurality comprises different chemical entities with respect to the active entity being screened for. For example, a plurality of cells with each cell comprising a chimeric antigen receptor with different antigen specificities, but comprising similar or substantially similar transmembrane or activation domains.

The term "receptor," as used herein, generally refers to a molecule (e.g., a polypeptide) that has an affinity for a given ligand. Receptors can be naturally occurring or synthetic molecules. The given ligand (or ligand) can be naturally occurring or synthetic molecules. Receptors can be employed in an unaltered state or as aggregates with other species (e.g., with one or more co-receptors, one or more adaptors, lipid rafts, etc.). Examples of receptors may include, but are not limited to, cell membrane receptors, soluble receptors, cloned receptors, recombinant receptors, complex carbohydrates and glycoproteins hormone receptors, drug receptors, transmitter receptors, autocoid receptors, cytokine receptors, antibodies, antibody fragments, engineered antibodies, antibody mimics, molecular recognition units, adhesion molecules, agglutinins, integrins, selectins, nucleic acids and synthetic heteropolymers comprising amino acids, nucleotides, carbohydrates or nonbiologic monomers, including analogs and derivatives thereof, and conjugates or complexes formed by attaching or binding any of these molecules to a second molecule.

The term "antigen," as used herein, generally refers to a molecule or a fragment thereof (e.g., ligand) capable of being bound by a selective binding agent. As an example, an antigen can be a ligand that can be bound by a selective binding agent such as a receptor. As another example, an antigen can be an antigenic molecule that can be bound by a selective binding agent such as an immunological protein (e.g., an antibody). An antigen can also refer to a molecule or fragment thereof capable of being used in an animal to produce antibodies capable of binding to that antigen.

The term "antibody," as used herein, generally refers to a proteinaceous binding molecule with immunoglobulin-like functions. The term antibody includes antibodies (e.g., monoclonal and polyclonal antibodies), as well as variants thereof. Antibodies include, but are not limited to, immunoglobulins (Ig's) of different classes (i.e., IgA, IgG, IgM, IgD and IgE) and subclasses (such as IgG1, IgG2, etc.). A variant can refer to a functional derivative or fragment which retains the binding specificity (e.g., complete and/or partial) of the corresponding antibody. Antigen-binding fragments include Fab, Fab', F(ab')2, variable fragment (Fv), single chain variable fragment (scFv), minibodies, diabodies, and single-domain antibodies ("sdAb" or "nanobodies" or "camelids"). The term antibody includes antibodies and antigen-binding fragments of antibodies that have been optimized, engineered or chemically conjugated. Examples of antibodies that have been optimized include affinity-matured antibodies. Examples of antibodies that have been engineered include Fc optimized antibodies (e.g., antibodies optimized in the fragment crystallizable region) and multi-specific antibodies (e.g., bispecific antibodies).

The terms "Fc receptor" or "FcR," as used herein, generally refers to a receptor, or any variant thereof, that can bind to the Fc region of an antibody. In certain embodiments, the FcR is one which binds an IgG antibody (a gamma receptor, Fcgamma R) and includes receptors of the Fcgamma RI (CD64), Fcgamma RII (CD32), and Fcgamma RIII (CD16) subclasses, including allelic variants and alternatively spliced forms of these receptors. Fcgamma RII receptors include Fcgamma RIIA (an "activating receptor") and Fcgamma RIIB (an "inhibiting receptor"), which have similar amino acid sequences that differ primarily in the cytoplasmic domains thereof. The term "FcR" also includes the neonatal receptor, FcRn, which is responsible for the transfer of maternal IgGs to the fetus.

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif.; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three-dimensional structure, and can perform any function, known or unknown. A polynucleotide can comprise one or more analogs (e.g., altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The term "expression" generally refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides can be collectively referred to as "gene product." If the polynucleotide is derived from genomic DNA, expression can include splicing of the mRNA in a eukaryotic cell. "Up-regulated," with reference to expression, generally refers to an increased expression level of a polynucleotide (e.g., RNA such as mRNA) and/or polypeptide sequence relative to its expression level in a wild-type state while "down-regulated" generally refers to a decreased expression level of a polynucleotide (e.g., RNA such as mRNA) and/or polypeptide sequence relative to its expression in a wild-type state.

The term "2A peptide" may generally refer to a class of viral oligopeptides (e.g., 18-22 amino-acid (aa)-long viral oligopeptides) that mediate "cleavage" of polypeptides during translation in cells (e.g., eukaryotic cells). The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (*Thosea asigna* virus 2A) were also identified. The mechanism of 2A-mediated "self-cleavage" is believed to be ribosome skipping the formation of a glycyl-prolyl peptide bond at the C-terminus of the 2A sequence.

Described herein is a method of screening a library of cells comprising: (a) contacting a plurality of cells with a target antigen; the plurality of cells comprising a recombinant polypeptide comprising an antigen binding domain, a transmembrane domain, an activation domain or an inhibition domain, wherein the antigen binding domain differs among the plurality of cells; (b) selecting cells that display specificity for the target antigen, thereby producing a first subset of antigen binding cells; (c) contacting the first subset of cells with a plurality of cells not expressing the target antigen; and (d) selecting cells of the first subset of antigen binding cells that do not display expression of a first activation marker, thereby producing a subset of low-background binding cells. In certain embodiments, the method further comprises contacting the subset of low-background binding cells to the target antigen and selecting cells from the low-background, activated cells that display activation of the reporter nucleic acid, a second activation marker, or a third activation marker, thereby producing a subset of high antigen binding, low background binding activated cells.

The recombinant polypeptides described herein are in some embodiments, chimeric antigen receptor constructs (the nucleic acid sequence of a non-limiting example of a CAR with a detectable label is shown in SEQ ID NO: 1). In other embodiments, the recombinant polypeptide comprises a bispecific antigen binding domain with the ability to bind to two separate epitopes. In certain embodiments, one of the epitopes is an epitope of CD3. The recombinant polypeptides described herein may further comprise a detectable tag. Such a tag allows for verification of cells that productively express the recombinant polypeptide. The detectable tag may comprise a fluorescent molecule such as GFP, EGFP, YFP, RFP, CFP, or other molecules that are commonly used to track protein production or movement. The recombinant polypeptide may be under the control of a constitutive promoter (e.g., CMV). The recombinant polypeptide may be under the control of an inducible or repressible promoter (e.g., Tet-On or Tet-Off systems).

The methods described herein may further comprise a step of transfecting a nucleic acid or library of nucleic acids encoding the recombinant polypeptide into a cell or a plurality of cells. This transfection or transduction step may be achieved by commonly used techniques such as viral transduction, cationic lipid-based transfection, or electroporation. The methods described herein may further comprise selecting cells that have been transfected or transduced based on a detectable tag for further analysis or to subject to the screening methods described herein. In certain embodiments, the nucleic acid encoding the recombinant polypeptide may be stably integrated into the genome of the cell either in a random fashion or targeted to a safe-harbor locus, such as AAVS1, using for example, CRISPR or homologous recombination. A plurality of cells selected for expression of the recombinant polypeptide may be used immediately in the screening methods described herein or frozen with a compatible cryoprotectant and stored in liquid nitrogen. Cells transfected or transduced may cultured to allow expression of the recombinant polypeptide for 12, 24, 48, or 72 hours or more.

In certain embodiments, the cell or cell population used in the screening method either that expresses the recombinant polypeptide or the target antigen is a eukaryotic cell. In certain embodiments, the cell or cell population is a mammalian cell. In certain embodiments, the cell or cell population is a human cell. In certain embodiments, the cell or cell population is SH-SY5Y, Human neuroblastoma; Hep G2, Human Caucasian hepatocyte carcinoma; 293 (also known as HEK 293), Human Embryo Kidney; RAW 264.7, Mouse monocyte macrophage; HeLa, Human cervix epitheloid carcinoma; MRC-5 (PD 19), Human fetal lung; A2780, Human ovarian carcinoma; CACO-2, Human Caucasian colon adenocarcinoma; THP 1, Human monocytic leukemia; A549, Human Caucasian lung carcinoma; MRC-5 (PD 30), Human fetal lung; MCF7, Human Caucasian breast adenocarcinoma; SNL 76/7, Mouse SIM strain embryonic fibroblast; C2C12, Mouse C3H muscle myoblast; Jurkat E6.1, Human leukemic T cell lymphoblast; U937, Human Caucasian histiocytic lymphoma; L929, Mouse C3H/An connective tissue; 3T3 L1, Mouse Embryo; HL60, Human Caucasian promyelocytic leukaemia; PC-12, Rat adrenal phaeochromocytoma; HT29, Human Caucasian colon adenocarcinoma; OE33, Human Caucasian oesophageal carcinoma; OE19, Human Caucasian oesophageal carcinoma; NIH 3T3, Mouse Swiss NIH embryo; MDA-MB-231, Human Caucasian breast adenocarcinoma; K562, Human Caucasian chronic myelogenous leukemia; U-87 MG, Human glioblastoma astrocytoma; MRC-5 (PD 25), Human fetal lung; A2780cis, Human ovarian carcinoma; B9, Mouse B cell hybridoma; CHO-K1, Hamster Chinese ovary; MDCK, Canine Cocker Spaniel kidney; 1321N1, Human brain astrocytoma; A431, Human squamous carcinoma; ATDC5, Mouse 129 teratocarcinoma AT805 derived; RCC4 PLUS VECTOR ALONE, Renal cell carcinoma cell line RCC4 stably transfected with an empty expression vector, pcDNA3, conferring neomycin resistance.; HUVEC (S200-05n), Human Pre-screened Umbilical Vein Endothelial Cells (HUVEC); neonatal; Vero, Monkey African Green kidney; RCC4 PLUS VHL, Renal cell carcinoma cell line RCC4 stably transfected with pcDNA3-VHL; Fao, Rat hepatoma; J774A.1, Mouse BALB/c monocyte macrophage; MC3T3-E1, Mouse C57BL/6 calvaria; J774.2, Mouse BALB/c monocyte macrophage; PNT1A, Human post pubertal prostate normal, immortalised with SV40; U-2 OS, Human Osteosarcoma; HCT 116, Human colon carcinoma; MA104, Monkey African Green kidney; BEAS-2B, Human bronchial epithelium, normal; NB2-11, Rat lymphoma; BHK 21 (clone 13), Hamster Syrian kidney; NSO, Mouse myeloma; Neuro 2a, Mouse Albino neuroblastoma; SP2/0-Ag14, Mouse x Mouse myeloma, non-producing; T47D, Human breast tumor; 1301, Human T-cell leukemia; MDCK-II, Canine Cocker Spaniel Kidney; PNT2, Human prostate normal, immortalized with SV40; PC-3, Human Caucasian prostate adenocarcinoma; TF1, Human erythroleukaemia; COS-7, Monkey African green kidney, SV40 transformed; MDCK, Canine Cocker Spaniel kidney; HUVEC (200-05n), Human Umbilical Vein Endothelial Cells (HUVEC); neonatal; NCI-H322, Human Caucasian bronchioalveolar carcinoma; SK.N.SH, Human Caucasian neuroblastoma; LNCaP.FGC, Human Caucasian prostate carcinoma; OE21, Human Caucasian oesophageal squamous cell carcinoma; PSN1, Human pancreatic adenocarcinoma; ISHIKAWA, Human Asian endometrial adenocarcinoma; MFE-280, Human Caucasian endometrial adenocarcinoma; MG-63, Human osteosarcoma; RK 13, Rabbit kidney, BVDV negative; EoL-1 cell, Human eosinophilic leukemia; VCaP, Human Prostate Cancer Metastasis; tsA201, Human embryonal kidney, SV40 transformed; CHO, Hamster Chinese ovary; HT 1080, Human fibrosarcoma; PANC-1, Human Caucasian pancreas; Saos-2, Human primary osteogenic sarcoma; Fibroblast Growth Medium (116K-500), Fibroblast Growth Medium Kit; ND7/23, Mouse neuroblastoma x Rat neuron hybrid; SK-OV-3, Human Caucasian ovary adenocarcinoma; COV434, Human ovarian granulosa tumor; Hep 3B, Human hepatocyte carcinoma; Vero (WHO), Monkey African Green kidney; Nthy-ori 3-1, Human thyroid follicular epithelial; U373 MG (Uppsala), Human glioblastoma astrocytoma; A375, Human malignant melanoma; AGS, Human Caucasian gastric adenocarcinoma; CAKI 2, Human Caucasian kidney carcinoma; COLO 205, Human Caucasian colon adenocarcinoma; COR-L23, Human Caucasian lung large cell carcinoma; IMR 32, Human Caucasian neuroblastoma; QT 35, Quail Japanese fibrosarcoma; WI 38, Human Caucasian fetal lung; HMVII, Human vaginal malignant melanoma; HT55, Human colon carcinoma; TK6, Human lymphoblast, thymidine kinase heterozygote; SP2/0-AG14 (AC-FREE), Mouse x mouse hybridoma non-secreting, serum-free, animal component (AC) free; AR42J, or Rat exocrine pancreatic tumor, DAUDI cells or RAJI cells, or any combination thereof. In certain embodiments, the target antigen is expressed by a monocyte cell line, a B cell line or a T cell line. In certain embodiments, the cell that expressed the recombinant polypeptide is a JURKAT cell.

Cells that have been transduced or transfected with the recombinant polypeptide are subjected to a selection based on contacting the cells to a target antigen. In certain embodiments, target antigen is a tumor associated-antigens. In certain embodiments, target antigens are human tumor associated antigens or viral antigens associated with cancer (e.g., HPV E6 or HPV E7). In certain embodiments, the tumor associated antigen comprises CD19. In certain embodiments, the tumor associated antigen comprises CD20, Mucin-1, CD22; RORI; mesothelin; CD33/IL3Ra; c-Met; PSMA; Glycolipid F77; EGFRvIII; GD-2; NY-ESO-1; MAGE A3, CEA, CA-125, HPV-E6, HPV-E7, or any combination thereof.

In certain embodiments, the target antigen is expressed by a cell or cell line. In certain embodiments, the target antigen is soluble antigen such as the native antigen in soluble form or a soluble portion of the antigen, or a soluble portion of the antigen fused to a polypeptide (e.g., an IgG Fc region). In certain embodiments, the target antigen is conjugated to a solid support such as a column, a bead, or agarose. Such conjugation allows for the selection and retention of cells expressing a recombinant polypeptide with a desired binding specificity. Cells may also be selected based upon binding to a fluorescently labeled antigen using methods such as flow cytometry.

In other embodiments, cells may be selected based upon activation of reporter gene contained on a reporter nucleic acid. The reporter nucleic acid minimally comprises a regulatory element that is able to be bound by a transcription factor and a nucleotide sequence encoding a reporter. Said nucleotide sequence encoding a reporter is downstream of said regulatory element that is able to be bound by said transcription factor. The transcription factor may be a synthetic transcription factor, a transcription factor heterologous to the cell, or a transcription factor endogenous to the cell, such as NFAT or NF-kB In certain embodiments, the nucleotide sequence encoding a reporter comprises a reporter gene. In certain embodiments, said reporter gene encodes a reporter selected from a fluorescent protein, a luciferase protein, a beta-galactosidase, a beta-glucuronidase, a chloramphenicol acetyltransferase, and a secreted placental alkaline phosphatase. These reporter proteins can be assayed for a specific enzymatic activity or in the case of a fluorescent reporter can be assayed for fluorescent emissions. In certain embodiments, the fluorescent protein comprises a green fluorescent protein (GFP), a red fluorescent protein (RFP), a yellow fluorescent protein (YFP), or a cyan fluorescent protein (CFP).

In certain embodiments, the nucleotide sequence encoding a reporter gene comprises a nucleotide sequence encoding a unique sequence identifier (UMI). In certain embodiments, said UMI is unique to a test polypeptide, wherein said test polypeptide is encoded by said reporter nucleic acid. Generally, said UMI will be between 8 and 20 nucleotides in length, however it may be longer. In certain embodiments, said UMI is 8, 9, 10, 11, 12, 13, 14, 15, 16, 17, 18, 19, 20, or more nucleotides in length. In certain embodiments, said UMI is 8 nucleotides in length. In certain embodiments, said UMI is 9 nucleotides in length. In certain embodiments, said UMI is 10 nucleotides in length. In certain embodiments, said UMI is 11 nucleotides in length. In certain embodiments, said UMI is 12 nucleotides in length. In certain embodiments, said UMI is 13 nucleotides in length. In certain embodiments, said UMI is 14 nucleotides in length. In certain embodiments, said UMI is 15 nucleotides in length. In certain embodiments, said UMI is 16 nucleotides in length. In certain embodiments, said UMI is 17 nucleotides in length. In certain embodiments, said UMI is 18 nucleotides in length. In certain embodiments, said UMI is 19 nucleotides in length. In certain embodiments, said UMI is 20 nucleotides in length. In certain embodiments, said UMI is more than 20 nucleotides in length.

In other embodiments, cells may be selected based upon activation of an endogenous activation marker. In certain embodiments, the endogenous activation marker is an immune cell activation marker. In certain embodiments, the activation marker is a T cell activation marker. In certain embodiments, the endogenous T cell activation marker is CD69, CD25 or a combination thereof of. Expression of such endogenous activation markers can be achieved using detectably labeled antibodies specific for the endogenous activation marker.

Following selection of cells that exhibit binding to target antigen the cells are then subjected to another round of selection that allows discrimination of cells expressing recombinant polypeptides that bind promiscuously to antigens that are not the target antigen. In certain embodiments, a first subset of antigen binding cells is subjected to a selection based upon an activation marker, such as a reporter or an endogenous activation marker to obtain a subset of low-background binding cells. In certain embodiments, low background binding cells are those that exhibit activation in the lowest 50%, 40%, 30%, 25%, 20%, 15%, 10%, 5%, 2%, or 1% percentile of cells of the first subset of antigen binding cells. In certain embodiments, selection is based on a difference between activation markers observed in a first step that selects for a first subset of activated cells and a second step that selects for low-background binding cells. In certain embodiments, the low-background binding cells exhibit 2-fold, 3-fold, 4-fold, 5-fold, 7-fold, 10-fold or lower activation when compared to a first subset of activated cells. In certain embodiments, low-background binding cells are those that express levels of activation comparable to cells that are not contacted to cells expressing target antigen. In certain embodiments, low-background binding cells are those that express levels of activation less than 50%, 40%, 30%, 25%, 20%, 10%, 5% or less compared to control cells that are not contacted to cells expressing target antigen.

The methods described herein comprise a step of determining cells expressing recombinant polypeptides that exhibit target antigen binding, then determining cells that do not exhibit binding to other antigens, and optionally a step of determining cells that exhibit high target antigen binding from the cells that exhibit no or low background binding to other antigens. These methods require assessing detectable readouts that reflect target antigen binding. Since there is no dependence on a particular modality of readout, the readouts at each discreet step may be the same or the readouts nay be different. The readouts at the separate steps may be different reporters or endogenous activation markers. For a step that selects for antigen binding the readout may be collecting cells enriched after binding to a target antigen immobilized (covalently or non-covalently) to a solid support.

The selection steps described herein can be repeated 1, 2, 3, 4 times or more.

Figure 13:
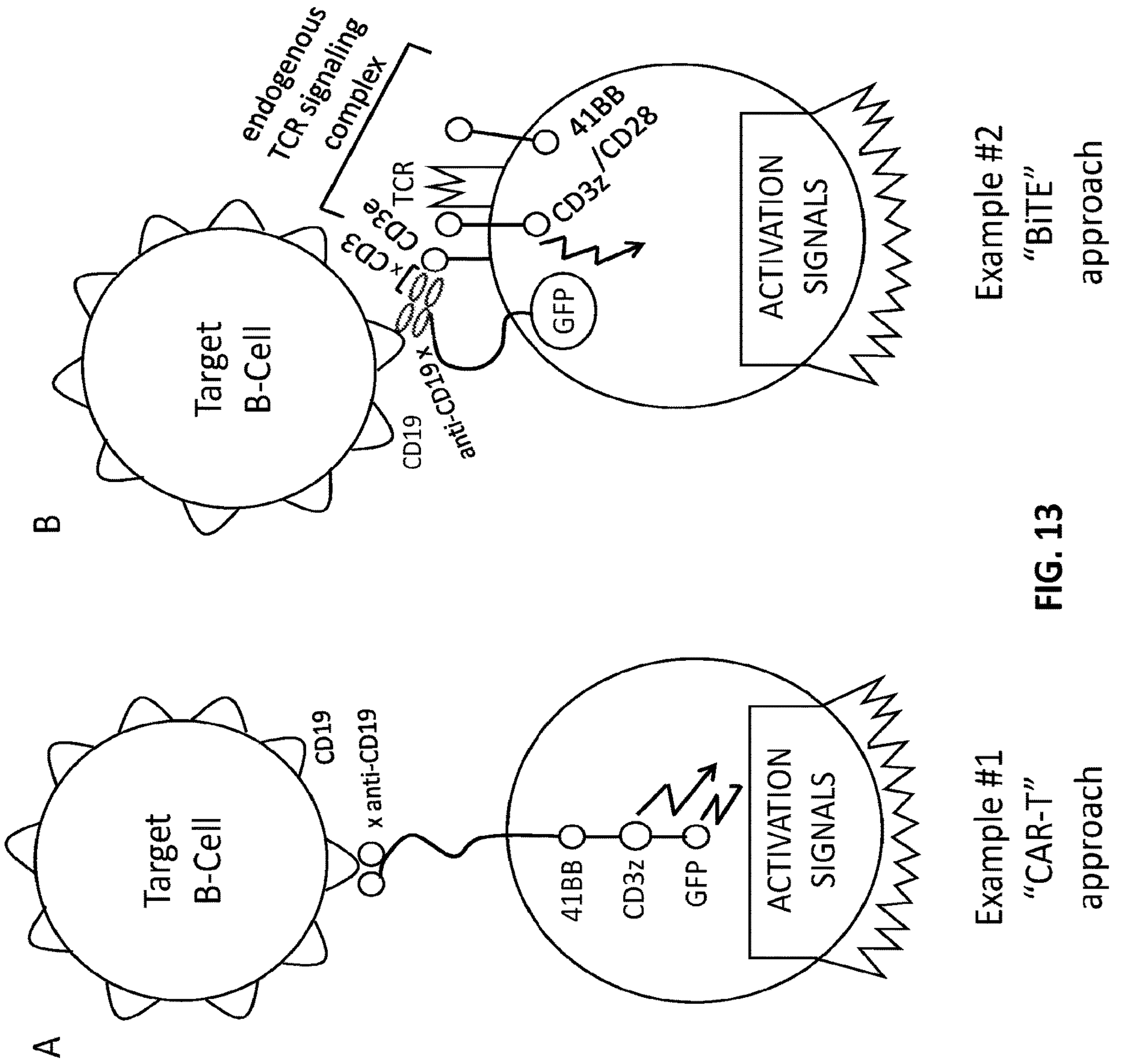
FIG. 13 illustrates mechanisms for inducing signaling in a cell.

Methods of generating a library of cells expressing a plurality of polypeptides or recombinant polypeptides are provided herein. In some embodiments, the polypeptide may include a target-specificity domain (e.g., an anti-CD19), a hinge (e.g., a CD8 hinge or any suitable polypeptide), a transmembrane domain (TMD) (e.g., a CD28 TMD or any suitable TMD), and/or an element for inducing signaling in a cell. FIG. 13 illustrates at least two mechanisms for inducing signaling in a cell. With reference to panel A of FIG. 13, a "CAR-T" approach or method is shown. In the CAR-T approach, signaling is induced in a cell by adding one or more signaling domains (e.g., CD3 zeta, 41BB, etc.) intracellularly. With reference to panel B of FIG. 13, a "BiTE" approach or method is shown. In the BiTE approach, signaling is induced in a cell by adding a binding domain that can associate or operatively couple the polypeptide to an endogenous signaling complex (e.g., "tethered BiTE" technology).

In various embodiments, the polypeptide may include a signaling domain (e.g., GFP, mCherry, BFP, etc.). Such a signaling domain can aid in making or generating a controlled library with only one member per cell. Such a signaling domain can also provide the ability to track the behavior of the polypeptide.

Methods of panning or screening a library of cells comprising a plurality of polypeptides or recombinant polypeptides for specificity against a target antigen are also provided herein. The method of panning can include "conditional panning." For example, the conditional panning may include: 1) adding or removing a substance to the cells in media, 2) exposing the cells to the target, and 3) sorting activated and non-activated cells. Conditional panning can be used to find or identify binders that are: 1) conditionally activated in the presence of a small molecule (e.g., aspirin) and/or 2) conditionally inactivated in the presence of a substance (e.g., CAR-Ts that do not activate in cerebrospinal fluid and therefore may protect the brain from the CAR-T neurotoxicity). Conditional panning can be used to find or identify other types of binders as described and/or claimed herein.

An aspect of the present disclosure is directed to generation of one or more libraries. A method of generating a library can include generating a library of cells expressing a plurality of recombinant polypeptides.

The conditional panning can occur during any panning round, either a selection or a deselection round. In conditional panning, something is added to or removed from the media that contains the cells. Sorting the activating and non-activating cells is then conducted. This approach can be used to identify clones that activate only when the "conditional" molecule is present or absent. For example, aspirin can be added to the media during deselection and any clones that might activate spontaneously around aspirin can be removed. In another example, cerebrospinal fluid can be added to the media during selection and clones that do not activate in cerebrospinal fluid, but otherwise do activate, can be sorted out.

In some embodiments, the method may comprise panning of a target antigen against an antibody library. Panning of the target antigen against an antibody library can thereby generate a plurality of antibody candidates from the antibody library. The plurality of antibody candidates can be any antibody from the antibody library showing affinity to the target antigen after the panning. The panning can comprise at least 1 round, 2 rounds, 3 rounds, 4 rounds, or more than 4 rounds of panning.

Antibody libraries described herein can comprise a plurality of antibodies wherein each antibody of the plurality of antibodies comprises: (a) a VH domain comprising a VH-CDR1 sequence, a VH-CDR2 sequence, and a VH-CDR3 sequence; and (b) a VL domain comprising a VL-CDR1 sequence, a VL-CDR2 sequence, and a VL-CDR3 sequence; wherein (a) at least one of the VH-CDR3 sequence and the VL-CDR3 sequence is derived from a naïve B-cell; (b) if only one of the VH-CDR3 and VL-CDR3 is derived from the naïve B-cell, then the VH-CDR3 or VL-CDR3 not derived from the naïve B-cell is derived from a memory cell; and (c) the VH-CDR1 sequence, VH-CDR2 sequence, VL-CDR1 sequence, and VL-CDR2 sequence are derived from a memory cell. In some embodiments, the antibody library is any suitable antibody library. The antibody library can be an antibody library comprising high functional diversity as described herein, such as a SuperHuman Library.

Antibodies can be synthesized by a B-cell in vivo. Antibody isotypes synthesized by B-cells include, but are not limited to, IgA, IgD, IgE, IgG, and IgM. A B-cell which has not yet encountered an antigen can be termed a naïve B-cell, while B-cells which have encountered and been activated by an antigen can be termed a memory B-cell. Naïve B-cells can express IgM, IgD, or a combination thereof. Memory B-cells can express IgE, IgA, IgG, IgM, or a combination thereof. The IgA can be IgA1 or IgA2. The IgG can be IgG1, IgG2, IgG3, or IgG4. The memory B-cell can be a class switched memory B-cell or a non-switched or marginal zone memory B-cell. The non-switched or marginal zone memory B-cell can express IgM.

A complementarity determining region ("CDR") is a part of an immunoglobulin (antibody) variable region that can be responsible for the antigen binding specificity of the antibody. A heavy chain (HC) variable region can comprise three CDR regions, abbreviated VH-CDR1, VH-CDR2, and VH-CDR3 and found in this order on the heavy chain from the N terminus to the C terminus; and a light chain (LC) variable region can comprise three CDR regions, abbreviated VL-CDR1, VL-CDR2, and VL-CDR3 and found in this order on the light chain from the N terminus to the C terminus. Further, the light chain can be a kappa chain (VK) or a lambda chain (Vλ). Surrounding and interspersed between the CDRs are framework regions which can contribute to the structure and can display less variability than the CDR regions.

A heavy chain variable region can comprise four framework regions, abbreviated VH-FR1, VH-FR2, VH-FR3, and VH-FR4. The heavy chain can comprise, from N to C terminus: VH-FR1::VH-CDR1::VH-FR2::VH-CDR2::VH-FR3::VH-CDR3::VH-FR4. A light chain variable region can comprise four framework regions, abbreviated VL-FR1, VL-FR2, VL-FR3, and VL-FR4. The light chain can comprise, from N to C terminus: VL-FR1::VL-CDR1::VL-FR2::VL-CDR2::VL-FR3::VL-CDR3::VL-FR4. In some cases, "CDR sequence" as used herein, refers to a CDR sequence selected from the group consisting of: VH-CDR1, VH-CDR2, VH-CDR3, VL-CDR1, VL-CDR2, VL-CDR3, and any combination thereof. The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme); MacCallum et al., J. *Mol. Biol.* 262:732-745 (1996), "Antibody-antigen interactions: Contact analysis and binding site topography," *J Mol. Biol.* 262, 732-745." ("Contact" numbering scheme); Lefranc MP et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 June 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

In some cases, the plurality of antibodies in the antibody library has high functional diversity. An antibody library with high functional diversity can comprise a plurality of antibodies wherein at least 80%, 85%, 90%, 95%, or 99% of the plurality of antibodies are functional. Functional antibodies can be antibodies with the ability to bind to a protein. The ability of an antibody to bind to a protein can be determined by screening the antibody against protein A or protein L. The antibody library can comprise at least $1.0\times10^5$, $2.0\times10^5$, $3.0\times10^5$, $4.0\times10^5$, $5.0\times10^5$, $6.0\times10^5$, $7.0\times10^5$, $8.0\times10^5$, $9.0\times10^5$, $1.0\times10^{10}$, $2.0\times10^{10}$, $3.0\times10^{10}$, $4.0\times10^{10}$, $5.0\times10^{10}$, $6.0\times10^{10}$, $7.0\times10^{10}$, $8.0\times10^{10}$, or $9.0\times10^{10}$ antibodies. In some embodiments, an antibody library comprising high functional diversity is a SuperHuman Library.

The antibodies of the library can comprise non-naturally occurring combinations of naturally occurring CDRs, such as combinations of CDRs derived from naturally occurring memory B-cells and naïve B-cells, but whose joint appearance on the same antibody would not be naturally occurring. For example, a non-naturally occurring combination of naturally occurring CDRs can comprise at least one CDR derived from a naïve cell while the remaining CDRs can be derived from a memory cell. For example, a non-naturally occurring combination of naturally occurring CDRs can comprise at least one CDR derived from cells of predominantly naïve B-cell origin while the remaining CDRs can be derived from cells of predominantly memory B-cell origin. Naturally occurring CDRs can refer to CDRs naturally occurring in a human population.

The non-naturally occurring combination of naturally occurring CDRs can comprise at least one CDR derived from a naïve cell, while the remaining CDRs are derived from a memory cell. In some cases, at least VL-CDR1 is derived from a naïve cell. In some cases, at least VL-CDR2 is derived from a naïve cell. In some cases, at least VL-CDR3 is derived from a naïve cell. In some cases, at least VH-CDR1 is derived from a naïve cell. In some cases, at least VH-CDR2 is derived from a naïve cell. In some cases, at least VH-CDR3 is derived from a naïve cell.

The non-naturally occurring combination of naturally occurring CDRs can comprise two, three, four, or five CDRs derived from a naïve cell, while the remaining CDRs can be derived from a memory cell. For example, two CDRs from CDRs in the group consisting of: VL-CDR1, VL-CDR2, VL-CDR3, VH-CDR1, VH-CDR2, and VH-CDR3 can be derived from a naïve cell while the remaining CDRs can be derived from a memory cell. In another example, three CDRs from CDRs in the group consisting of: VL-CDR1, VL-CDR2, VL-CDR3, VH-CDR1, VH-CDR2, and VH-CDR3 can be derived from a naïve cell while the remaining CDRs can be derived from a memory cell. In another example, four CDRs from CDRs in the group consisting of: VL-CDR1, VL-CDR2, VL-CDR3, VH-CDR1, VH-CDR2, and VH-CDR3 can be derived from a naïve cell while the remaining CDRs can be derived from a memory cell. In another example, five CDRs from CDRs in the group consisting of: VL-CDR1, VL-CDR2, VL-CDR3, VH-CDR1, VH-CDR2, and VH-CDR3 can be derived from a naïve cell while the remaining CDR can be derived from a memory cell.

In another non-limiting example of a non-naturally occurring combination, VL-CDR3 can be derived from a naïve cell, while VH-CDR1, VH-CDR2, VH-CDR3, VL-CDR1, and VL-CDR2 can be derived from a memory cell. In another non-limiting example of a non-naturally occurring combination, VH-CDR3 can be derived from a naïve cell, while VH-CDR1, VH-CDR2, VL-CDR1, VL-CDR2, and VL-CDR3 can be derived from a memory cell. In another non-limiting example of a non-naturally occurring combination, VH-CDR3 and VL-CDR3 can be derived from a naïve cell, while VH-CDR1, VH-CDR2, VL-CDR1, and VL-CDR2 can be derived from a memory cell.

"Derived," when used in reference to a sequence, can refer to any CDR sequence with sequence homology to a naturally occurring CDR sequence of at least 80%, at least 85%, at least 90%, at least 95%, at least 99%, or 100%. "Derived" can refer to any CDR sequence obtained from sequencing information obtained from a pool of cells of predominantly naïve B-cell origin or a pool of cells of predominantly memory B-cell origin. For instance, a sequence is "derived" from a cell if (1) a sequence was observed in the cell and (2) the same sequence (or a sequence having at least 80%, at least 85%, at least 90%, at least 95%, at least 99% or at least 100% sequence homology to the sequence) is chemically synthesized based on the observed sequence.

In some embodiments, the method may include obtaining a plurality of vectors, wherein each vector in the plurality of vectors encodes a recombinant polypeptide. The polypeptide may include (i) an antigen binding domain; (ii) a hinge domain; (iii) a transmembrane domain; (iv) the ability to activate or inhibit a cell; and/or (v) a first detectable marker (e.g., an optically detectable marker). The antigen binding domain of each vector in the plurality of vectors can be a different antigen binding domain. The antigen binding domain can comprise an antibody or an antigen binding fragment thereof from the plurality of antibody candidates. In some embodiments, the antigen binding domain is an antibody from an antibody library or a fragment thereof. The antibody library can be any antibody library described herein, such as for example, and antibody library with high functional diversity.

The ability to activate or inhibit the cell may include direct fusion of an activation domain or an inhibition domain (such as an 41BB signaling domain and/or a CD3 zeta signaling domain), or alternatively by a binding domain, either extracellular or intracellular, that has affinity to an endogenous signaling complex (e.g., an anti-CD3e domain that associates the vector polypeptide with the TCR signaling complex).

The method may further include contacting, or introducing members of, the plurality of vectors with cells from a cell line comprising a reporter polynucleotide operably connected to a promoter. The promoter may be activated by the recombinant polypeptide in the presence of a target antigen. In various embodiments, the target antigen may be found either on a cell or as one or more recombinant proteins. The reporter polynucleotide may encode a second detectable marker (e.g., a second optically detectable marker) or an enzyme that acts on the second detectable marker. The cells may produce endogenous signaling markers, such as CD69, CD25, etc. The first detectable marker and the second detectable marker may be different.

The method may further include isolating the cells expressing the first detectable marker to generate the library of cells expressing the plurality of recombinant polypeptides. Furthermore, the method may include isolating the cells expressing the first and second detectable markers when in contact with the target antigen to generate the library of cells expressing one or more recombinant polypeptides specific to the target antigen and capable of activating the cell bearing the signaling polypeptide when in presence of antigen.

The vector may be a viral vector. For example, the vector may be a viral vector selected from the group consisting of, but not limited to, a lentivirus, an alphavirus, a retrovirus, an adenovirus, a herpes virus, a poxvirus, an oncolytic virus, a reovirus, and/or an adeno associated virus (AAV). The vector may include a plasmid encoding the recombinant polypeptide. In some embodiments, the plasmid may further encode a selectable marker. For example, the plasmid may encode a selectable marker that is an antibiotic resistance marker providing resistance to an antibiotic. The antibiotic may be selected from the group consisting of, but not limited to, puromycin, hygromycin, kanamycin, ampicillin, tetracycline, chloroamphenicol, spectinomycin, streptomycin, carbenicillin, bleomycin, erythromycin, polymyxin B, Zeocin, G418 (geneticin), phleomycin, and blasticidin.

The plasmid may further include a 2A peptide or an internal ribosome entry site (IRES). The 2A peptide or IRES may be disposed between the CD3 zeta signaling domain and the first detectable marker. The 2A peptide may be selected from the group consisting of, but not limited to, T2A, P2A, E2A, and F2A.

The antigen binding domain may be an antibody or a fragment of an antibody. In certain embodiments, the antibody may include a VH domain and a VK domain in either order (e.g., VH VK or VK VH). The recombinant polypeptide may further include a GS linker, or any other suitable linker, disposed between the VH domain and the VK domain in either order. Moreover, the antibody may include a VHH domain. Other protein platforms are also within the scope of this disclosure. The antibody may include a scFv or multiple scFvs (e.g., a BiTE). The antibody may include a full IgG antibody. The antibody may include a Fab.

In some cases, the antigen binding domain may include a native or mutated protein folding domain. The native or mutated protein folding domain may be of any natural or synthetic origin. The antigen binding domain may include a polypeptide. The hinge domain may be a CD8 hinge or any other suitable hinge domain. The hinge domain may be any polypeptide.

The transmembrane domain may be selected from the group consisting of, but not limited to, a CD28 transmembrane domain, a CD4 transmembrane domain, a CD8 transmembrane domain, or any transmembrane domain of any known transmembrane protein.

The activation domain may be an intracellular signaling domain of a costimulatory molecule. In some embodiments, the polypeptide may not include a fused signaling domain. Instead, activation may be accomplished through a binding domain that recognizes an endogenous transmembrane signaling complex, therefore providing activation or inhibition signaling through that endogenous complex upon binding. The binding domain may be an scFv, VHH, IgG, or any polypeptide that specifically recognizes CD3e The polypeptide may be a BiTE polypeptide tethered to the outer membrane with a hinge and transmembrane. Accordingly, the polypeptide may activate the cell through the CD3e-bearing TCR signaling complex. The costimulatory molecule domain may be selected from one or more of the group consisting of, but not limited to, 4-1BB, OX40, CD28, CD27, CD40, IL12, CD40, caspase recruitment domain (CARD) family members, HVEM, DAP10, SLAMF family members, LAT, TRIM, Lck family members, inducible T cell costimulatory (ICOS), and/or any activation domain including an ITAM.

The inhibition domain may be an immune checkpoint inhibitor. The immune checkpoint inhibitor may be selected from the group consisting of, but not limited to, programmed cell death 1 (PD-1), cytotoxic T lymphocyte antigen-4 (CTLA-4), lymphocyte activation gene-3 (Lag3), T-cell immunoglobulin and mucin domain-3 (Tim-3), TIGIT, adenosine A2a receptor (A2aR), CD160, and/or CD244. The CD3 zeta signaling domain may include at least one immunoreceptor tyrosine-based activation motif (ITAM). Other activating domains and inhibiting domains are also within the scope of this disclosure.

The first detectable marker may be a first optically detectable marker. The first optically detectable marker may be selected from the group consisting of, but not limited to, a red fluorescent protein, an orange fluorescent protein, a blue fluorescent protein, and a green fluorescent protein. Any other suitable fluorescent protein is also within the scope of this disclosure. The red fluorescent protein may be mCherry. In some cases, the reporter cell line may be a Jurkat cell line. The second detectable marker may be a second optically detectable marker. The second optically detectable marker may be GFP. The second optically detectable marker may be luciferin. The enzyme that acts on the second optically detectable marker may be luciferase (e.g., firefly luciferase). The promoter may be selected from the group consisting of, but not limited to, an NFκB promoter, an IL-2 promoter, a NFAT promoter, an IFN-gamma promoter, and/or an IL-12 promoter.

The method of generating a library of cells expressing a plurality of recombinant polypeptides may further include expanding the library of cells expressing the plurality of recombinant polypeptides to produce a library of expanded cells. The method may further include applying an antibiotic to the library of expanded cells. In certain embodiments, the vector may include an antibiotic resistance marker that provides or is configured to provide resistance to an antibiotic. The antibiotic may be selected from the group consisting of, but not limited to, puromycin, hygromycin, kanamycin, ampicillin, tetracycline, chloroamphenicol, spectinomycin, streptomycin, carbenicillin, bleomycin, erythromycin, polymyxin B, and blasticidin.

Another aspect of the present disclosure is directed to a library of recombinant polypeptides produced by any of the methods of generating a library of cells expressing a plurality of recombinant polypeptides as provided herein.

Embodiments

Described herein are certain specific embodiments of the methods and libraries described herein.

Panning Strategy

Embodiment 1. A method of screening a library of cells comprising a plurality of recombinant polypeptides for specificity against a target antigen, the method comprising: a) obtaining a library of cells, wherein each cell in the library of cells comprises: i) a recombinant polypeptide comprising an antigen binding domain, a hinge domain, a transmembrane domain, an activation domain or an inhibition domain, and optionally a first detectable marker, wherein the antigen binding domain of the recombinant polypeptide in each cell of the library of cells is a different antigen binding domain, wherein each cell in the library of cells comprises a reporter polynucleotide operably connected to a promoter, wherein the promoter is activated by the recombinant polypeptide in the presence of a target antigen, wherein the reporter polynucleotide optionally encodes a second detectable marker or an enzyme that acts on the second detectable marker, and wherein the first detectable marker and the second detectable marker are different; or ii) a recombinant polypeptide comprising an antigen binding domain, a CD3e binding domain, a hinge domain, a transmembrane domain, and optionally a first detectable marker, wherein the antigen binding domain of the recombinant polypeptide in each cell of the library of cells is a different antigen binding domain, wherein each cell in the library of cells comprises a reporter polynucleotide operably connected to a promoter, wherein the promoter is activated by the CD3e binding domain in the presence of a target antigen, wherein the reporter polynucleotide optionally encodes a second detectable marker or an enzyme that acts on the second detectable marker, and wherein the first detectable marker and the second detectable marker are different; b) contacting the library of cells with a target antigen; c) sorting activated cells from non-activated cells following the contacting of step (b) thereby producing a first subset of activated cells; d) contacting the first subset of activated cells with a plurality of cells not expressing the target antigen; e) sorting non-activated cells from activated cells following the contacting of step d) thereby producing a subset of non-activated cells; f) contacting the subset of non-activated cells with the target antigen; and g) sorting activated cells from non-activated cells following the contacting of step f) thereby producing a second subset of activated cells.

Embodiment 2. The method of Embodiment 1, wherein the first detectable marker is a first optically detectable marker and the second detectable marker is a second optically detectable marker.

Embodiment 3. The method of Embodiment 2, wherein the activated cells are characterized by the following: (i) an increase in an optical intensity of the first optically detectable marker relative to the optical intensity of the first optically detectable marker in the non-activated cells; (ii) an increase in an optical intensity of the second optically detectable marker relative to the optical intensity of the second optically detectable marker in the non-activated cells; (iii) an increase in expression of at least one T cell endogenous signaling marker relative to the expression of the at least one T cell endogenous signaling marker in the non-activated cells; or (iv) any combination of (i)-(iii).

Embodiment 4. The method of Embodiment 3, wherein the non-activated cells are characterized by the following: (i) no increase in an optical intensity of the first optically detectable marker relative to the optical intensity of the first optically detectable marker in the activated cells; (ii) no increase in an optical intensity of the second optically detectable marker relative to the optical intensity of the second optically detectable marker in the activated cells; (iii) no increase in expression of at least one T cell endogenous signaling marker relative to the expression of the at least one T cell endogenous signaling marker in the activated cells; or (iv) any combination of (i)-(iii).

Embodiment 5. The method of Embodiment 3 or Embodiment 4, wherein the T cell endogenous signaling marker is selected from the group consisting of: CD69, CD25, and a combination thereof.

Embodiment 6. The method of any one of Embodiments 1-5, further comprising partitioning of the second subset of activated cells.

Embodiment 7. The method of Embodiment 6, wherein the partitioning is on a solid support.

Embodiment 8. The method of any one of Embodiments 1-7, wherein the target antigen is expressed on a plurality of cells.

Embodiment 9. The method of any one of Embodiments 1-7, wherein the target antigen is bound to a support.

Embodiment 10. The method of Embodiment 9, wherein the support is a bead.

Embodiment 11. The method of any one of Embodiments 1-7, wherein the target antigen is in a solution.

Embodiment 12. The method of any one of Embodiments 1-11, wherein the sorting activated cells from non-activated cells following the contacting of step (b) comprises flow cytometry cell sorting.

Embodiment 13. The method of any one of Embodiments 1-12, wherein the sorting non-activated cells from activated cells following the contacting of step (d) comprises flow cytometry cell sorting.

Embodiment 14. The method of any one of Embodiments 1-13, wherein the sorting activated cells from non-activated cells following the contacting of step (f) comprises flow cytometry cell sorting.

Embodiment 15. The method of any one of Embodiments 1-14, comprising applying a selectable pressure during: i) the contacting the library of cells with a target antigen of step (b), ii) the contacting the first subset of activated cells with a plurality of cells not expressing the target antigen, iii) the contacting the library of cells with a target antigen of step (f), or iv) a combination of (i)-(iii).

Embodiment 16. The method of any one of Embodiments 1-15, further comprising applying a selectable pressure to the second subset of activated cells.

Embodiment 17. The method of Embodiment 15 or Embodiment 16, wherein the selectable pressure is an abiotic pressure.

Embodiment 18. The method of Embodiment 17, wherein the abiotic pressure is an environmental condition.

Embodiment 19. The method of Embodiment 18, wherein the environmental condition is a tumor microenvironmental condition.

Embodiment 20. The method of Embodiment 19, wherein the tumor microenvironmental condition is hypoxia.

Embodiment 21. The method of Embodiment 17, wherein the abiotic pressure is a small molecule.

Embodiment 22. The method of Embodiment 21, wherein the small molecule is a therapeutic.

Embodiment 23. The method of Embodiment 15, where in the selectable pressure is a biotic pressure.

Embodiment 24. The method of Embodiment 21, wherein the biotic pressure is from a tumor microenvironment.

Embodiment 25. The method of Embodiment 21, wherein the biotic pressure is a biological fluid.

Embodiment 26. The method of Embodiment [0110], wherein the biological fluid is a cerebrospinal fluid.

Library Generation

Embodiment 27. A method of generating a library of cells expressing a plurality of recombinant polypeptides, the method comprising: obtaining a plurality of vectors, wherein each vector in the plurality of vectors encodes; a recombinant polypeptide comprising an antigen binding domain, a hinge domain, a transmembrane domain, an activation domain or an inhibition domain, and optionally a first detectable marker, wherein the antigen binding domain of each vector in the plurality of vectors is a different antigen binding domain; or a recombinant polypeptide comprising an antigen binding domain, a hinge domain, a transmembrane domain, a CD3e binding domain, and optionally a first detectable marker, wherein the antigen binding domain of each vector in the plurality of vectors is a different antigen binding domain; and contacting the plurality of vectors with cells from a cell line comprising a reporter polynucleotide operably connected to a promoter, wherein the promoter is activated by the recombinant polypeptide in the presence of a target antigen, wherein the reporter polynucleotide optionally encodes a second detectable marker or an enzyme that acts on the second detectable marker, and wherein the first detectable marker and the second detectable marker are different.

Embodiment 28. The method of Embodiment 27, wherein the vector is a viral vector.

Embodiment 29. The method of Embodiment 28, wherein the viral vector is selected from the group consisting of: a lentivirus, an alphavirus, a retrovirus, an adenovirus, a herpes virus, a poxvirus, an oncolytic virus, a reovirus, or an adeno associated virus (AAV).

Embodiment 30. The method of any one of Embodiments 27-29, wherein the vector comprises a plasmid encoding the recombinant polypeptide.

Embodiment 31. The method of Embodiment 30, wherein the plasmid further encodes a selectable marker.

Embodiment 32. The method of Embodiment 31, wherein the selectable marker is an antibiotic resistance marker providing resistance to an antibiotic.

Embodiment 33. The method of Embodiment 32, wherein the antibiotic is selected from the group consisting of: puromycin, hygromycin, kanamycin, ampicillin, tetracycline, chloroamphenicol, spectinomycin, streptomycin, carbenicillin, bleomycin, erthyromycin, zeocin, geneticin, phleomycin, polymyxin B, and blasticidin.

Embodiment 34. The method of any one of Embodiments 30-33, wherein the plasmid further comprises a 2A peptide or an internal ribosome entry site (IRES).

Embodiment 35. The method of Embodiment 34, wherein the 2A peptide or IRES is disposed between the activation domain, wherein the activation domain is a CD3 zeta signaling domain, and the first detectable marker.

Embodiment 36. The method of Embodiment 34 or Embodiment 35, wherein the 2A peptide is selected from the group consisting of: T2A, P2A, E2A, and F2A.

Embodiment 37. The method of any one of Embodiments 27-36, wherein the antigen binding domain can be selected from the group consisting of: Fab, scFab, Fab', F(ab')2, diabody, triabody, minibody, scFv-Fc, scFv, and more than one scFv.

Embodiment 38. The method of Embodiment 37, wherein the more than one scFv is a Bi-specific T-cell engager (BiTE).

Embodiment 39. The method of any one of Embodiments 27-38, wherein the antigen binding domain can comprise a VH domain, a VK domain, a VHH domain, or a combination thereof.

Embodiment 40. The method of Embodiment 39, wherein the antigen binding domain comprises a VH domain and a VK domain.

Embodiment 41. The method of Embodiment 40, wherein the recombinant polypeptide further comprises a GS linker disposed between the VH domain and the VK domain.

Embodiment 42. The method of any one of Embodiments 27-39, wherein the antigen binding domain can comprise an IgG antibody.

Embodiment 43. The method of any one of Embodiments 27-42, wherein the hinge domain is selected from the group consisting of: a CD8 hinge, a CD28 hinge, and an IgG hinge.

Embodiment 44. The method of Embodiment 43, wherein the IgG hinge is an IgG1 hinge.

Embodiment 45. The method of any one of Embodiments 27-44, wherein the transmembrane domain comprises a hydrophobic alpha helix.

Embodiment 46. The method of any one of Embodiments 27-45, wherein the transmembrane domain is selected from the group consisting of: a CD28 transmembrane domain, a CD4 transmembrane domain, a CD8 transmembrane domain, a CD45 transmembrane domain, a CD3 transmembrane domain, a CD9 transmembrane domain, a CD16 transmembrane domain, a CD22 transmembrane domain, a CD33 transmembrane domain, a CD37 transmembrane domain, a CD64 transmembrane domain, a CD80 transmembrane domain, a CD86 transmembrane domain, a CD134 transmembrane domain, a CD137 transmembrane domain, a CD154 transmembrane domain.

Embodiment 47. The method of any one of Embodiments 27-46, wherein the activation domain comprises at least one costimulatory domain.

Embodiment 48. The method of any one of Embodiments 27-47, wherein the at least one costimulatory domain is selected from the group consisting of: 4-1BB, OX40, CD28, CD27,CD40, IL12, inducible T cell costimulator (ICOS), a caspase recruitment domain (CARD) family member, HVEM, DAP10, a SLAMF family member,LAT, TRIM, a Lck family member, and any combination thereof.

Embodiment 49. The method any one of Embodiments 27-48, wherein the activation domain comprises at least one immunoreceptor tyrosine-based activation motif (ITAM).

Embodiment 50. The method any one of Embodiments 27-49, wherein the recombinant polypeptide further comprises at least one immunoreceptor tyrosine-based activation motif (ITAM).

Embodiment 51. The method of any one of Embodiments 27-50, wherein the inhibition domain comprises at least one immunoreceptor tyrosine-based inhibition motif (ITIM) or immunoreceptor tyrosine-based switch motif (ITSM).

Embodiment 52. The method of any one of Embodiments 27-51, wherein the inhibition domain comprises at least one immune checkpoint inhibitor.

Embodiment 53. The method of Embodiment 52, wherein the at least one immune checkpoint inhibitor is selected from the group consisting of: programmed cell death 1 (PD-1), cytotoxic T lymphocyte antigen-4 (CTLA-4), lymphocyte activation gene-3 (Lag3), T-cell immunoglobulin and mucin domain-3 (Tim-3), TIGIT, adenosine A2a receptor (A2aR), CD160, CD244, and any combination thereof.

Embodiment 54. The method of any one of Embodiments 27-53, wherein the first detectable marker is a first optically detectable marker.

Embodiment 55. The method of Embodiment 54, wherein the first optically detectable marker is selected from the group consisting of: a red fluorescent protein, an orange fluorescent protein, a blue fluorescent protein, a yellow fluorescent protein, and a green fluorescent protein.

Embodiment 56. The method of Embodiment 55, wherein the red fluorescent protein is mCherry.

Embodiment 57. The method of any one of Embodiments 27-56, wherein the reporter cell line is a Jurkat cell line.

Embodiment 58. The method of any one of Embodiments 27-57, wherein the second detectable marker is a second optically detectable marker.

Embodiment 59. The method of Embodiment 58, wherein the second optically detectable marker is GFP.

Embodiment 60. The method of any one of Embodiments 58, wherein the second optically detectable marker is luciferin.

Embodiment 61. The method of Embodiment 60, wherein the enzyme that acts on the second detectable marker is luciferase.

Embodiment 62. The method of any one of Embodiments 27-61, wherein the second detectable marker is a T cell endogenous signaling marker.

Embodiment 63. The method of Embodiment 62, wherein the endogenous signaling marker is selected from the group consisting of: CD69, CD25, and a combination thereof.

Embodiment 64. The method of any one of Embodiments 27-63, wherein the promoter is selected from the group consisting of: an NFκB promoter, an IL-2 promoter, a NFAT promoter, an IFN-gamma promoter, and IL-12 promoter.

Embodiment 65. The method of any one of Embodiments 27-64, further comprising expanding the library of cells expressing the plurality of recombinant polypeptides, thereby producing a library of expanded cells.

Embodiment 66. The method of Embodiment 65, further comprising applying an antibiotic to the library of expanded cells.

Embodiment 67. The method of Embodiment 66, wherein the vector comprises an antibiotic resistance marker providing resistance to an antibiotic.

Embodiment 68. The method of Embodiment 67, wherein the antibiotic is selected from the group consisting of: puromycin, hygromycin, kanamycin, ampicillin, tetracycline, chloroamphenicol, spectinomycin, streptomycin, carbenicillin, bleomycin, erythromycin, polymyxin B, and blasticidin.

Embodiment 69. A library of recombinant polypeptides produced by the method of any one of Embodiments 27-68.

Single Cell with Construct

Embodiment 70. A cell comprising: a) a recombinant polypeptide comprising: i) an antigen binding domain, a hinge domain, a transmembrane domain, an activation domain or an inhibition domain, and optionally a first detectable marker; or ii) an antigen binding domain, a hinge domain, a transmembrane domain, a CD3e binding domain, and a optionally first detectable marker; and b) a reporter polynucleotide operably connected to a promoter, wherein the promoter is activated by the recombinant polypeptide in the presence of a target antigen, and wherein the reporter polynucleotide optionally encodes a second detectable marker or an enzyme that acts on the second detectable marker, and wherein the first detectable marker and the second detectable marker are different.

Embodiment 71. The cell of Embodiment 70, wherein the antigen binding domain can be selected from the group consisting of: Fab, scFab, Fab', F(ab')2, diabody, triabody, minibody, scFv-Fc, scFv, and more than one scFv.

Embodiment 72. The cell of Embodiment 71, wherein the more than one scFv is a Bi-specific T-cell engager (BiTE).

Embodiment 73. The cell of Embodiment 70 or Embodiment 71, wherein the antigen binding domain can comprise a VH domain, a VK domain, a VHH domain, or a combination thereof.

Embodiment 74. The cell of Embodiment 73, wherein the antigen binding domain comprises a VH domain and a VK domain.

Embodiment 75. The cell of Embodiment 74, wherein the recombinant polypeptide further comprises a GS linker disposed between the VH domain and the VK domain.

Embodiment 76. The cell of any one of Embodiments 70-75, wherein the antigen binding domain can comprise an IgG antibody.

Embodiment 77. The cell of any one of Embodiments 70-76, wherein the hinge domain is selected from the group consisting of: a CD8 hinge, a CD28 hinge, and an IgG hinge.

Embodiment 78. The cell of Embodiment 77, wherein the IgG hinge is an IgG1 hinge.

Embodiment 79. The cell of any one of Embodiments 70-78, wherein the transmembrane domain comprises a hydrophobic alpha helix.

Embodiment 80. The cell of any one of Embodiments 70-79, wherein the transmembrane domain is selected from the group consisting of: a CD28 transmembrane domain, a CD4 transmembrane domain, a CD8 transmembrane domain, a CD45 transmembrane domain, a CD3 transmembrane domain, a CD9 transmembrane domain, a CD16 transmembrane domain, a CD22 transmembrane domain, a CD33 transmembrane domain, a CD37 transmembrane domain, a CD64 transmembrane domain, a CD80 transmembrane domain, a CD86 transmembrane domain, a CD134 transmembrane domain, a CD137 transmembrane domain, a CD154 transmembrane domain.

Embodiment 81. The cell of any one of Embodiments 70-80, wherein the activation domain comprises at least one costimulatory domain.

Embodiment 82. The cell of Embodiment 81, wherein the at least one costimulatory domain is selected from the group consisting of: 4-1BB, OX40, CD28, CD27,CD40, IL12, inducible T cell costimulator (ICOS), a caspase recruitment domain (CARD) family member, HVEM, DAP10, a SLAMF family member, LAT, TRIM, a Lck family member, and any combination thereof.

Embodiment 83. The cell any one of Embodiments 70-80, wherein the activation domain comprises at least one immunoreceptor tyrosine-based activation motif (ITAM).

Embodiment 84. The cell any one of Embodiments 70-80, wherein the recombinant polypeptide further comprises at least one immunoreceptor tyrosine-based activation motif (ITAM).

Embodiment 85. The cell of any one of Embodiments 70-80, wherein the inhibition domain comprises at least one immunoreceptor tyrosine-based inhibition motif (ITIM) or immunoreceptor tyrosine-based switch motif (ITSM).

Embodiment 86. The cell of any one of Embodiments 70-80, wherein the inhibition domain comprises at least one immune checkpoint inhibitor.

Embodiment 87. The cell of Embodiment 86, wherein the at least one immune checkpoint inhibitor is selected from the group consisting of: programmed cell death 1 (PD-1), cytotoxic T lymphocyte antigen-4 (CTLA-4), lymphocyte activation gene-3 (Lag3), T-cell immunoglobulin and mucin domain-3 (Tim-3), TIGIT, adenosine A2a receptor (A2aR), CD160, CD244, and any combination thereof.

Embodiment 88. The cell of any one of Embodiments 70-87, wherein the first detectable marker is a first optically detectable marker.

Embodiment 89. The cell of Embodiment 88, wherein the first optically detectable marker is selected from the group consisting of: a red fluorescent protein, an orange fluorescent protein, a blue fluorescent protein, a yellow fluorescent protein, and a green fluorescent protein.

Embodiment 90. The cell of Embodiment 89, wherein the red fluorescent protein is mCherry.

Embodiment 91. The cell of any one of Embodiments 70-90, wherein the reporter cell line is a Jurkat cell line.

Embodiment 92. The cell of any one of Embodiments 70-91, wherein the second detectable marker is a second optically detectable marker.

Embodiment 93. The cell of Embodiment 92, wherein the second optically detectable marker is GFP.

Embodiment 94. The cell of any one of Embodiments 92, wherein the second optically detectable marker is luciferin.

Embodiment 95. The cell of Embodiment 94, wherein the enzyme that acts on the second detectable marker is luciferase.

Embodiment 96. The cell of any one of Embodiments 70-91, wherein the second detectable marker is a T cell endogenous signaling marker.

Embodiment 97. The cell of Embodiment 96, wherein the endogenous signaling marker is selected from the group consisting of: CD69, CD25, and a combination thereof.

Embodiment 98. The cell of any one of Embodiments 70-97, wherein the promoter is selected from the group consisting of: an NFκB promoter, an IL-2 promoter, an NFAT promoter, an IFN-gamma promoter, and an IL-12 promoter.

Library of Constructs

Embodiment 99. A library of cells comprising: a plurality of cells, each cell in the plurality of cells comprising: a recombinant polypeptide comprising; a) an antigen binding domain, a hinge domain, a transmembrane domain, an activation domain or an inhibition domain, and optionally a first detectable marker, wherein the antigen binding domain of the recombinant polypeptide in each cell of the plurality of cells is a different antigen binding domain; or b) an antigen binding domain, a hinge domain, a transmembrane domain, a CD3e binding domain, and optionally a first detectable marker, wherein the antigen binding domain of the recombinant polypeptide in each cell of the plurality of cells is a different antigen binding domain; wherein each cell in the library of cells comprises a reporter polynucleotide operably connected to a promoter, wherein the promoter is activated by the recombinant polypeptide in the presence of a target antigen, wherein the reporter polynucleotide optionally encodes a second optically detectable marker or an enzyme that acts on the second optically detectable marker, and wherein the first optically detectable marker and the second optically detectable marker are different.

Embodiment 100. The library of Embodiment 99, wherein the antigen binding domain can be selected from the group consisting of: Fab, scFab, Fab', F(ab')2, diabody, triabody, minibody, scFv-Fc, scFv, and more than one scFv.

Embodiment 101. The library of Embodiment 100, wherein the more than one scFv is a Bi-specific T-cell engager (BiTE).

Embodiment 102. The library of Embodiment 99 or Embodiment 100, wherein the antigen binding domain can comprise a VH domain, a VK domain, a VHH domain, or a combination thereof.

Embodiment 103. The library of Embodiment 102, wherein the antigen binding domain comprises a VH domain and a VK domain.

Embodiment 104. The library of Embodiment 103, wherein the recombinant polypeptide further comprises a GS linker disposed between the VH domain and the VK domain.

Embodiment 105. The library of any one of Embodiments 99-104, wherein the antigen binding domain can comprise an IgG antibody.

Embodiment 106. The library of any one of Embodiments 99-105, wherein the hinge domain is selected from the group consisting of: a CD8 hinge, a CD28 hinge, and an IgG hinge.

Embodiment 107. The library of Embodiment 106, wherein the IgG hinge is an IgG1 hinge.

Embodiment 108. The library of any one of Embodiments 99-107, wherein the transmembrane domain comprises a hydrophobic alpha helix.

Embodiment 109. The library of any one of Embodiments 99-108, wherein the transmembrane domain is selected from the group consisting of: a CD28 transmembrane domain, a CD4 transmembrane domain, a CD8 transmembrane domain, a CD45 transmembrane domain, a CD3 transmembrane domain, a CD9 transmembrane domain, a CD16 transmembrane domain, a CD22 transmembrane domain, a CD33 transmembrane domain, a CD37 transmembrane domain, a CD64 transmembrane domain, a CD80 transmembrane domain, a CD86 transmembrane domain, a CD134 transmembrane domain, a CD137 transmembrane domain, a CD154 transmembrane domain.

Embodiment 110. The library of any one of Embodiments 99-109, wherein the activation domain comprises at least one costimulatory domain.

Embodiment 111. The library of Embodiment 110, wherein the at least one costimulatory domain is selected from the group consisting of: 4-1BB, OX40, CD28, CD27, CD40, IL12, inducible T cell costimulator (ICOS), a caspase recruitment domain (CARD) family member, HVEM, DAP10, a SLAMF family member,LAT, TRIM, a Lck family member, and any combination thereof.

Embodiment 112. The library any one of Embodiments 99-109, wherein the activation domain comprises at least one immunoreceptor tyrosine-based activation motif (ITAM).

Embodiment 113. The library any one of Embodiments 99-109, wherein the recombinant polypeptide further comprises at least one immunoreceptor tyrosine-based activation motif (ITAM).

Embodiment 114. The library of any one of Embodiments 99-109, wherein the inhibition domain comprises at least one immunoreceptor tyrosine-based inhibition motif (ITIM) or immunoreceptor tyrosine-based switch motif (ITSM).

Embodiment 115. The method of any one of Embodiments 99-109, wherein the inhibition domain comprises at least one immune checkpoint inhibitor.

Embodiment 116. The library of Embodiment 115, wherein the at least one immune checkpoint inhibitor is selected from the group consisting of: programmed cell death 1 (PD-1), cytotoxic T lymphocyte antigen-4 (CTLA-4), lymphocyte activation gene-3 (Lag3), T-cell immunoglobulin and mucin domain-3 (Tim-3), TIGIT, adenosine A2a receptor (A2aR), CD160, CD244, and any combination thereof.

Embodiment 117. The library of any one of Embodiments 99-116, wherein the first detectable marker is a first optically detectable marker.

Embodiment 118. The library of Embodiment 117, wherein the first optically detectable marker is selected from the group consisting of: a red fluorescent protein, an orange fluorescent protein, a blue fluorescent protein, a yellow fluorescent protein, and a green fluorescent protein.

Embodiment 119. The library of Embodiment 118, wherein the red fluorescent protein is mCherry.

Embodiment 120. The library of any one of Embodiments 99-119, wherein the reporter cell line is a Jurkat cell line.

Embodiment 121. The library of any one of Embodiments 99-120, wherein the second detectable marker is a second optically detectable marker.

Embodiment 122. The library of Embodiment 121, wherein the second optically detectable marker is GFP.

Embodiment 123. The library of any one of Embodiments 121, wherein the second optically detectable marker is luciferin.

Embodiment 124. The library of Embodiment 123, wherein the enzyme that acts on the second detectable marker is luciferase.

Embodiment 125. The library of any one of Embodiments 99-120, wherein the second detectable marker is a T cell endogenous signaling marker.

Embodiment 126. The library of Embodiment 125, wherein the endogenous signaling marker is selected from the group consisting of: CD69, CD25, and a combination thereof.

Embodiment 127. The library of any one of Embodiments 99-126, wherein the promoter is selected from the group consisting of: an NFκB promoter, an IL-2 promoter, a NFAT promoter, an IFN-gamma promoter, and IL-12 promoter.

EXAMPLES

Example 1: Library Generation

Figure 5A:
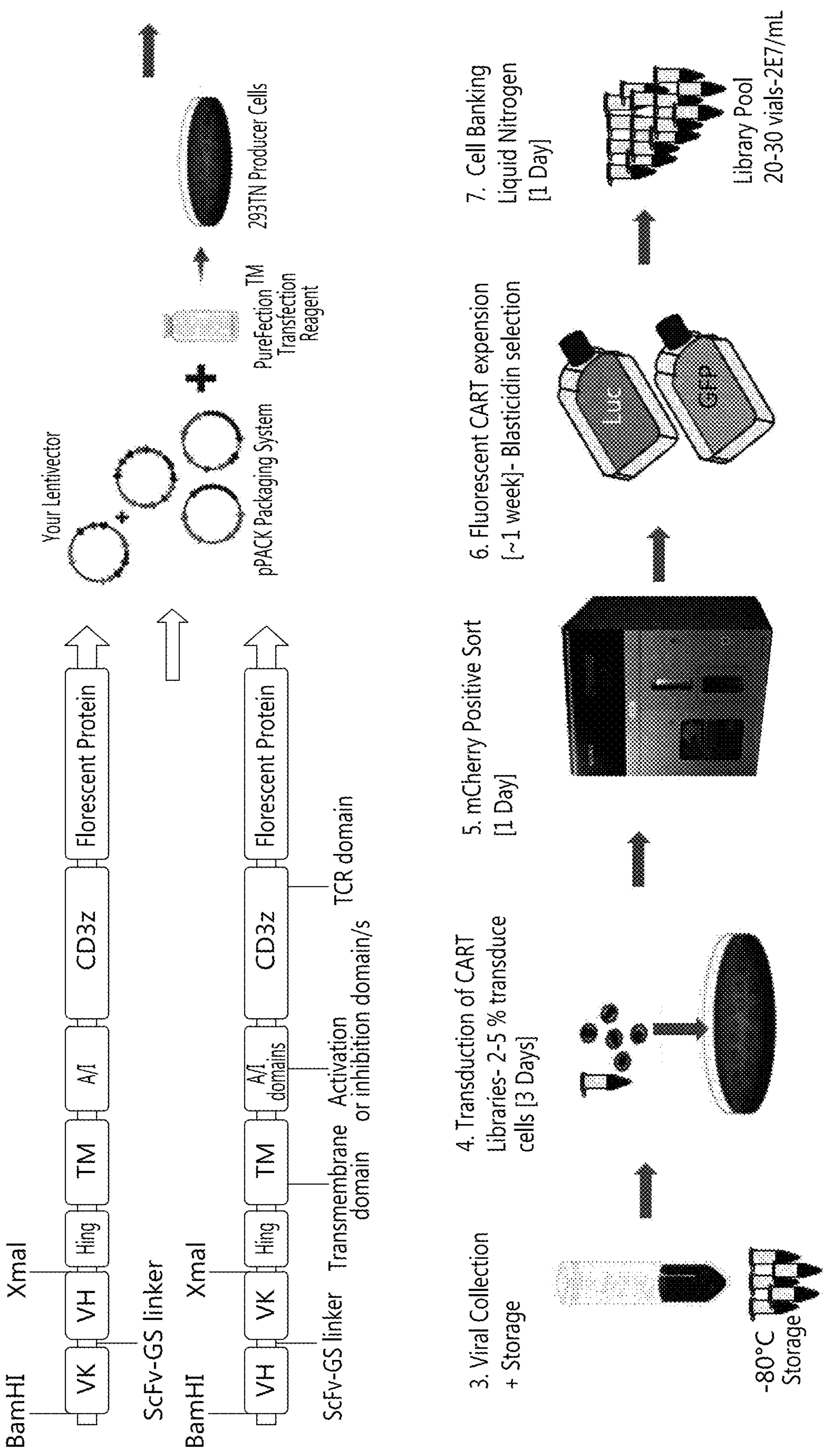
FIGS. 5A-5B illustrate a method of generating a CART library.
Figure 5B:
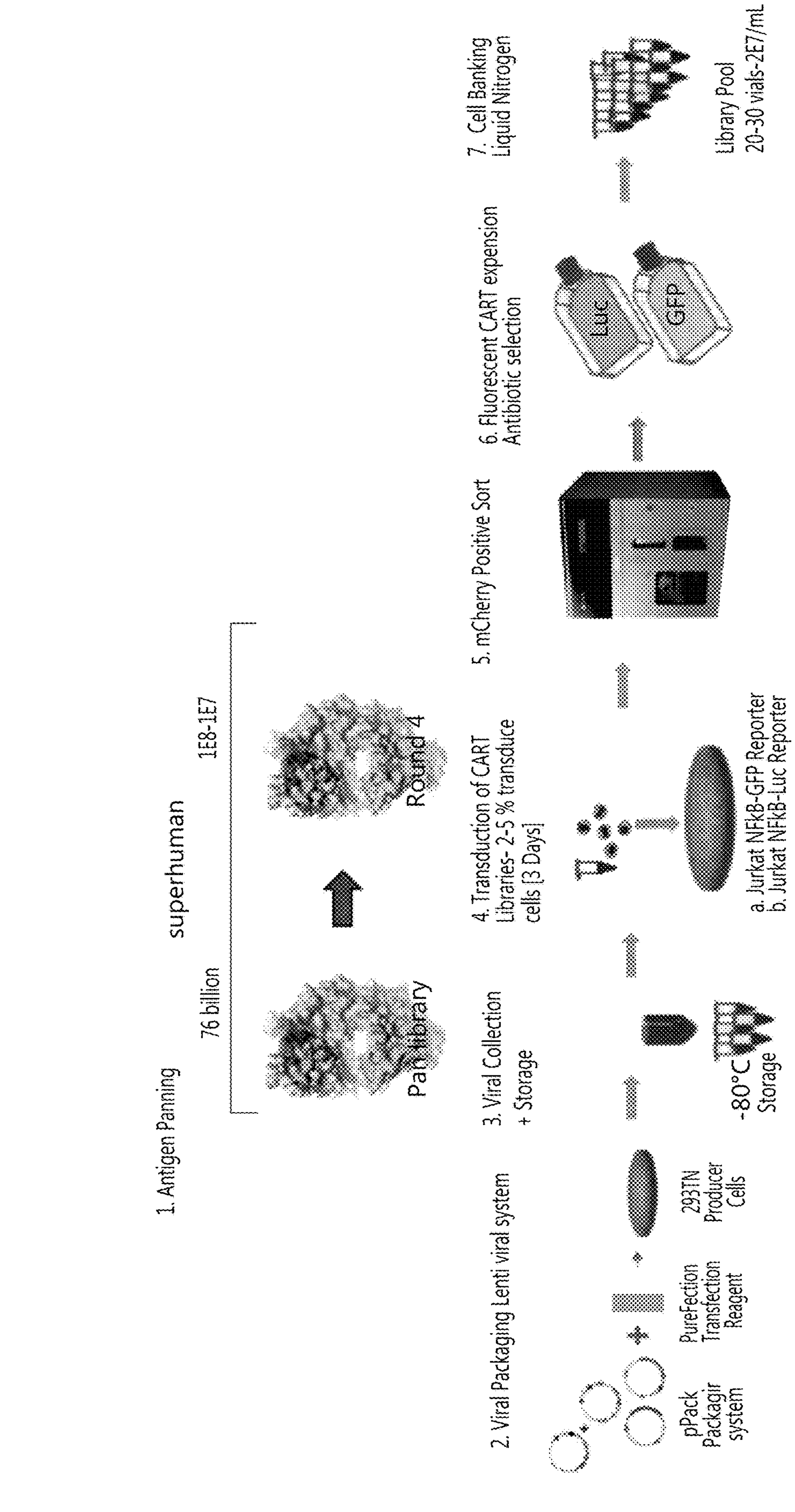

An example of a method of generating a CAR-T library is illustrated in FIG. 5A and FIG. 5B.

1. An scFv library is cloned into CAR constructs, which include a hinge, transmembrane domain, activation or inhibition domains, a CD3 zeta repeat or other similar repeat, and fluorescent protein(s).
2. Viral particles are generated using a third-generation lenti packaging system (other generations may be used).
3. Viral vectors are harvested, stored, and titer evaluated using a commercial p24 system or any system compatible with the viral system in use.
4. Transduction of the library in the appropriate Jurkat reporter cell line (NFκB-GFP or NFκB luciferase) or other systems that fit the specific application.
5. Transduced cells are sorted based on the fluorescent protein(s) attached to the CAR construct only.
6. Expansion of the library using selection antibiotics that are expressed by the CAR vector.
7. Banking the library in pools for panning different targets.

Example 2: Panning Strategy

Figure 6:
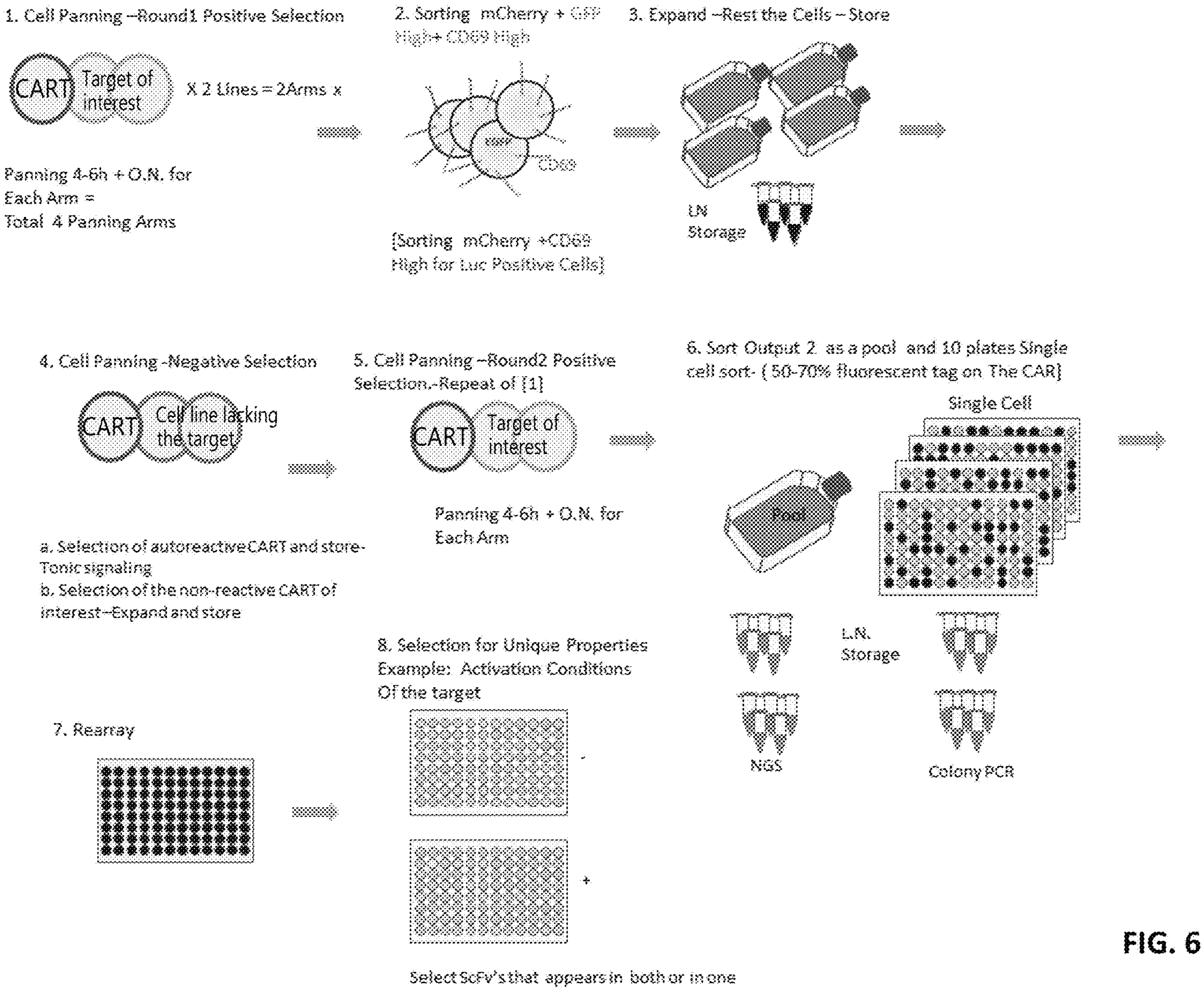
FIG. 6 illustrates a method of CART panning.

An example of a panning strategy is illustrated in FIG. 6.

1. Cell panning—Round 1 positive selection to collect all the scFvs (and other platform of interest) to be selected.
2. The activated cells are sorted via GFP, CD69, and fluorescent protein(s) among other activations markers.
3. The activated cells expressing the CARs with the scFv of interest are expanded.
4. Round 1 continues with screening the cells with the positive CARs from round 1 with cells that lack the target antigen. This eliminates either sticky, non-specific, or constantly activated CARs (tonic signaling).
5. Round 2 of positive selection.
6. Sort Output 2 as a pool and 10 plates single cell sort (50-70% fluorescent tag on the CAR, i.e., mCherry, etc.].

7. Re-array positive clones that are activated specifically.
8. Run test assay to identify unique sequences based on specific properties.

Example 3: Generation of CART19 Libraries

CARs with a CD19 antigen binding domain and further expressing an mCherry fluorescent marker (CART19; Table 1) were transduced with Lenti packaging using pPACKH1-XL HIV Lentivector Packaging kit from SBI system biosciences. This was a third generation Lenti-packaging system containing three plasmids that produce all the structural and replication proteins needed to transcribe and package an RNA copy of the expression lentivector into recombinant, VSV-G-pseudotyped lentiviral particles.

TABLE 1

Sequence

| SEQ ID NO: | Sequence | Description |
|---|---|---|
| 1 | ATGGCCCTGCCTGTGACAGCCCTGCTGCTGCCTCTGGCTCTGCTGCT<br>GCATGCCGCTAGACCCGGATCCGAAATTGTGATGACCAGTCACCCGC<br>CACTCTTAGCCTTTCACCCGGTGAGCGCGCAACCCTGTCTTGCAGAG<br>CCTCCCAAGACATCTCAAAATACCTTAATTGGTATCAACAGAAGCCC<br>GGACAGGCTCCTCGCCTTCTGATCTACCACACCAGCCGGCTCCATTC<br>TGGAATCCCTGCCAGGTTCAGCGGTAGCGGATCTGGGACCGACTACA<br>CCCTCACTATCAGCTCACTGCAGCCAGAGGACTTCGCTGTCTATTTC<br>TGTCAGCAAGGGAACACCCTGCCCTACACCTTTGGACAGGGCACCAA<br>GCTCGAGATTAAACATGCATCCGGTGGAGGCGGTTCAGGCGGAGGTG<br>GCTCTGGCGGTGGCGGATCGACCGGTCAGGTCCAACTCCAAGAAAGC<br>GGACCGGGTCTTGTGAAGCCATCAGAAACTCTTTCACTGACTTGTAC<br>TGTGAGCGGAGTGTCTCTCCCCGATTACGGGGTGTCTTGGATCAGAC<br>AGCCACCGGGGAAGGGTCTGGAATGGATTGGAGTGATTTGGGGCTCT<br>GAGACTACTTACTACTCTTCATCCCTCAAGTCACGCGTCACCATCTC<br>AAAGGACAACTCTAAGAATCAGGTGTCACTGAAACTGTCATCTGTGA<br>CCGCAGCCGACACCGCCGTGTACTATTGCGCTAAGCATTACTATTAC<br>GGCGGGAGCTACGCAATGGATTACTGGGGACAGGGTACTCTGGTCAC<br>CGTGTCCAGCCCCGGGACCACAACTCCAGCACCACGACCACCAACAC<br>CAGCACCTACAATCGCTTCTCAGCCTCTGTCCCTGCGCCCAGAGGCG<br>TGCCGACCAGCTGCAGGAGGAGCAGTGCACACGAGGGGACTGGACTT<br>CGCTTGTGATATCTACATCTGGGCGCCCTTGGCCGGGACTTGTGGGG<br>TCCTTCTCCTGTCACTGGTTATCACCCTTTACTGCAAACGGGGCAGA<br>AAGAAACTCCTGTATATATTCAAACAACCATTTATGAGACCAGTACA<br>AACTACTCAAGAGGAAGATGGCTGTAGCTGCCGATTTCCAGAAGAAG<br>AAGAAGGAGGATGTGAACTGAGAGTGAAGTTCAGCAGGAGCGCAGAC<br>GCCCCCGCGTACAAGCAGGGCCAGAACCAGCTCTATAACGAGCTCAA<br>TCTAGGACGAAGAGAGGAGTACGATGTTTTGGACAAGAGACGTGGCC<br>GGGACCCTGAGATGGGGGGAAAGCCGAGAAGGAAGAACCCTCAGGAA<br>GGCCTGTACAATGAACTGCAGAAAGATAAGATGGCGGAGGCCTACAG<br>TGAGATTGGGATGAAAGGCGAGCGCCGGAGGGGCAAGGGGCACGACG<br>GCCTTTACCAGGGTCTCAGTACAGCCACCAAGGACACCTACGACGCC<br>CTTCACATGCAGGCCCTGCCCCCTCGCGGTGGCGGATCTGGAGGTGG<br>ATCAGTGAGCAAGGGTGAAGAGGATAACATGGCTATCATCAAGGAGT<br>TCATGCGCTTCAAGGTGCACATGGAAGGCTCCGTGAACGGCCACGAG<br>TTCGAGATCGAAGGTGAAGGAGAGGGTCGCCCATACGAGGGCACCCA<br>GACCGCCAAGCTGAAGGTGACCAAGGGTGGCCCCCTGCCCTTCGCCT<br>GGGATATCCTGTCCCCTCAGTTCATGTACGGCTCCAAGGCCTACGTG<br>AAGCACCCCGCCGACATCCCCGACTACTTGAAGCTGTCCTTCCCCGA<br>GGGCTTCAAGTGGGAGCGCGTGATGAACTTCGAGGACGGCGGCGTGG<br>TGACCGTGACCCAGGACTCCTCCCTCCAGGACGGCGAGTTCATCTAC<br>AAGGTGAAGCTGCGCGGCACCAACTTCCCCTCCGACGGCCCCGTAAT<br>GCAGAAGAAGACCATGGGCTGGGAGGCCTCCTCCGAGCGGATGTACC<br>CCGAGGACGGCGCCCTGAAGGGCGAGATCAAGCAGAGGCTGAAGCTG<br>AAGGACGGCGGCCACTACGACGCTGAGGTCAAGACCACCTACAAGGC<br>CAAGAAGCCCGTGCAGCTGCCCGGCGCCTACAACGTCAACATCAAGT<br>TGGACATCACCTCCCACAACGAGGACTACACCATCGTGGAACAGTAC<br>GAACGCGCCGAGGGCCGCCACTCCACCGGCGGCATGGACGAGCTGTA<br>CAAG | CART19 expressing mCherry |

Figure 3A:
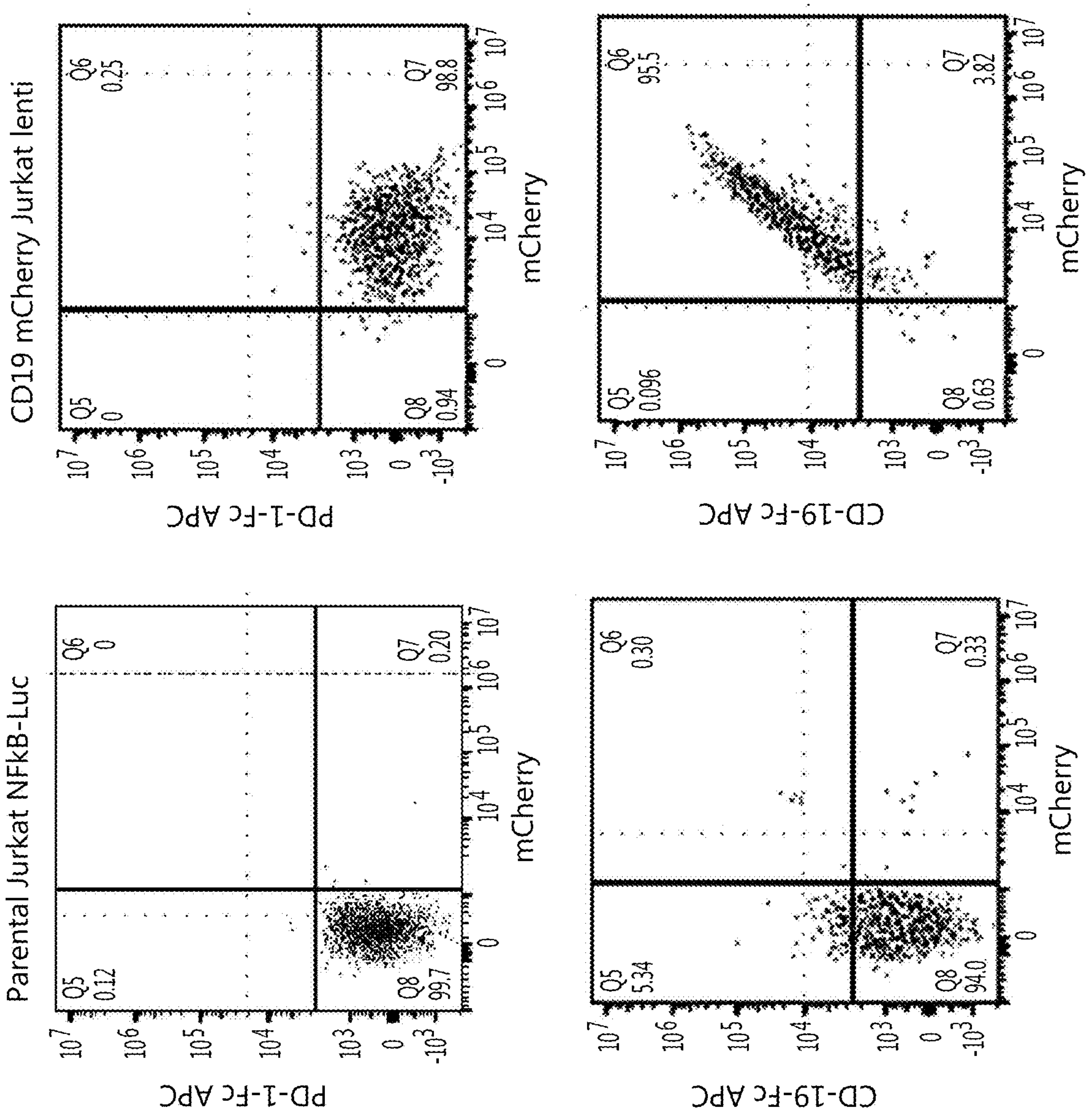
FIG. 3A-3C illustrate CD19-CART-mCherry surface expression on Jurkat NFκB-Luc and Jurkat NFκB-GFP reporter cell lines.
Figure 3B:
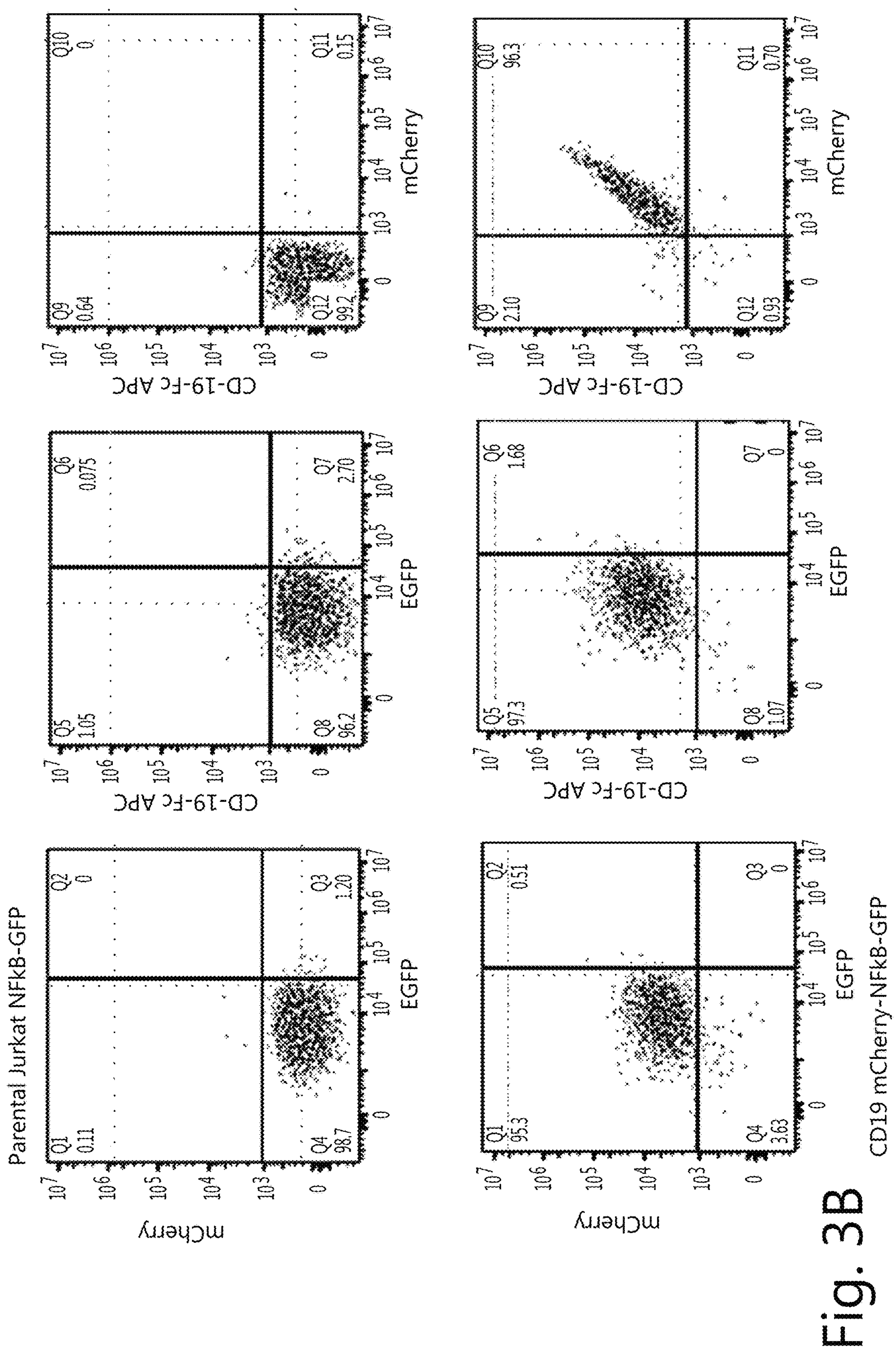
Figure 3C:
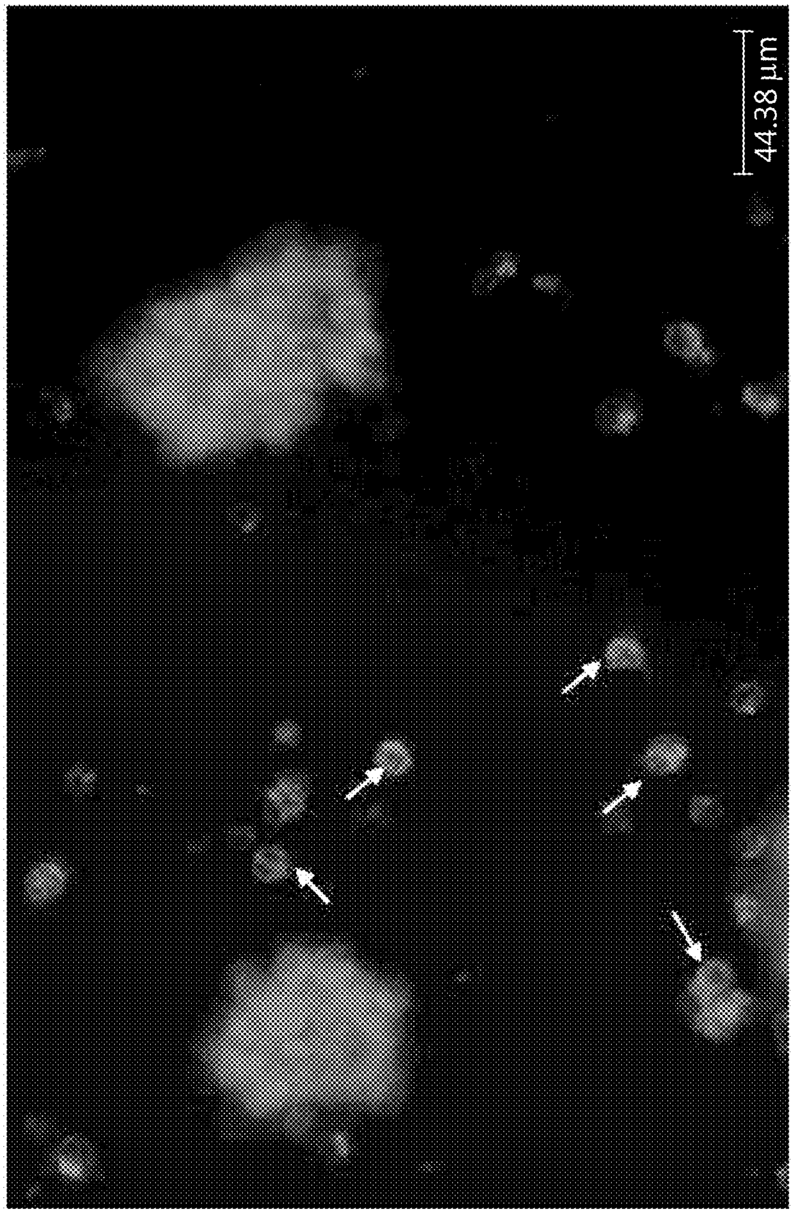

A lentivector construct for each CAR in the CAR library was packaged into HEK 293TN cells. Viral vectors were harvested and used to transduce a Jurkat NFκB-Luciferase (Luc) reporter cell line and in parallel separately into a Jurkat NFκB-GFP reporter cell line. The lenti-vector construct becomes stably integrated into the genome of the target cells for long-term expression. Fluorescent activated cell sorting (FACS) plots showed high co-expression of CD19 scFv (stained with CD19 Fc—allophycocyanin (APC)) and mCherry on the cell surface of the Jurkat NFκB-Luc reporter cell line (FIG. 3A) and on the cell surface of the Jurkat NFκB-GFP reporter cell line (FIG. 3B). Fluorescent microscopy of Jurkat cells from FIG. 3A showing mCherry fluorescence on the surface of the cell membrane indicated translocation of the construct to the cell surface (FIG. 3C).

The Luc system can be tested using luciferin as a substrate and a luminometer. The increase in GFP expression can be measured by flow cytometry. Activation can last between 2 hours to overnight with a peak activation range from 5 hours to 18 hours. Appropriate CAR-T cells that become activated can be sorted via several markers. A first marker can be GFP as indicated by increased expression of GFP signal due to NFκB activation. A second marker can be the increase of T cell activation markers such as CD69 and/or CD25, but not excluding other activation markers. A third marker can be the increase in the fluorescent intensity of the fluorescent protein attached to the C-terminus of the CAR-T construct (i.e., RFP, mCherry, BFP, or any other available fluorescent protein). The increase in the third marker was due to specific activation of the CAR construct and not due to activation of the Jurkat cells with a non-related factor (such as cytokines, growth factors, superantigens, or CD3 activating antibodies).

For the current experiments, NFκB promoter was used as the response activation element but other promoters can be used to evaluate different signaling pathways. These promotors can include, but are not limited to, IL-2, NFAT, IFN-gamma, and IL12 promoters.

Example 4: Screening of Jurkat NFκB-Luc CART19

Figure 4A:
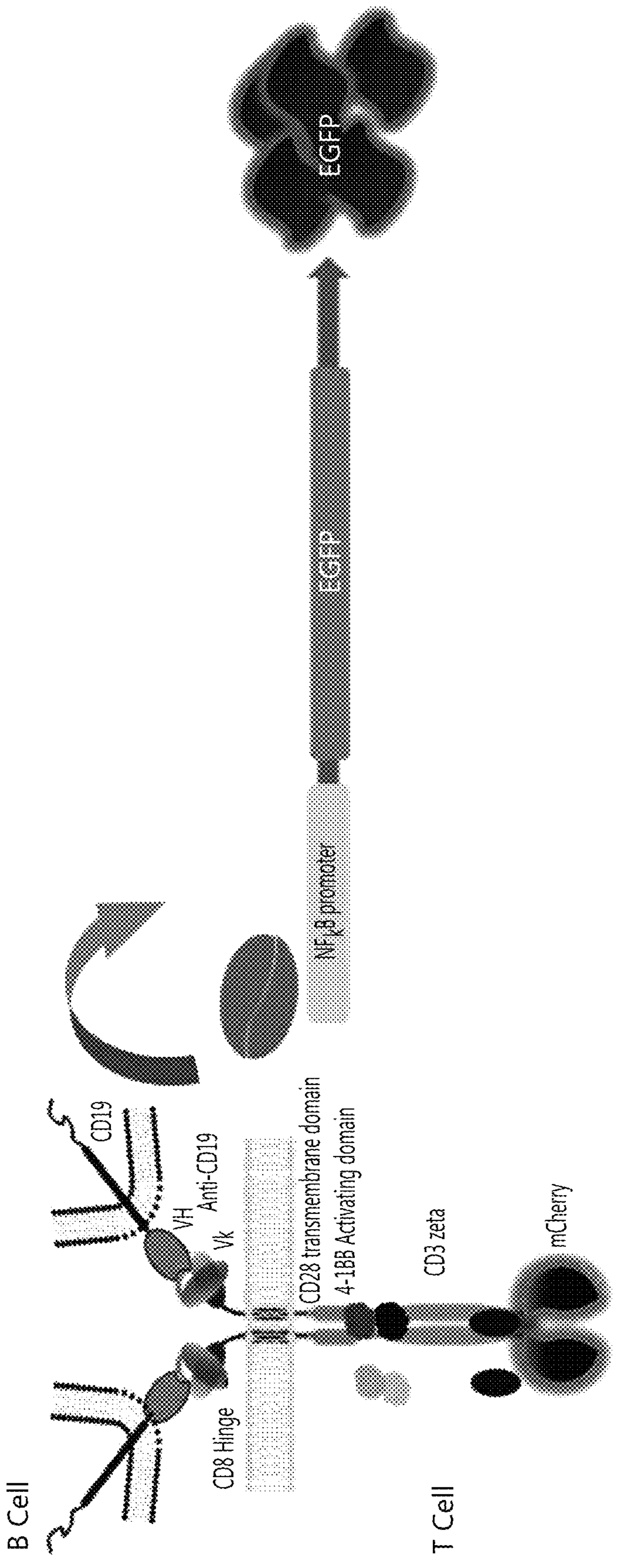
FIGS. 4A-4D illustrate a schematic of a CAR-T activation assay.
Figure 4B:
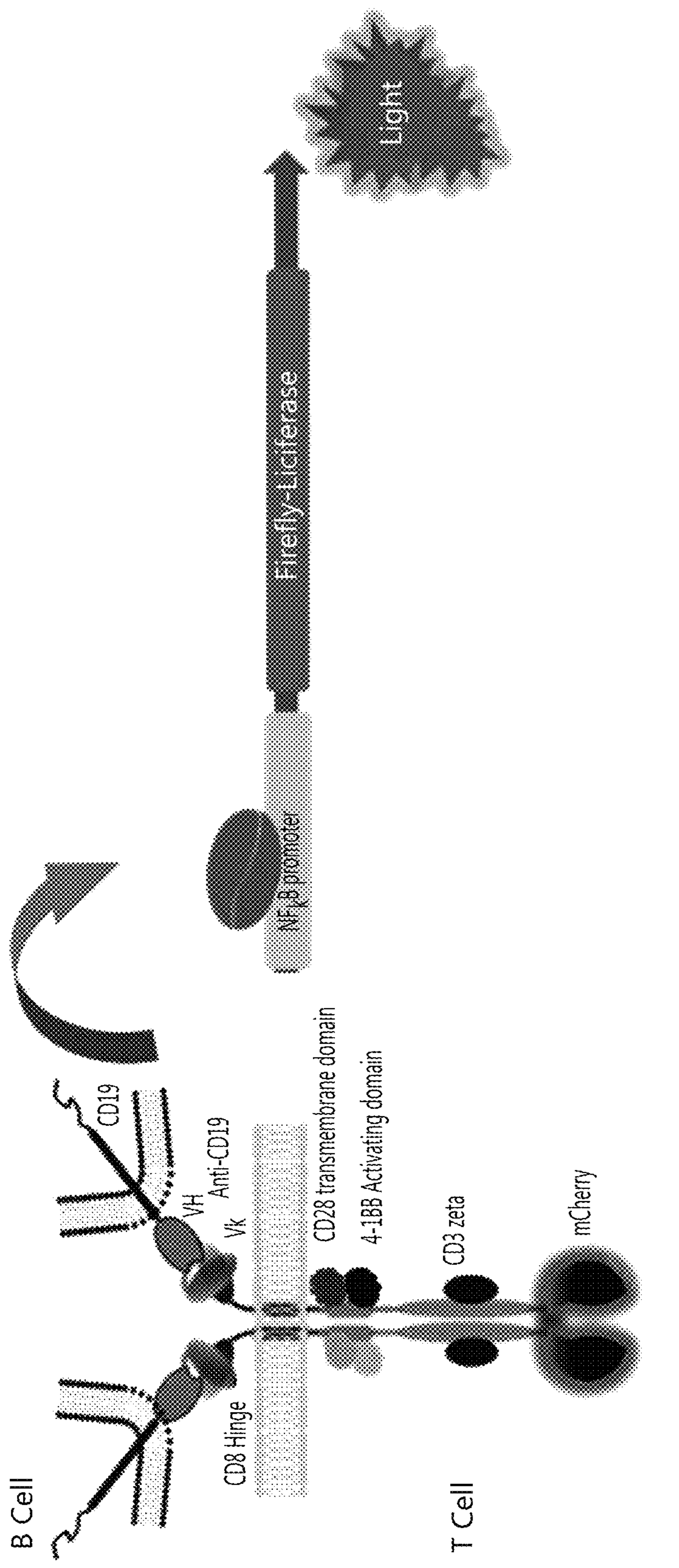
Figure 4C:
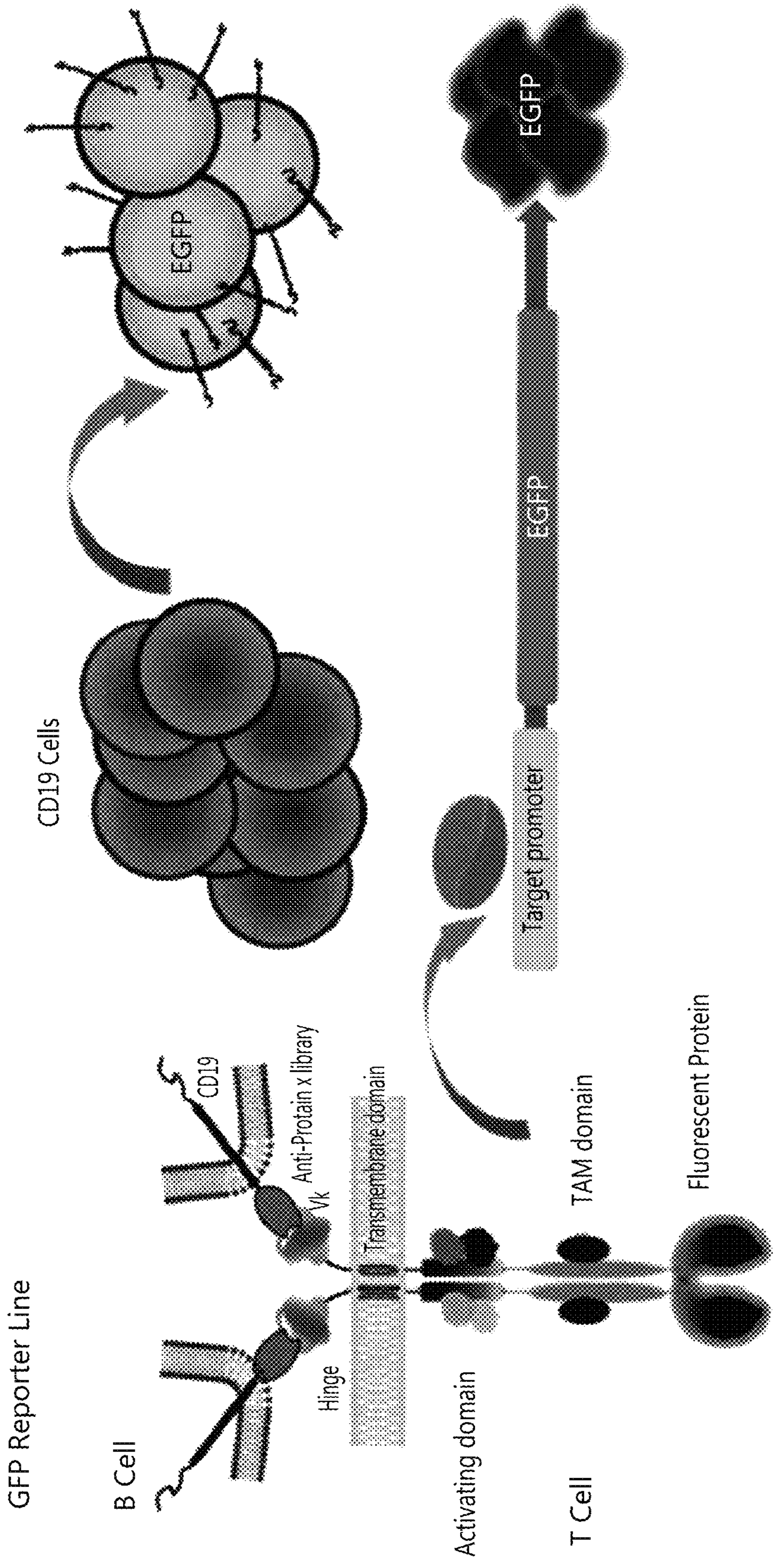
Figure 4D:
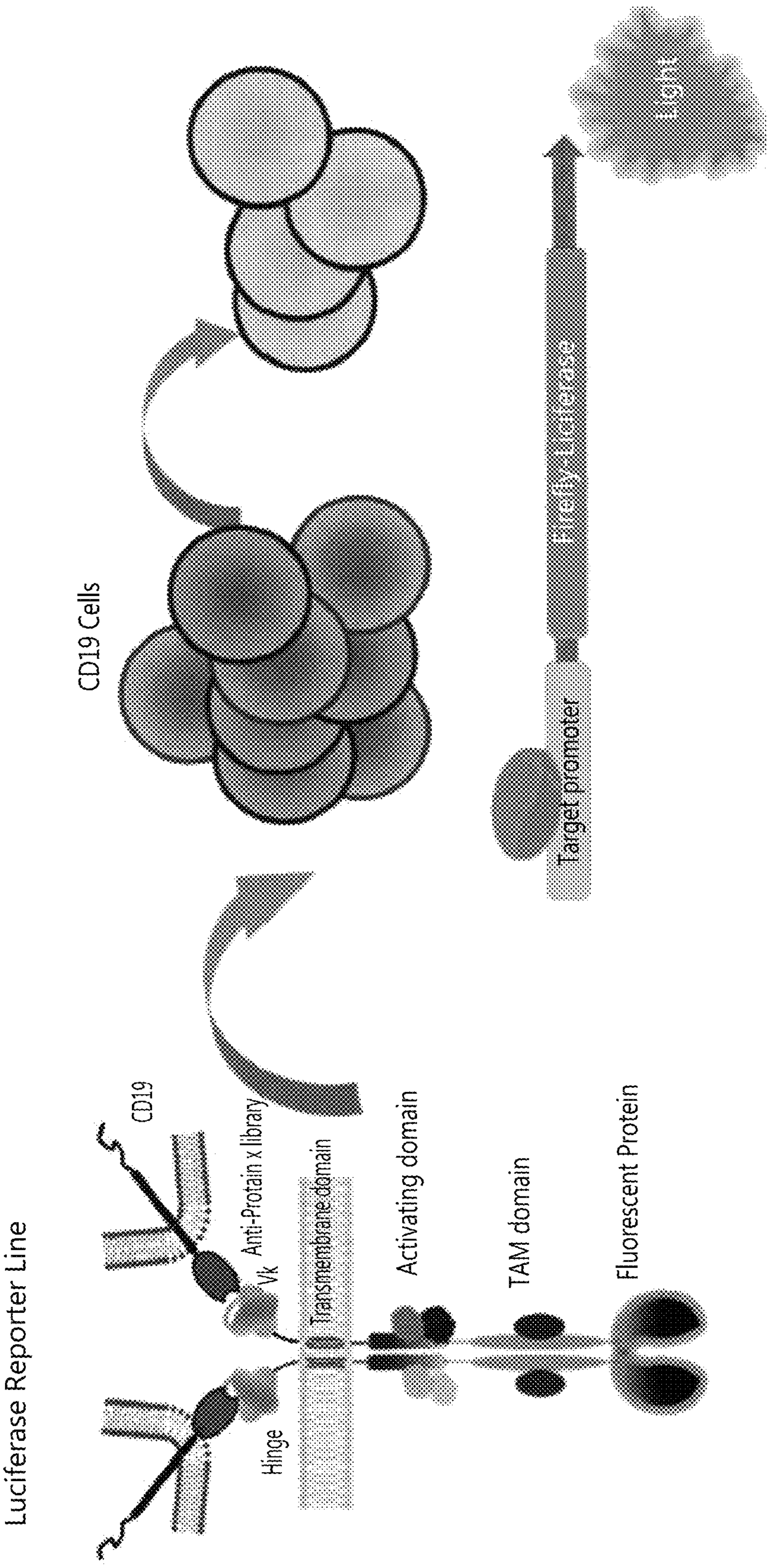
Figure 7A:
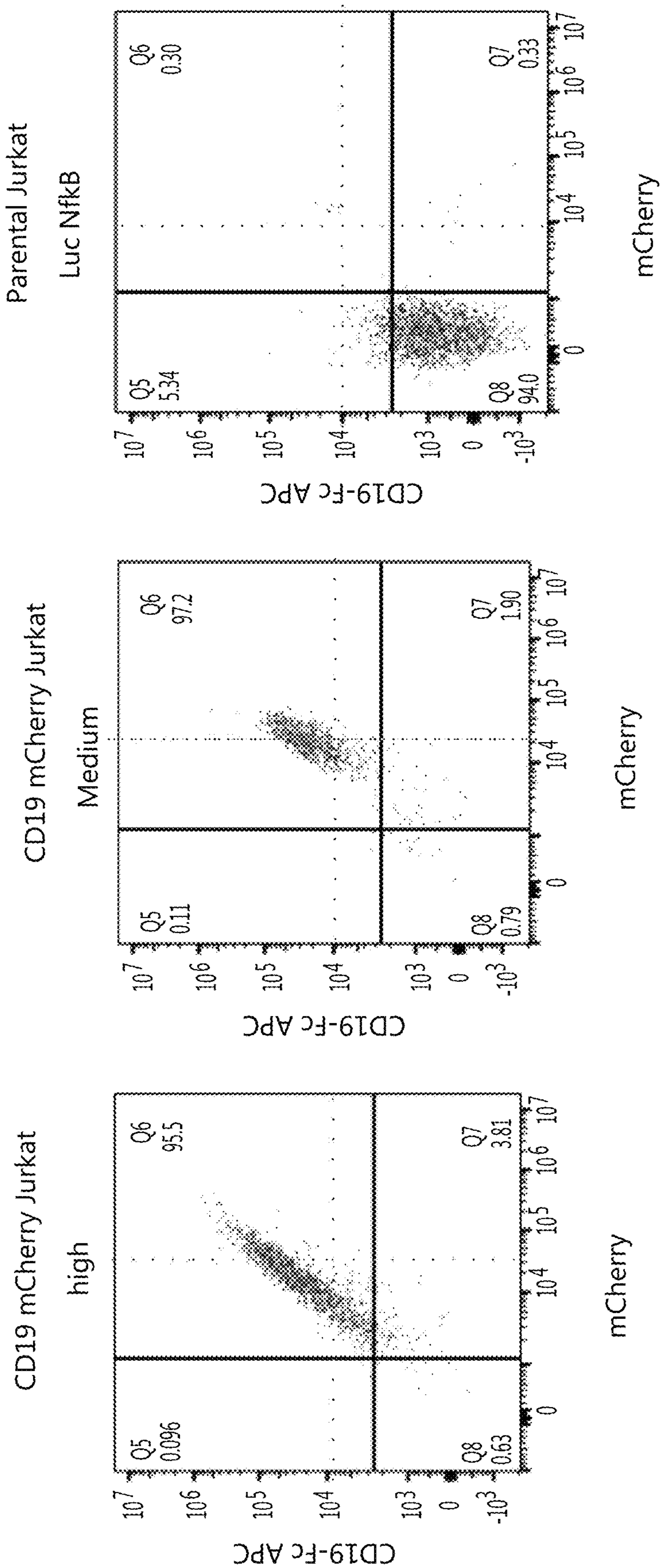
FIGS. 7A-7N illustrate a test of activity of an anti-CD19 CAR-T construct.
Figure 7B:
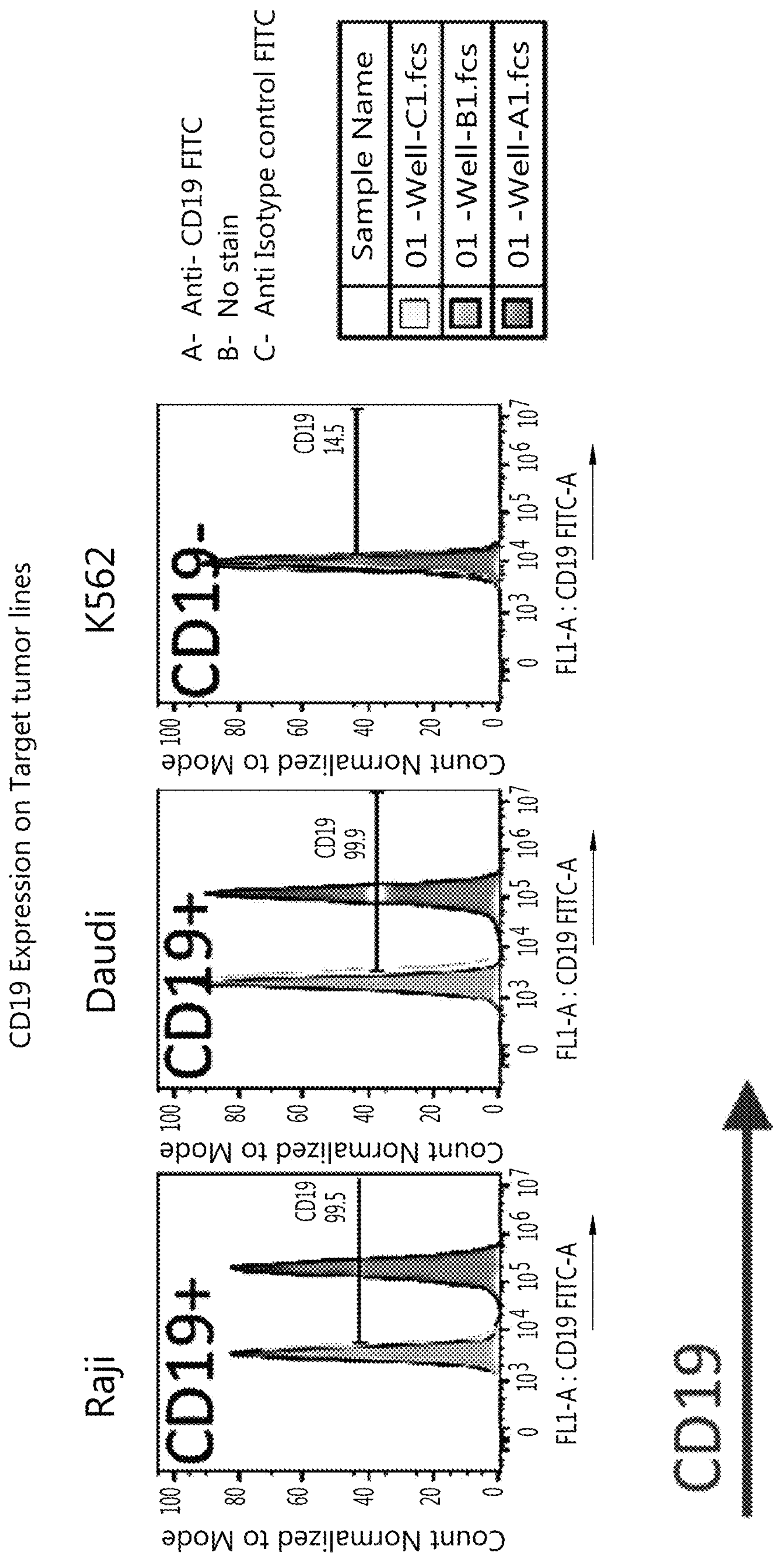
FIG. 7B illustrates CD19 expression in two tumor cell lines that express CD19 (Raji and Daudi) and one cell line lacking CD19 (K562) after incubation with the Jurkat NFκB-Luc CART19 high cell line and Jurkat NFκB-Luc CART19 medium cell line.

CARs with a CD19 antigen binding domain and CART19 were transduced using a lentiviral system into Jurkat NFκB-Luc to produce Jurkat NFκB-Luc CART19 cell lines (FIG. 4B). Two Jurkat NFκB-Luc CART19 cell lines were generated in this system with high CART19 expression and medium CART19 expression versus the parental Jurkat cell line (FIG. 7A). These high and medium cell lines were incubated with tumor lines expressing CD19 (Raji and Daudi) or lacking expression of CD19 (K562 cell line) (FIG. 7B). Jurkat-NFκB-Luc CART19 high cells, Jurkat NFκB-Luc CART19 medium cells, or Jurkat NFκB-Luc parental cells were incubated with target CD19 Cells (Raji, Daudi, and K562 cell lines) in the concentrations indicated in FIGS. 7C-7N.

Figures 7C, 7D, 7E, 7F, 7G, 7H:
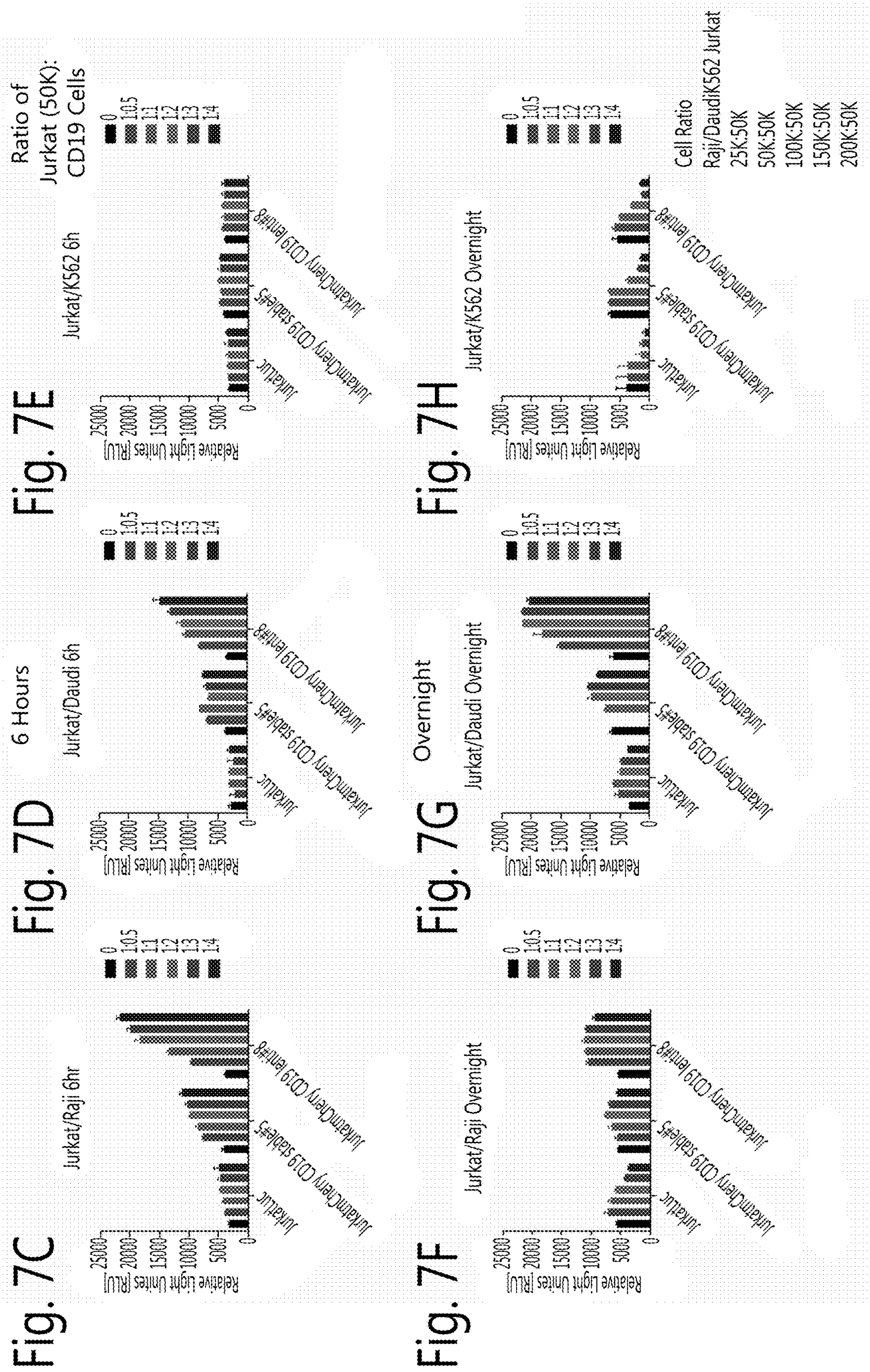
FIG. 7C illustrates the three Jurkat cell lines incubated with Raji cells for 6 hours.
FIG. 7D illustrates the three Jurkat cell lines incubated with Daudi cells for 6 hours.
FIG. 7E illustrates the three Jurkat cell lines incubated with K562 cells for 6 hours.
FIG. 7F illustrates the three Jurkat cell lines incubated with Raji cells overnight.
FIG. 7G illustrates the three Jurkat cell lines incubated with Daudi cells overnight.
FIG. 7H illustrates the three Jurkat cell lines incubated with K562 cells overnight.
Figure 7I:
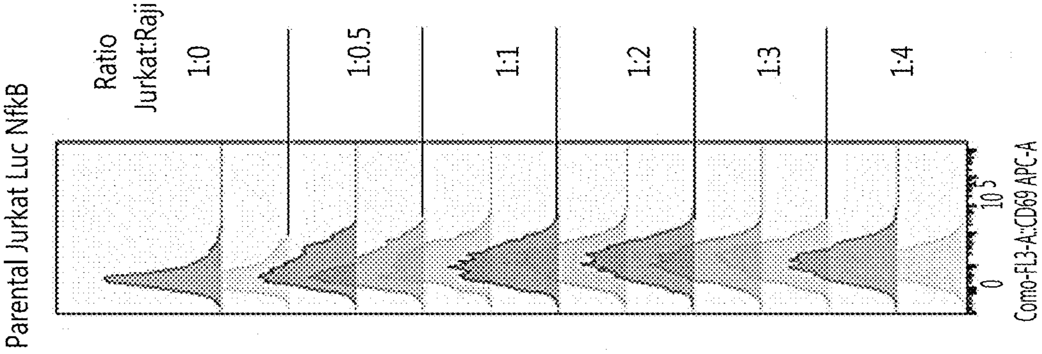
FIG. 7I illustrates CD69 expression in Jurkat NFκB-Luc parental cells incubated with Raji cells for 6 hours.
Figure 7J:
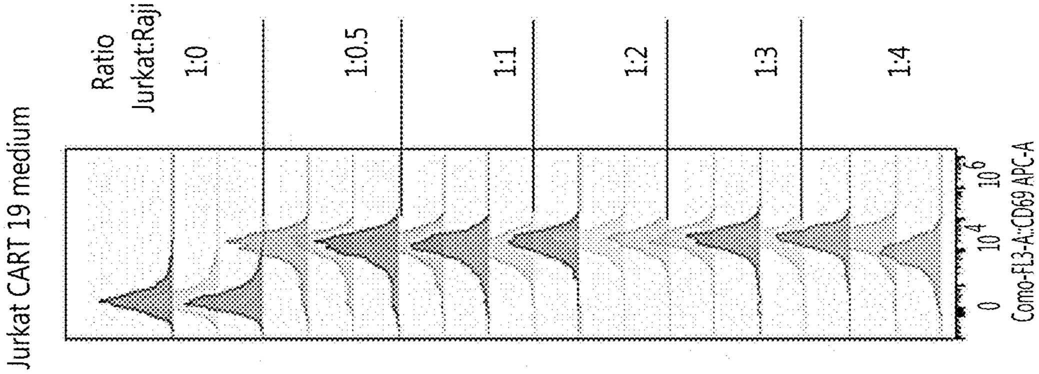
FIG. 7J illustrates CD69 expression in Jurkat NFκB-Luc CART19 medium cells incubated with Raji for 6 hours.
Figure 7K:
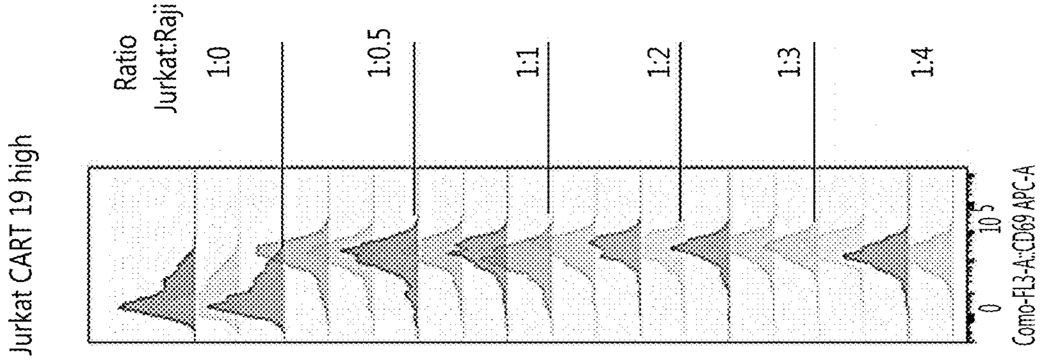
FIG. 7K illustrates CD69 expression in Jurkat NFκB-Luc CART19 high cells for included with Raji cells for 6 hours.
Figures 7L, 7M, 7N:
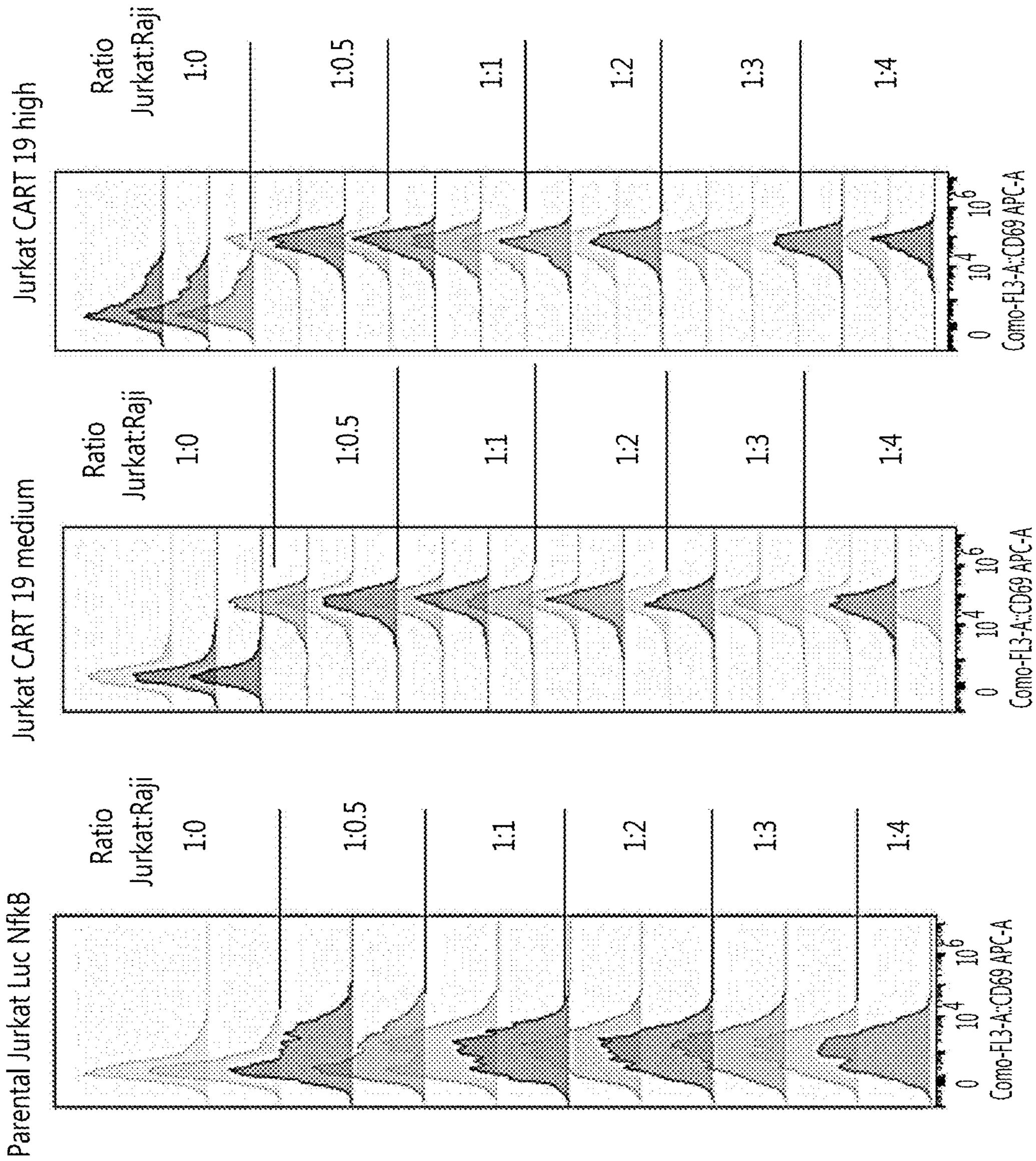
FIG. 7L illustrates CD69 expression in Jurkat NFκB-Luc parental cells incubated with Raji cells overnight.
FIG. 7M illustrates CD69 expression in Jurkat NFκB-Luc CART19 medium cells incubated with Raji overnight.

Cells were incubated for 6 hours (FIGS. 7C-7E) or overnight (FIGS. 7F-7H). Cells were then lysed, and a luciferin substrate was added using Bright Glo kit (Promega according to the manufacturer protocol) and the light output was measured using a luminometer. Data were presented as the average of the relative light units (RLUs) of three replicates±standard error mean (SEM). Replicate plates of Jurkat NFκB-Luc CART19 cell lines incubated with Raji CD19+ cells line were subjected to FACS analysis. Cells were harvested and stained with anti-human CD69 and analyzed by FACS analyzer (FIGS. 7I-7N).

The data from this example demonstrated that the CART19 construct was functionally active, as shown by the increase in the RLUs, i.e., NFκB activation, that correlated with an increase in the target cells expressing CD19 (Raji and Daudi). The activation also correlated with the CART19 expression on the cell surface. Stronger response, elucidated with higher NFκB activation (RLUs), was observed when CART19 high was incubated with Raji and Daudi cell lines, and a weaker response was observed when the medium CART 19 expressor cells were used. This response was CD19-dependent due to the background response that was observed with target cells that lacked CD19 expression (i.e., K562 cell line). In the NFκB luciferase system, 6 hours of activation between effector cells (Jurkat CART19) and Target cells (Raji) was optimal. While overnight activation between effector cells (Jurkat CART19) and Target cells (Daudi) was optimal this could be due to the Raji cell line being more aggressive than the Daudi cell line.

CD69 expression was upregulated due to CART 19 activation (FIGS. 7I-7N). Jurkat parental or Jurkat CART19 high and medium were incubated separately with Raji for 6 hours and overnight and then harvested, and CD69 was measured by flow cytometry on mCherry-gated cells. CART19 was activated when incubated with Raji, as shown by the increase of CD69 surface expression. Control Jurkat NFκB luciferase were tested in duplicate and CART19 Jurkat were tested in triplicate. CD69 increased after 6 hour and sustained high expression at the overnight timepoints.

Example 5: Screening of Jurkat NFκB-GFP CART19

CARs with a CD19 antigen binding domain and CART19 were transduced using a lentiviral system into Jurkat NFκB-GFP to produce Jurkat NFκB-GFP CART19 cell lines (FIG. 4A). In this system, once the CAR19-GFP encounters a cell expressing CD19 (the antigen), the CAR signals through the 4-1BB and CD3 zeta and activates NFκB-promoter that will express high levels of GFP in the cells. Other markers will be induced due to CD3 zeta activation such as CD69 or CD25. mCherry MFI also increases due to the cluster of the CAR T complexes.

Figure 8:
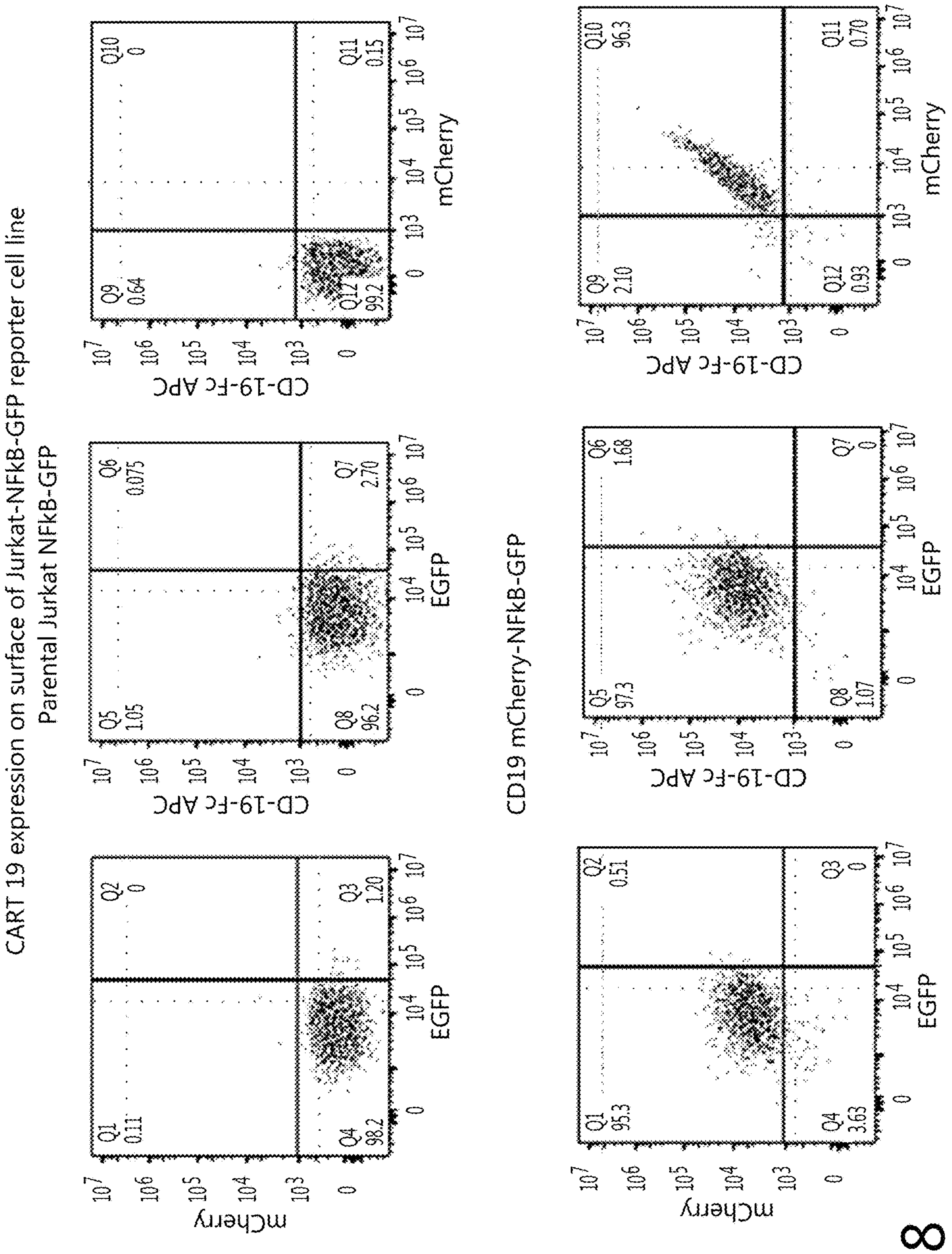
FIG. 8 illustrates CART19 expression on the surface of Jurkat-NFκB-GFP reporter cell lines.

Expression of CART19-GFP by flow cytometry was indicated by co-staining of mCherry and CD19 labeled with an APC fluorophore (FIG. 8). The baseline of GFP was indicated as well, in comparison to parental Jurkat NFκB-GFP, which indicated that the CART 19 did not activate the NFκB promoter simultaneously.

Figure 9A:
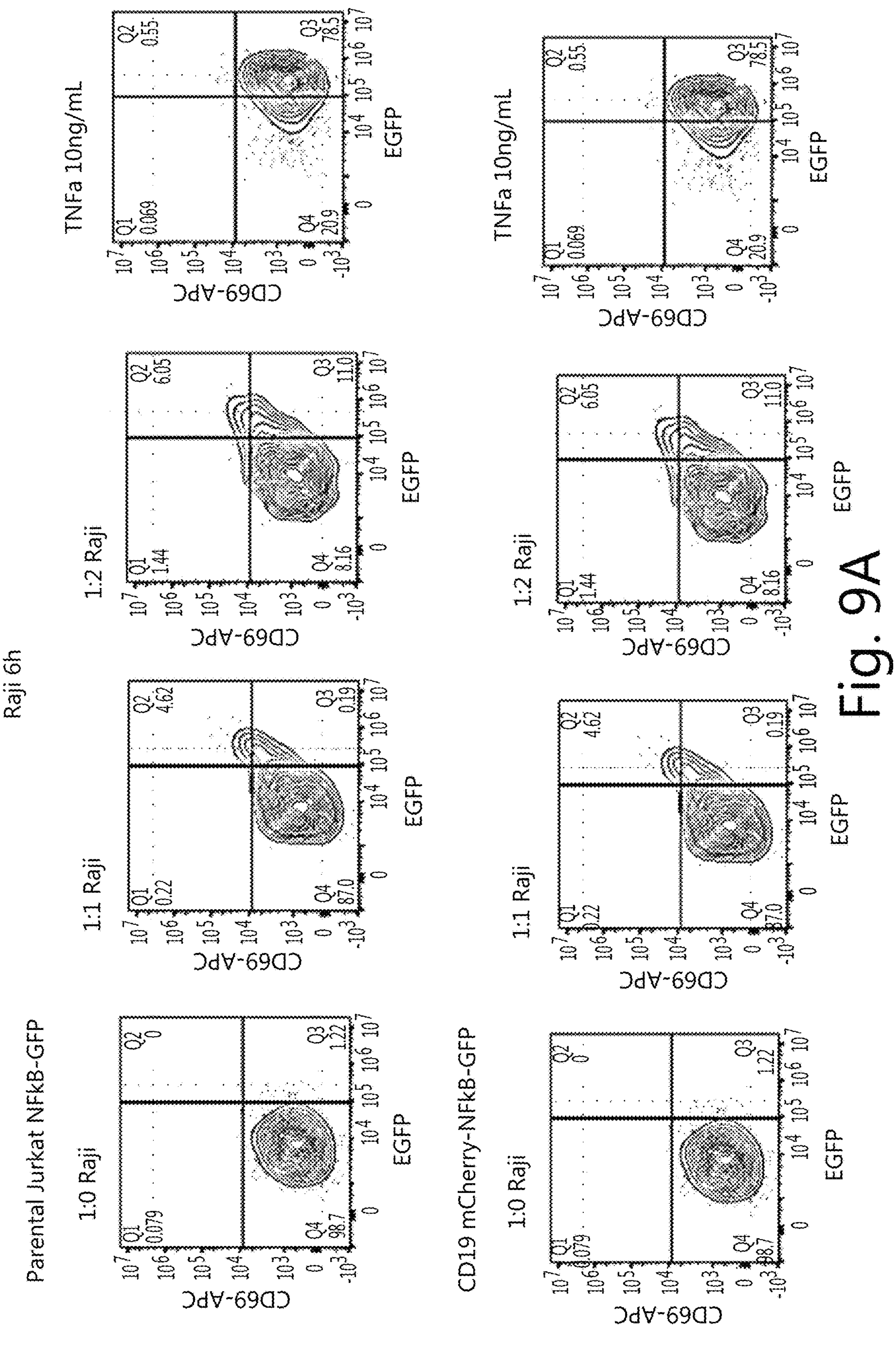
Figure 9C:
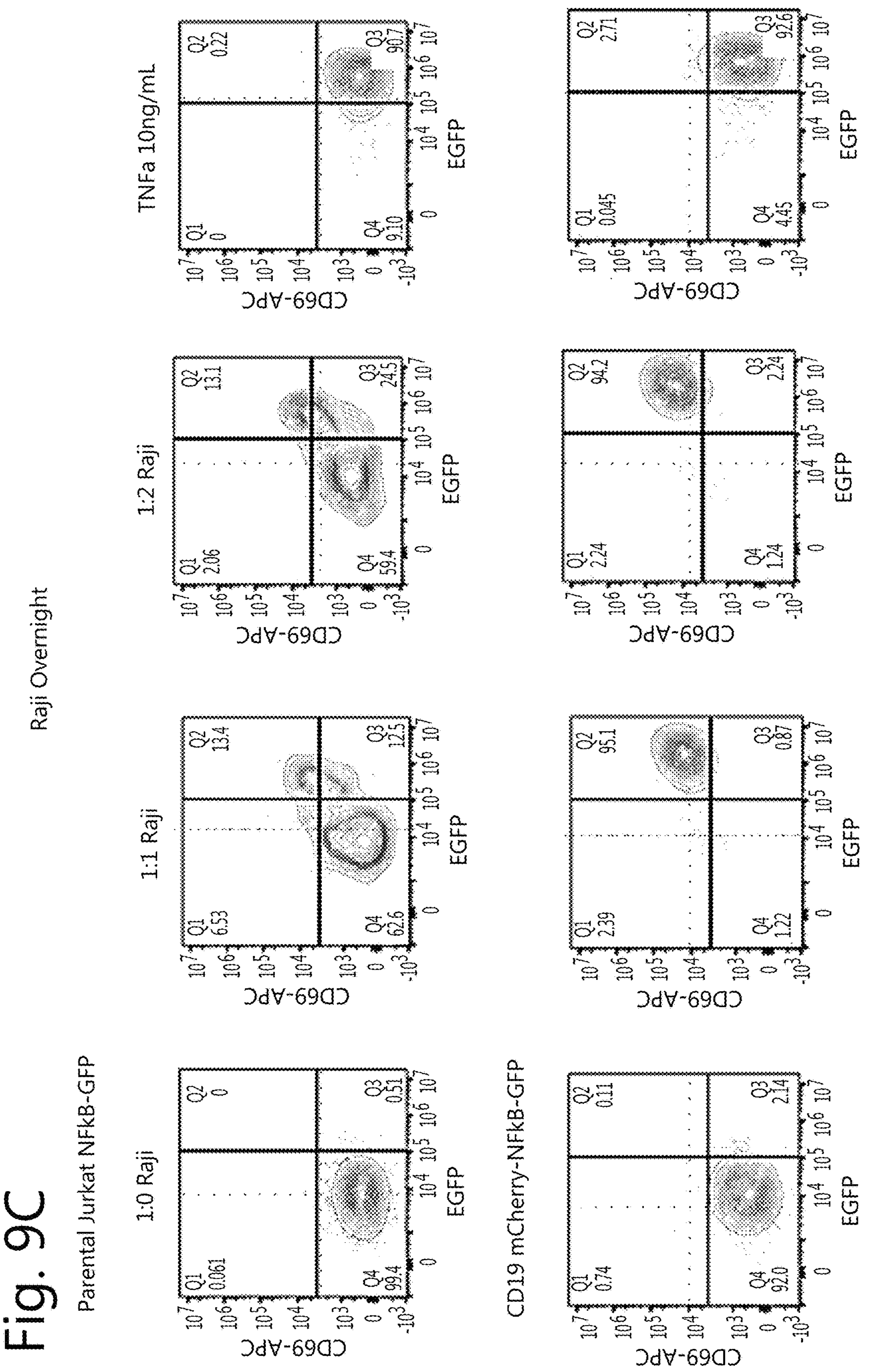
Figure 9E:
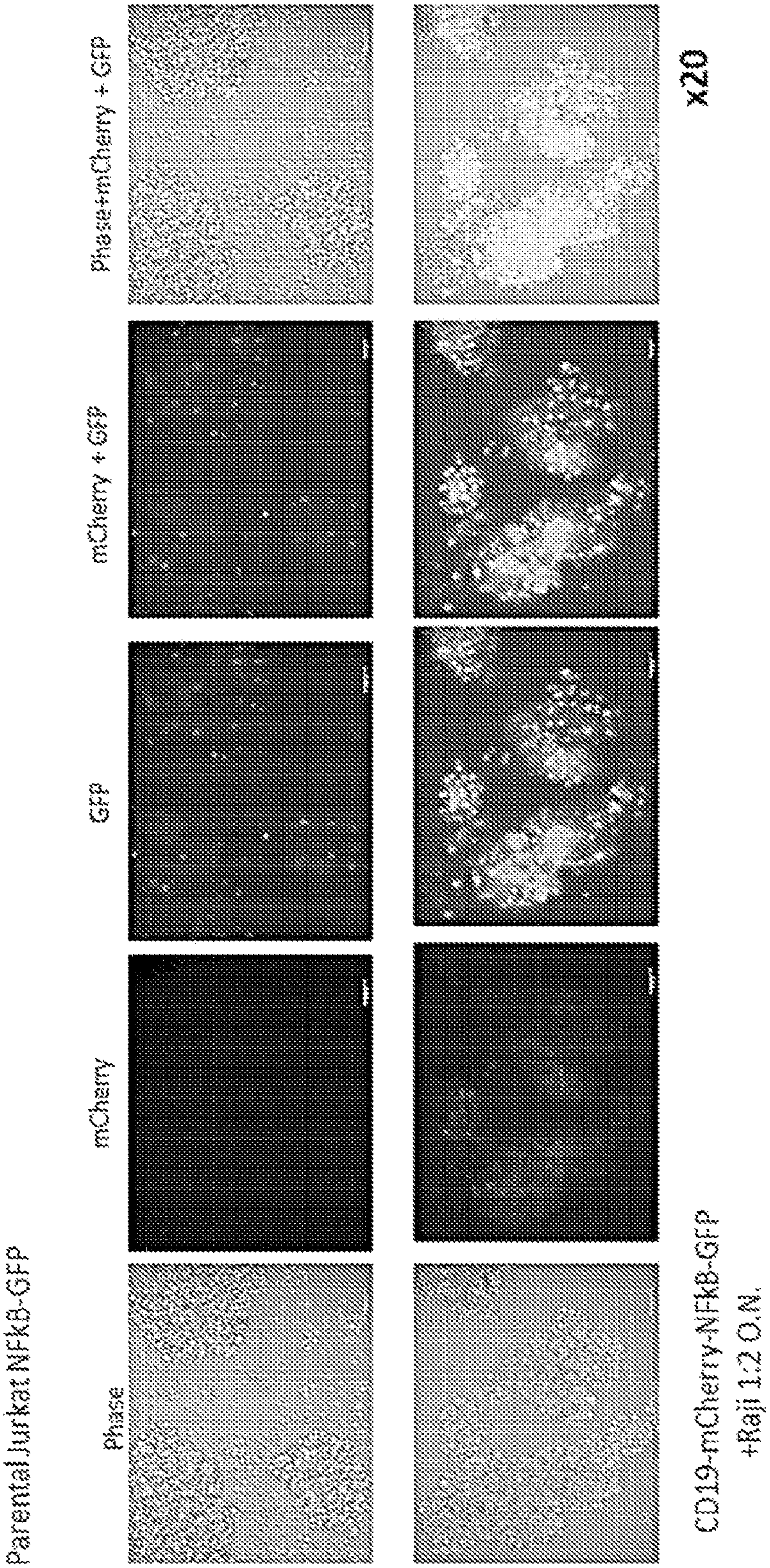

Raji activated Jurkat NFκB-GFP CART19, as shown by GFP and CD69 high co-expression after 6-hour (FIGS. 9A, 9B) and overnight (FIGS. 9C, 9D) incubation with Raji cell line. Basal activation was detected in the parental cell line due to background activation of the endogenous TCR and tonic signaling mainly GFP signaling. FIG. 9A and FIG. 9C showed each time point gated on mCherry positive cells and co-expression of GFP and CD69. FIG. 9B and FIG. 9D are the overlaid histograms of GFP and CD69 in duplicates. The mean fluorescent intensity (MFI) of fluorescent shifts are indicated in the tables below each histogram plot. TNF alpha stimulation was used as a positive control to ensure GFP (i.e., NFκB pathway) was active. No activation of CD69 was observed in this condition since this cytokine does not signal through the TCR (i.e., CD3 zeta expressed in the CART19 construct). Fluorescent microscopy showed the co-localization of the activated CART19 mCherry and GFP when activated in the presence of Raji cells (FIG. 9E). Co-localization was shown in yellow. The parental line showed background levels of GFP signaling due to basal proliferation of the Jurkat (as it is a tumor line).

Figure 10A:
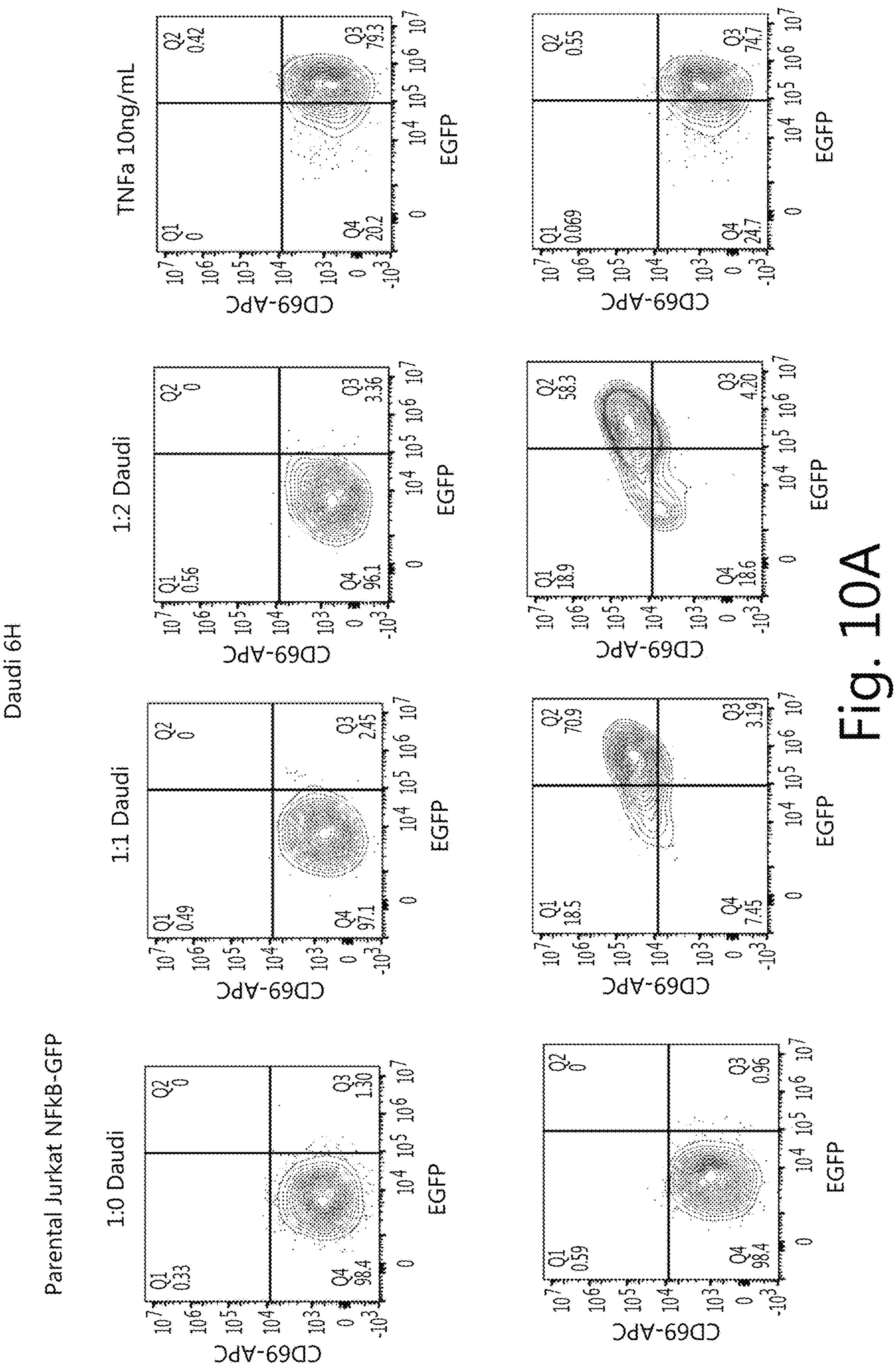
Figure 10C:
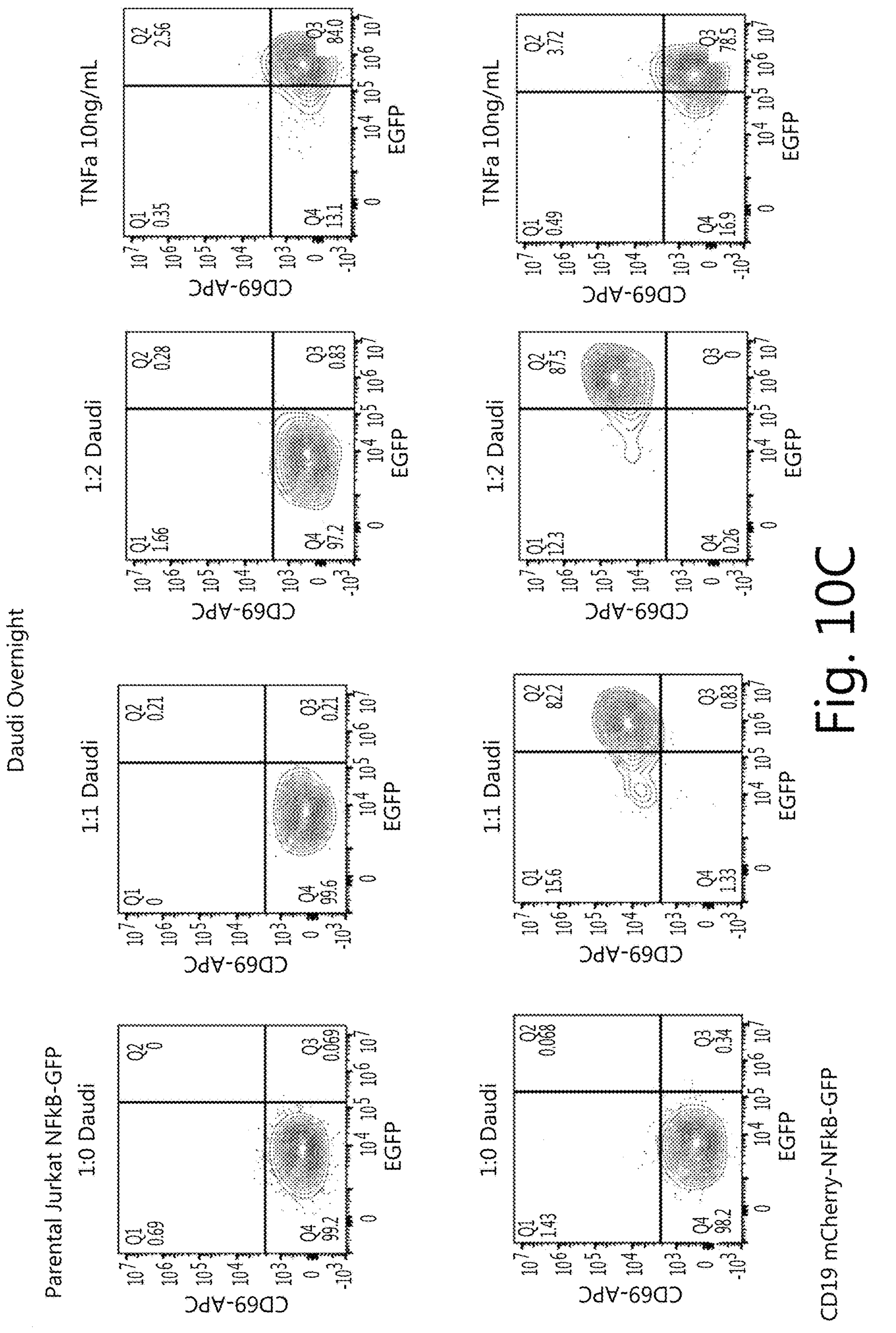

Daudi activated Jurkat NFκB-GFP CART19, as shown by GFP and CD69 high co-expression after 6-hour (FIGS. 10A, 10B) and overnight (FIGS. 10C, 10D) incubation with Daudi cell line. Basal activation was detected in the parental cell line due to background activation of the endogenous TCR and tonic signaling mainly GFP signaling. FIG. 10A and FIG. 10C showed each time point gated on mCherry positive cells and co-expression of GFP and CD69. FIG. 10B and FIG. 10D are the overlaid histograms of GFP and CD69 in duplicates. The MFI of fluorescent shifts are indicated in the tables below each histogram plot. TNF alpha stimulation was used as a positive control to ensure GFP (i.e., NFκB pathway) was active. No activation of CD69 was observed in this condition since this cytokine does not signal through TCR (i.e., CD3 zeta expressed in the CART 19 construct).

Figure 11A:
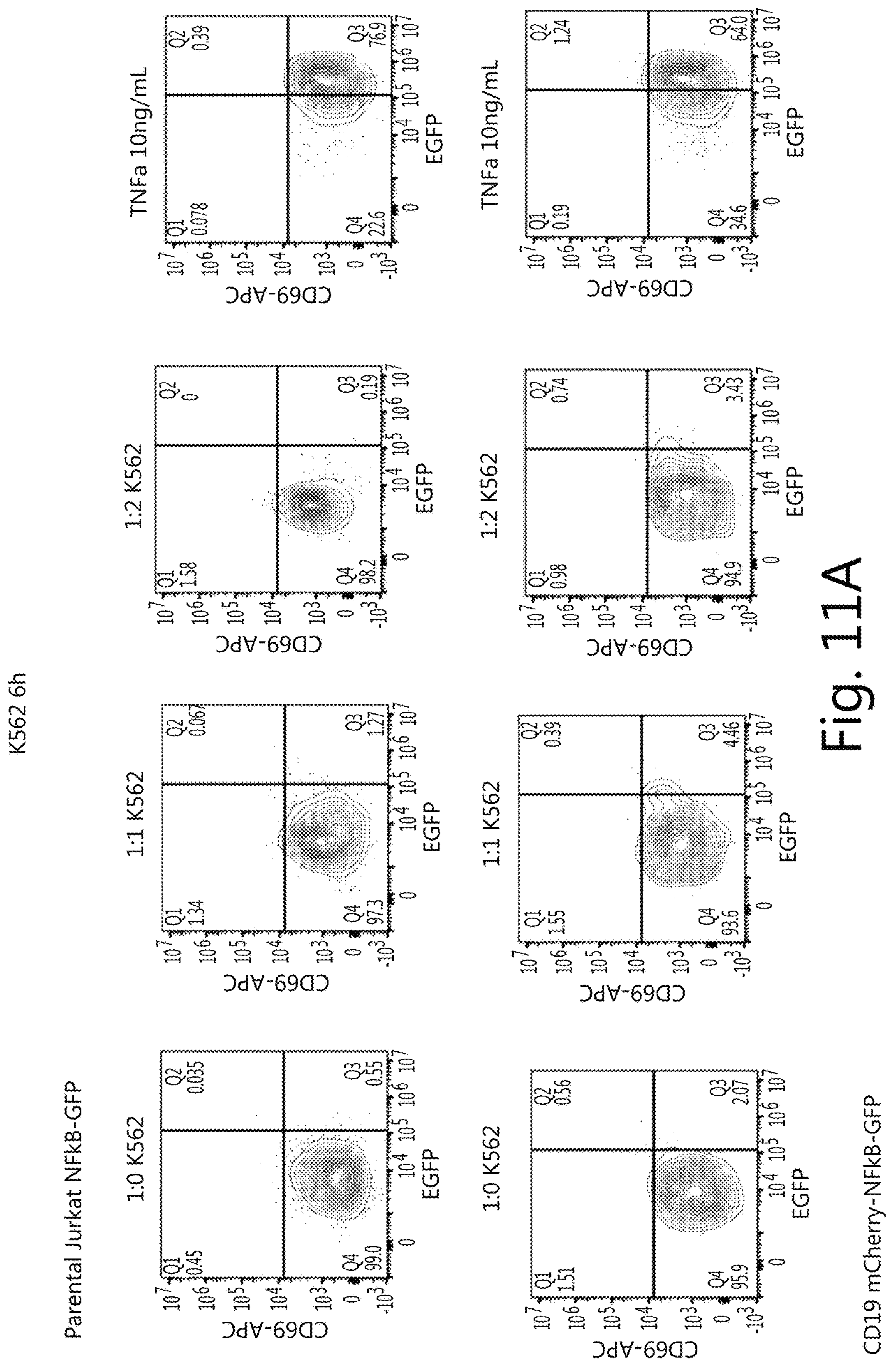
Figure 11C:
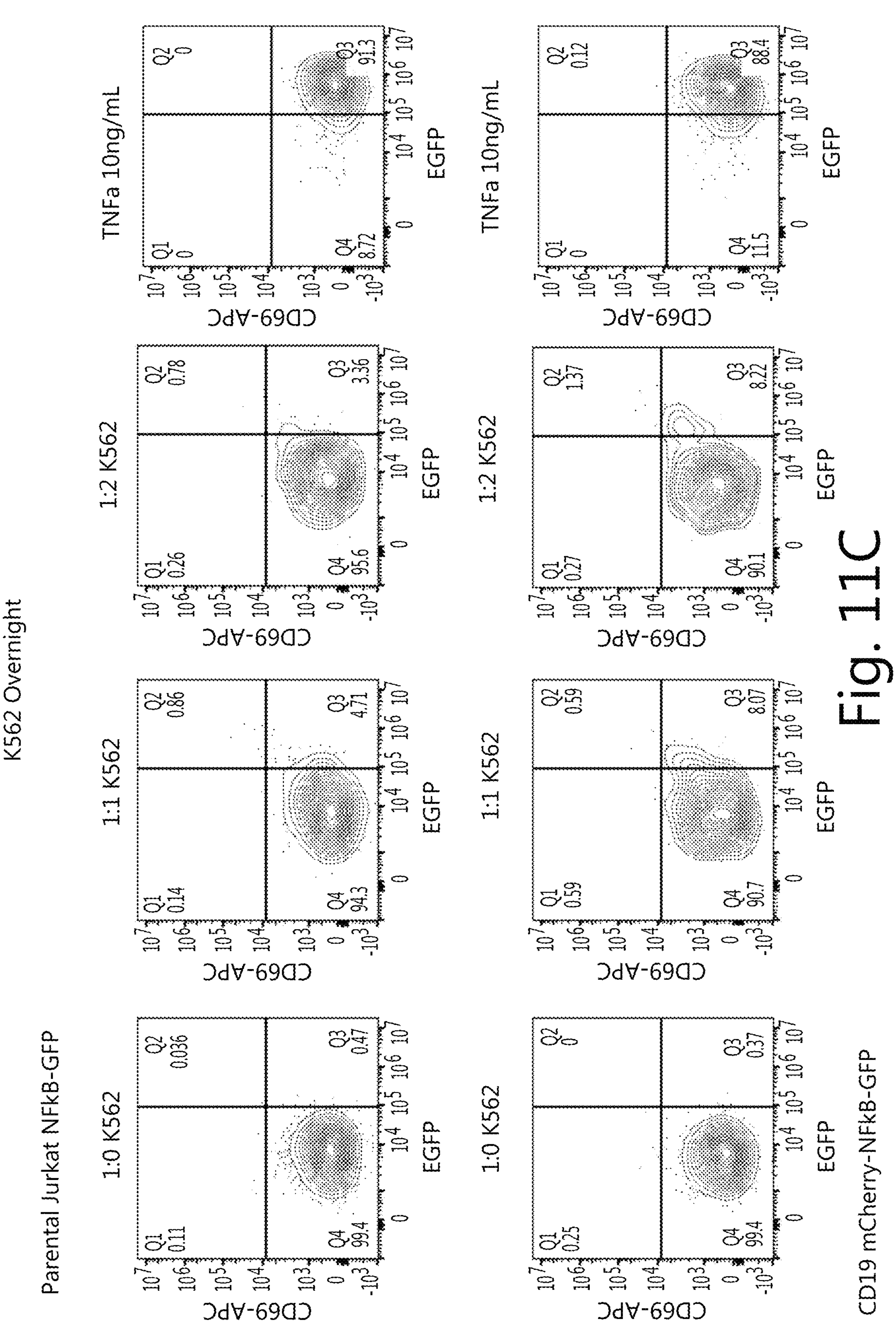
Figure 11D:
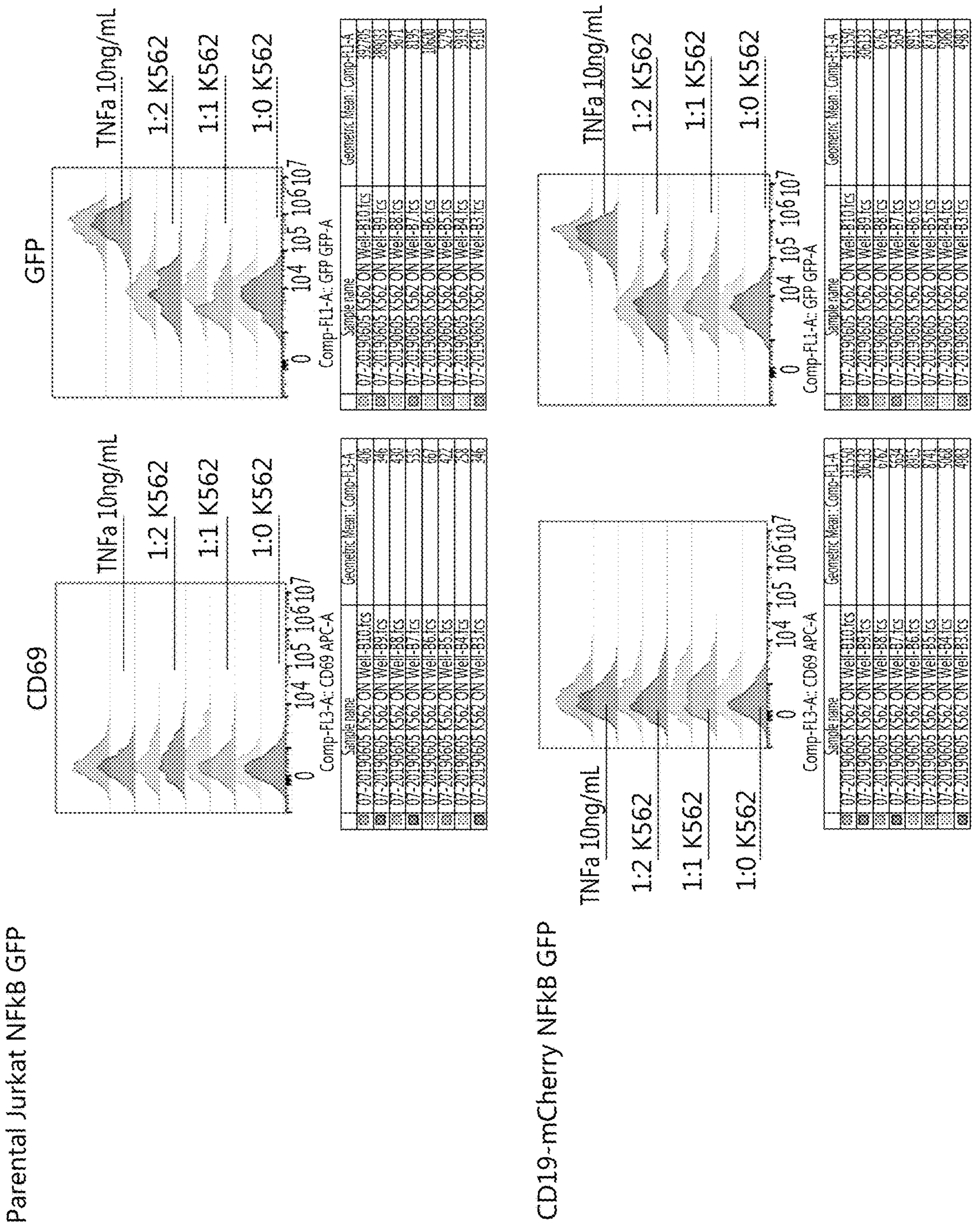
Figure 12A:
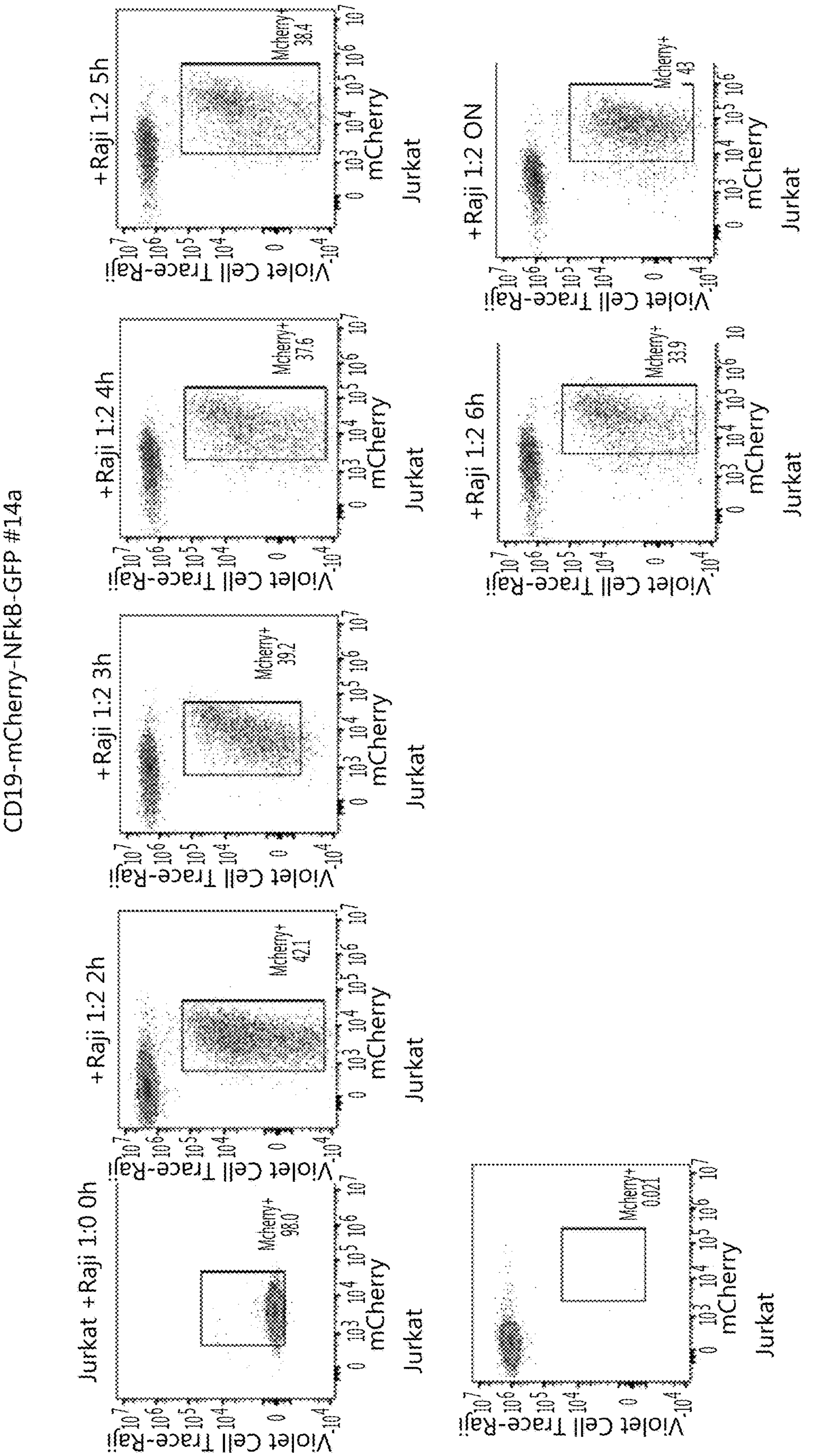
Figure 12B:
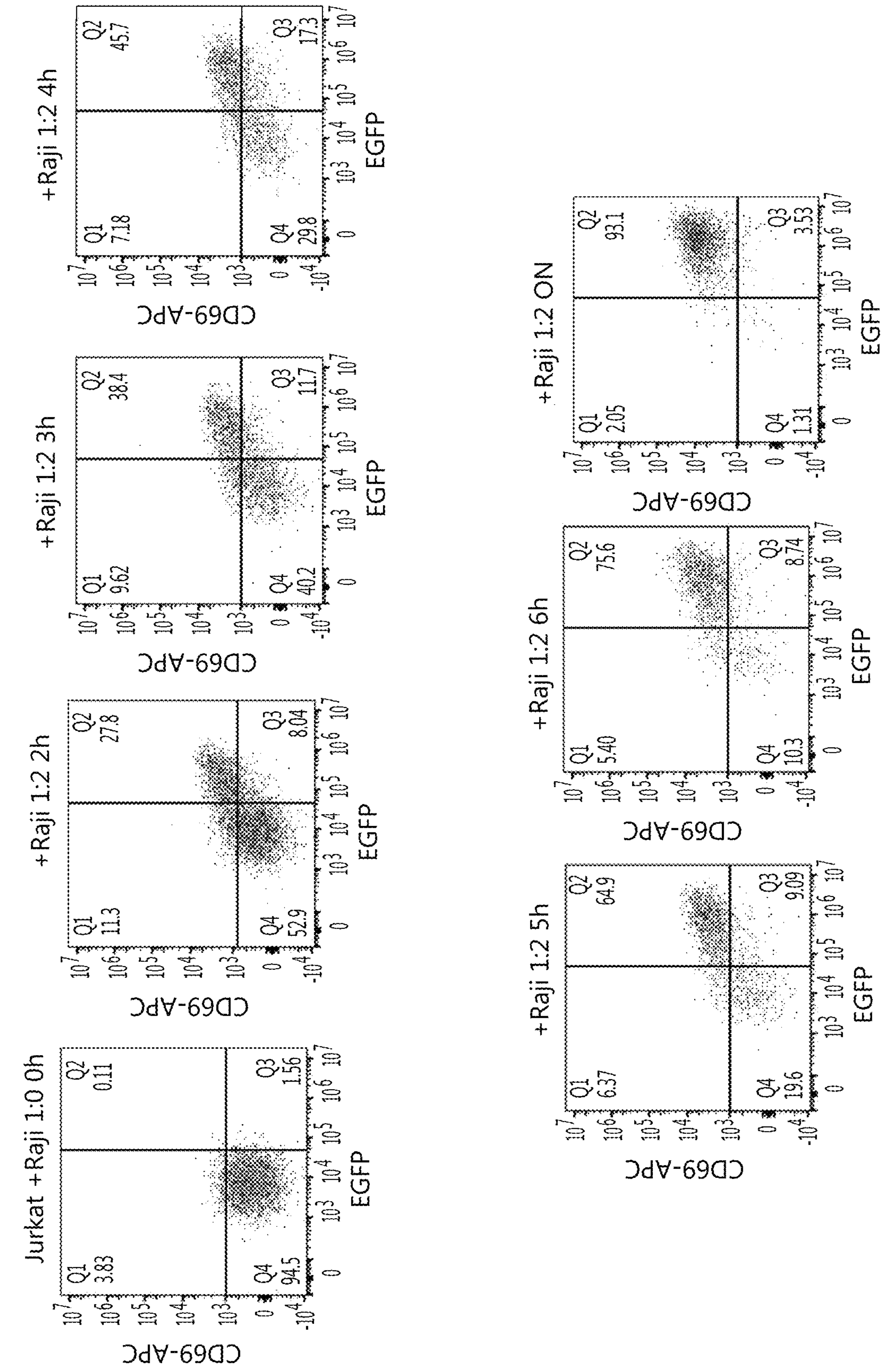
Figure 12D:
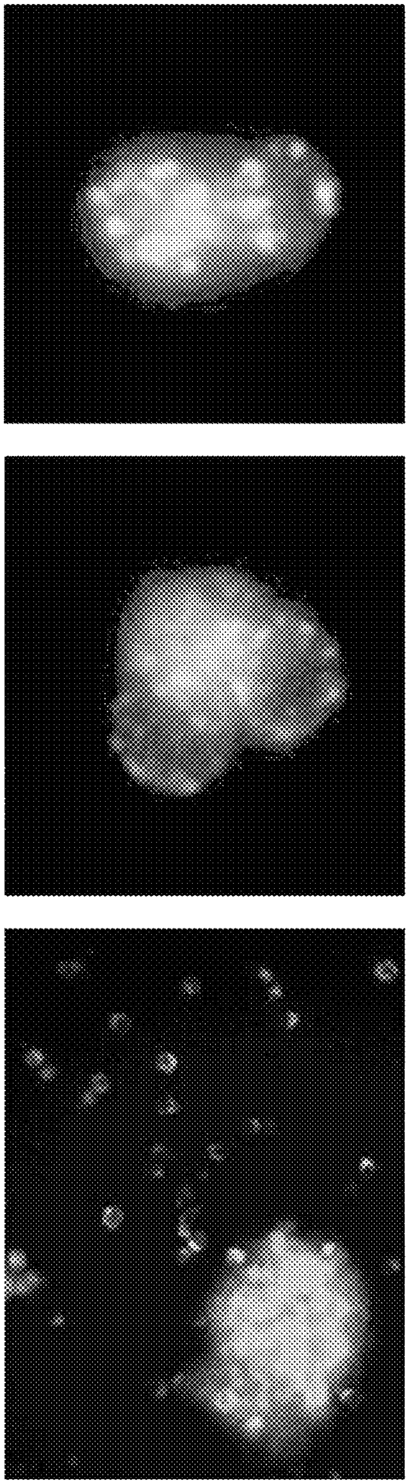

The K562 cell line did not activate Jurkat NFκB-GFP CART19 due to lack of CD19 expression in this line. Neither GFP nor CD69 were expressed after 6 hours (FIG. 11A, 11B) or overnight (FIGS. 11C, 11D) post the incubation with the K562 cell line. Basal activation was detected in the parental cell line and the CART line due to background activation of the endogenous TCR and tonic signaling mainly GFP signaling. FIG. 11A and FIG. 11C showed each time point gated on mCherry positive cells and co expression of GFP and CD69. FIG. 11B and FIG. 11D are the overlaid histograms of GFP and CD69 in duplicates. The MFI of fluorescent shifts are indicated in the tables below each histogram plot. TNF alpha stimulation was used as a positive control to ensure GFP (i.e., NFκB pathway) was active. No activation of CD69 was observed in this condition since this cytokine does not signal through TCR (i.e., CD3 zeta expressed in the CART 19 construct).

A time course of CART19 activation and GFP and CD69 co-expression was carried out to test the range of when CART19 activation was maximal in order to plan the optimal timepoint of library panning times (FIGS. 12A-12D). Jurkat NFκB-GFP CART19 was incubated with target cell line, Raji (1 Jurkat cell to 2 Raji cells as previous studies indicated as ideal activation (FIGS. 7A-7N, FIGS. 9A-9E, and FIGS. 10A-10D)). To separate Raji cells from Jurkat NFκB-GFP CART19 cells, Raji cells were labeled with a violet cell trace (Invitrogen, Thermo Fisher Scientific) to rule out tumor cells from CARs during the sorting of the activated CART during the panning.

FIG. 14 shows that the methods detailed herein work with two different CART libraries specific for different antigens.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of screening a library of cells comprising:

a) contacting a plurality of cells with a target antigen; the plurality of cells comprising a library of recombinant polypeptides, wherein each recombinant polypeptide comprises an antigen binding domain, a transmembrane domain, an activation domain or an inhibition domain, and a first detectable marker, and wherein the antigen binding domain differs among the plurality of cells;

b) selecting cells that display expression of a first T cell activation marker, thereby producing a first subset of activated cells;

c) contacting the subset of activated cells with a plurality of cells not expressing the target antigen; and d) selecting cells of the subset of activated cells that do not display expression of an a second T cell activation marker, thereby producing a subset of low-background binding, activated cells.

2. The method of claim 1, further comprising contacting the subset of low-background, activated cells with the target antigen and selecting cells from the low-background, activated cells that display activation of a third T cell activation marker, thereby producing a subset of high antigen-binding, low-background binding activated cells.

3. The method of claim 1, wherein the target antigen is immobilized to a solid support.

4. The method of claim 3, wherein the solid support is a bead.

5. The method of claim 3, wherein the solid support is a column.

6. The method of claim 1, wherein the target antigen is a soluble antigen.

7. The method of claim 3, wherein the target antigen is conjugated to a detectable moiety.

8. The method of claim 1, wherein the recombinant polypeptide comprises a detectable tag.

9. The method of claim 1, wherein the first T cell activation marker, the T cell second activation marker, and the third T cell activation marker are the same.

10. The method of claim 1, wherein the plurality of cells further comprises a nucleic acid sequence encoding a reporter polypeptide.

11. The method of claim 10, wherein the reporter nucleic acid comprises a reporter gene under the control of an immune cell promoter, and wherein the second T cell activation marker or the third T cell activation marker comprises the reporter polypeptide.

12. The method of claim 10, wherein the reporter polypeptide comprises a fluorescent protein or a luciferase protein.

13. The method of claim 11, wherein the immune cell promoter comprises a nuclear factor κB (NFκB) promoter or a Nuclear factor of activated T-cells (NFAT) promoter.

14. The method of claim 1, wherein the first T cell activation marker comprises an endogenous T cell activation marker.

15. The method of claim 1, wherein the second T cell activation marker or the third T cell activation marker comprises an endogenous T cell activation marker.

16. The method of claim 1, wherein the first T cell activation marker is selected from the group consisting of CD69, CD25, and a combination thereof.

17. The method of claim 1, wherein the antigen binding domain comprises a single-chain variable fragment (scFv).

18. The method of claim 1, wherein each recombinant polypeptide comprises two or more different antigen binding domains.

19. The method of claim 18, wherein one or more of the two or more different antigen binding domains binds to CD3.

20. The method of claim 1, wherein the library of recombinant polypeptides comprises at least $1\times10^5$ different antigen binding domains.

* * * * *